(12) United States Patent
Saunier et al.

(10) Patent No.: US 9,052,321 B2
(45) Date of Patent: Jun. 9, 2015

(54) FLAVIVIRUS-BASED SYSTEM FOR PRODUCTION OF HEPATITIS C VIRUS (HCV)

(75) Inventors: Bertrand Saunier, Versailles (FR); Miriam Triyatni, Montclair, NJ (US); Edward A. Berger, Rockville, MD (US)

(73) Assignees: The United States of America, as represented by the Secretary, Department of Health and Human Services, Washington, DC (US); INSERM (Institut National de la Sante et de la Recherche Medicale), Paris (FR)

( * ) Notice: Subject to any disclaimer, the term of this patent is extended or adjusted under 35 U.S.C. 154(b) by 1101 days.

(21) Appl. No.: 13/122,154

(22) PCT Filed: Sep. 28, 2009

(86) PCT No.: PCT/US2009/058598
§ 371 (c)(1), (2), (4) Date: Dec. 28, 2011

(87) PCT Pub. No.: WO2010/039649
PCT Pub. Date: Apr. 8, 2010

(65) Prior Publication Data
US 2012/0100574 A1    Apr. 26, 2012

Related U.S. Application Data

(60) Provisional application No. 61/195,088, filed on Oct. 3, 2008.

(51) Int. Cl.
*C12N 5/10* (2006.01)
*C12N 15/85* (2006.01)
(Continued)

(52) U.S. Cl.
CPC .......... *G01N 33/5767* (2013.01); *C07K 14/005* (2013.01); *C12N 2770/24144* (2013.01); *C12N 2770/24222* (2013.01); *C12N 2770/24243* (2013.01)

(58) Field of Classification Search
CPC ............. G01N 33/5767; C07K 14/005; C12N 2770/24243; C12N 2770/24144; C12N 2770/24222
See application file for complete search history.

(56) References Cited

U.S. PATENT DOCUMENTS 7,442,381 B2 * 10/2008 Smith et al. ................. 424/218.1
7,824,851 B2 * 11/2010 Sommadossi et al. ............ 435/5
(Continued)

OTHER PUBLICATIONS

Triyatni et al., A New Model to Produce Infectious Hepatitis C Virus without the Replication Requirement, Apr. 2011, vol. 7, Issue 4, e1001333.*

(Continued)

*Primary Examiner* — Reza Ghafoorian

(57) ABSTRACT

Provided herein is a mammalian cell transformed to contain a plasmid encoding a T7 or SP6 promoter operably linked to one or more HCV genes, a subgenomic replicon from a flavivirus and a cytoplasmic T7 and SP6 RNA amplification system. Also provided herein are isolated replication-competent HCV particles produced by the method comprising the steps of providing a transformed mammalian cell according to the first embodiment, culturing the cell, and recovering the replication-competent HCV particles from the cell culture. Provided herein are isolated HCV structural proteins produced by the method comprising the steps of providing a transformed mammalian cell according to the first embodiment, culturing the cell, and recovering the HCV structural proteins from the cell culture. Further provided herein is a system for assaying HCV entry into a cell comprising a first plasmid encoding a T7 or SP6 promoter operably linked to an HCV polynucleotide comprising at least the 5'-UTR to NS2 operably linked to an EMCV IRES in frame with an SP6 or T7 polymerase gene, respectively, a first host cell line expressing a replicon from a flavivirus and comprising a cytoplasmic T7 and SP6 RNA amplification system, a second plasmid encoding a reporter gene operably linked to both T7 and SP6 promoters in tandem, and a second host cell line comprising a cytoplasmic T7 polymerase or SP6 polymerase RNA amplification system.

22 Claims, 31 Drawing Sheets

(51) Int. Cl.
*G01N 33/68* (2006.01)
*C12Q 1/68* (2006.01)
*G01N 33/576* (2006.01)
*C07K 14/005* (2006.01)

(56) References Cited

U.S. PATENT DOCUMENTS

| | | | |
|---|---|---|---|
| 7,972,854 B2 * | 7/2011 | Miller et al. | 435/440 |
| 8,026,092 B2 * | 9/2011 | Lemon et al. | 435/235.1 |
| 2004/0029279 A1 * | 2/2004 | Kovacs et al. | 435/456 |
| 2010/0209454 A1 * | 8/2010 | Wimmer et al. | 424/205.1 |
| 2012/0100574 A1 * | 4/2012 | Saunier et al. | 435/69.1 |

OTHER PUBLICATIONS

Lohmann et al., Replication of Subgenomic Hepatitis C Virus RNAs in a Hepatoma Cell Line, Science Jul. 2, 1999: vol. 285 No. 5424 pp. 110-113.*

Elroy-Stein et al., Gene Expression Using the Vaccinia Virus/T7 RNA Polymerase Hybrid System, Current Protocols in Protein Science (1998) 5.15.1-5.15.11.*

Ali et al., Cell-Free Replication of the Hepatitis C Virus Subgenomic Replicon, Journal of Virology, Dec. 2002, p. 12001-12007.*

Blight et al., HCV Replicon Systems, Hepatitis C Viruses: Genomes and Molecular Biology, Chapter 11, Tan SL, editor. Norfolk (UK): Horizon Bioscience; 2006.*

Fuerst et al., Eukaryotic transient-expression system based on recombinant vaccinia virus that synthesizes bacteriophage T7 RNA polymerase, Proc. Nati. Acad. Sci. USA vol. 83, pp. 8122-8126, Nov. 1986.*

Khromykh et al., Encapsidation of the Flavivirus Kunjin Replicon RNA by Using a Complementation System Providing Kunjin Virus Structural Proteins in trans, Journal of Virology, Jul. 1998, p. 5967-5977.*

Triyatni et al., A New Model to Produce Infectious Hepatitis C Virus without the Replication Requirement, PLoS Pathogens, Apr. 2011, vol. 7, Issue 4, e1001333.*

Khromykh et al., Subgenomic Replicons of the Flavivirus Kunjin: Construction and Applications, Journal of Virology, Feb. 1997, p. 1497-1505.*

Mason et al., Production and characterization of vaccines based on flaviviruses defective in replication, Virology. Aug. 1, 2006; 351(2): 432-443.*

Sturgess et al., Universal primers that amplify RNA from all three flavivirus subgroups, Virology Journal 2008, 5:16, 1-10.*

Herweijer et al., A Plasmid-Based Self-Amplifying Sindbis Virus Vector, Humangene Therapy 6:1161-1167 (Sep. 1995).*

* cited by examiner

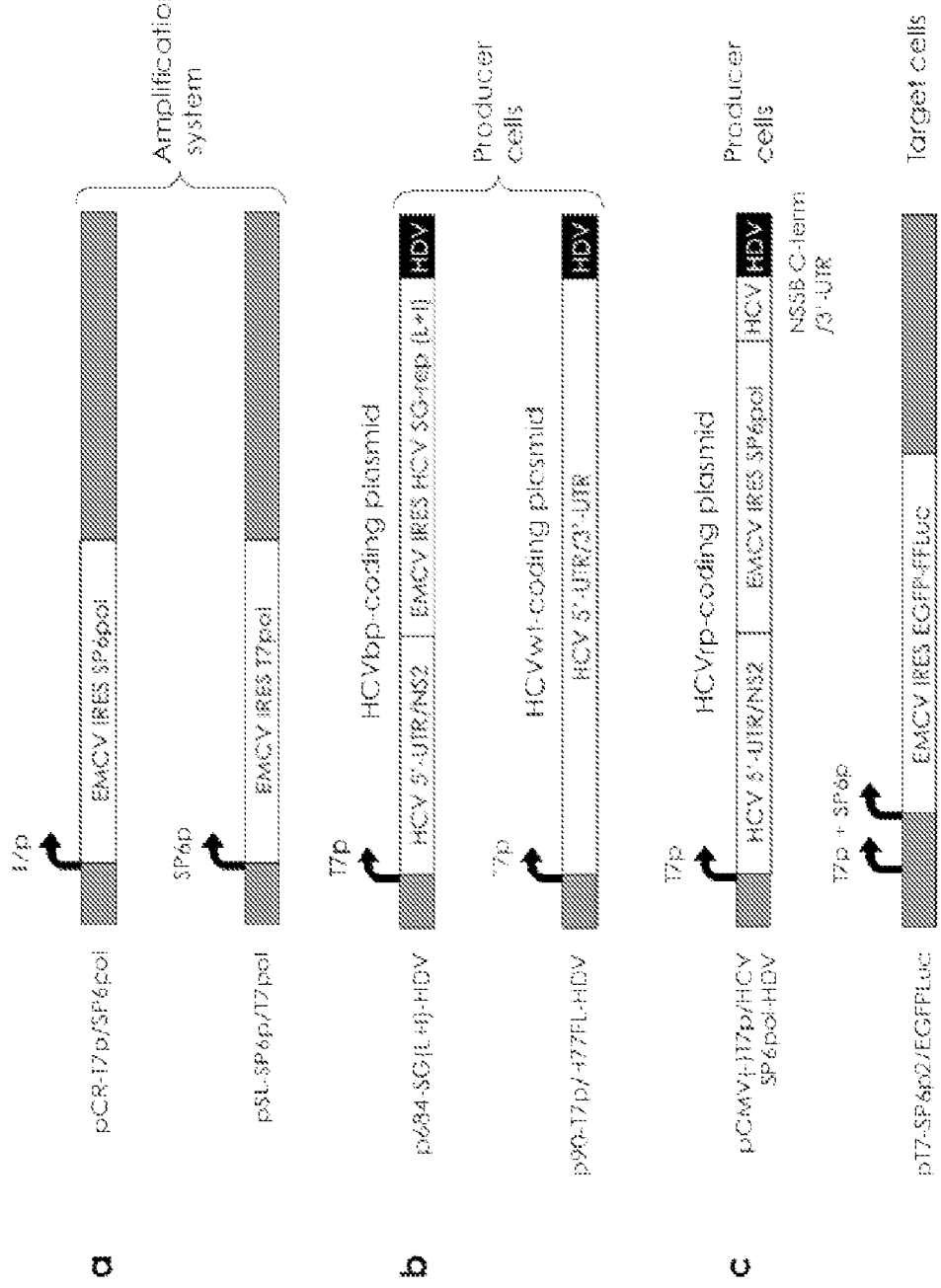

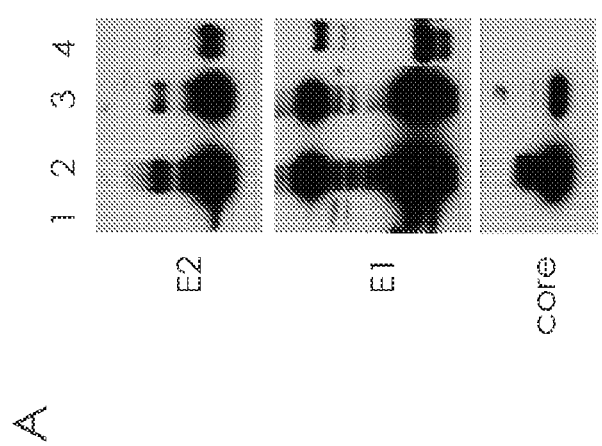

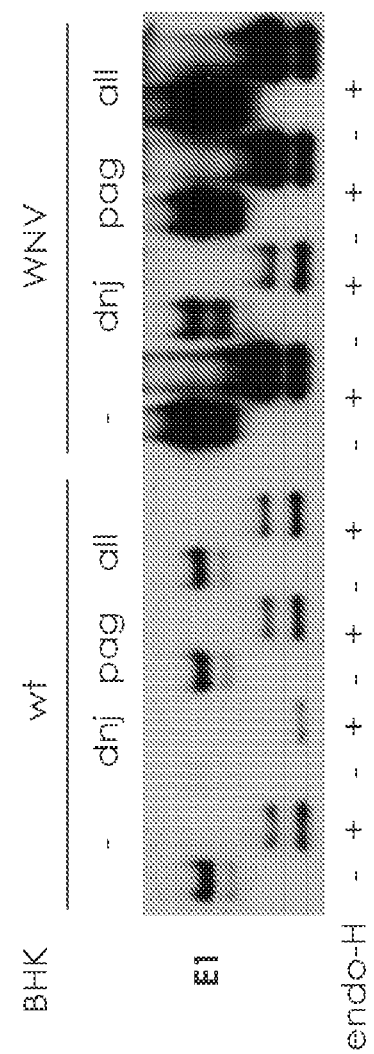

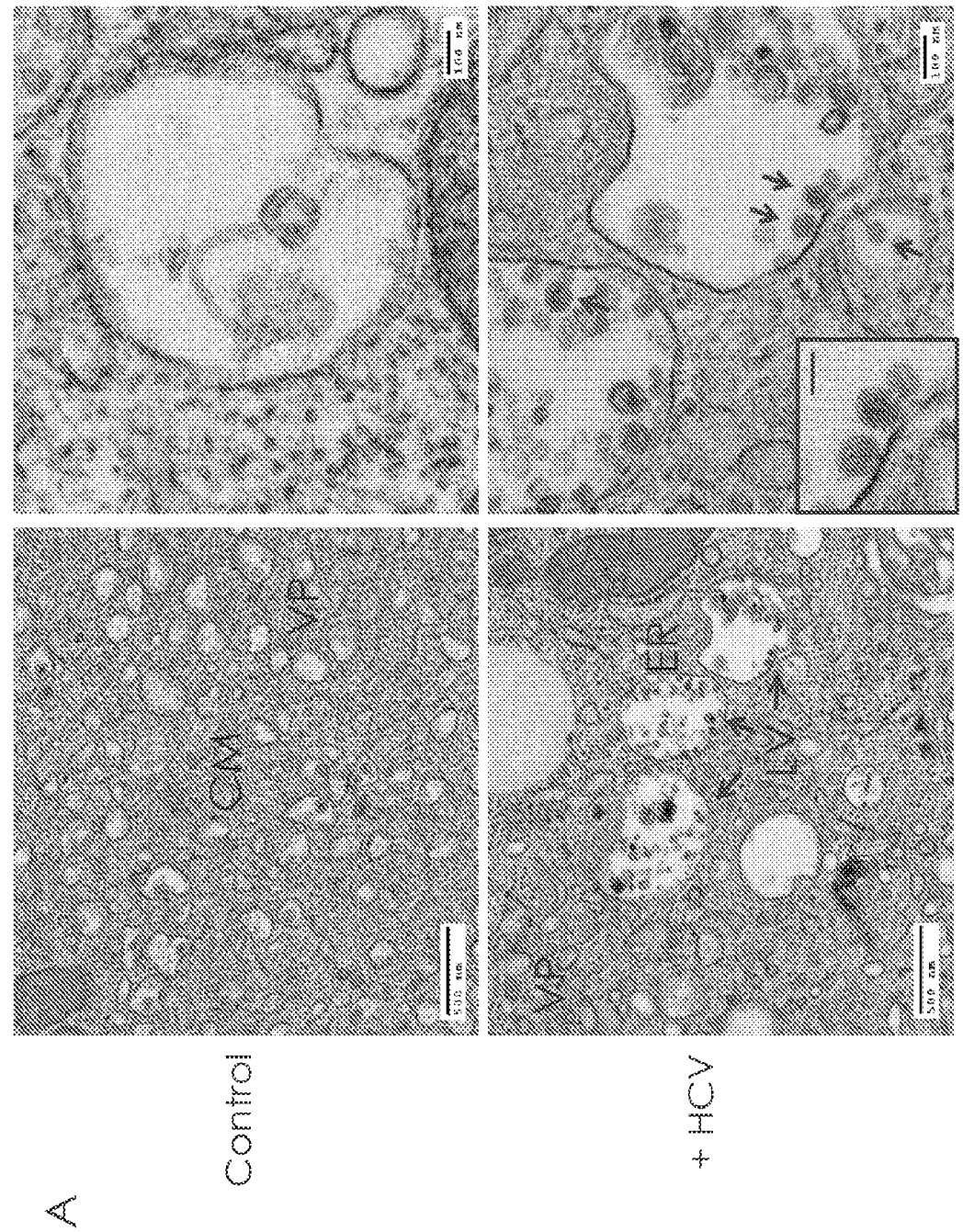

B

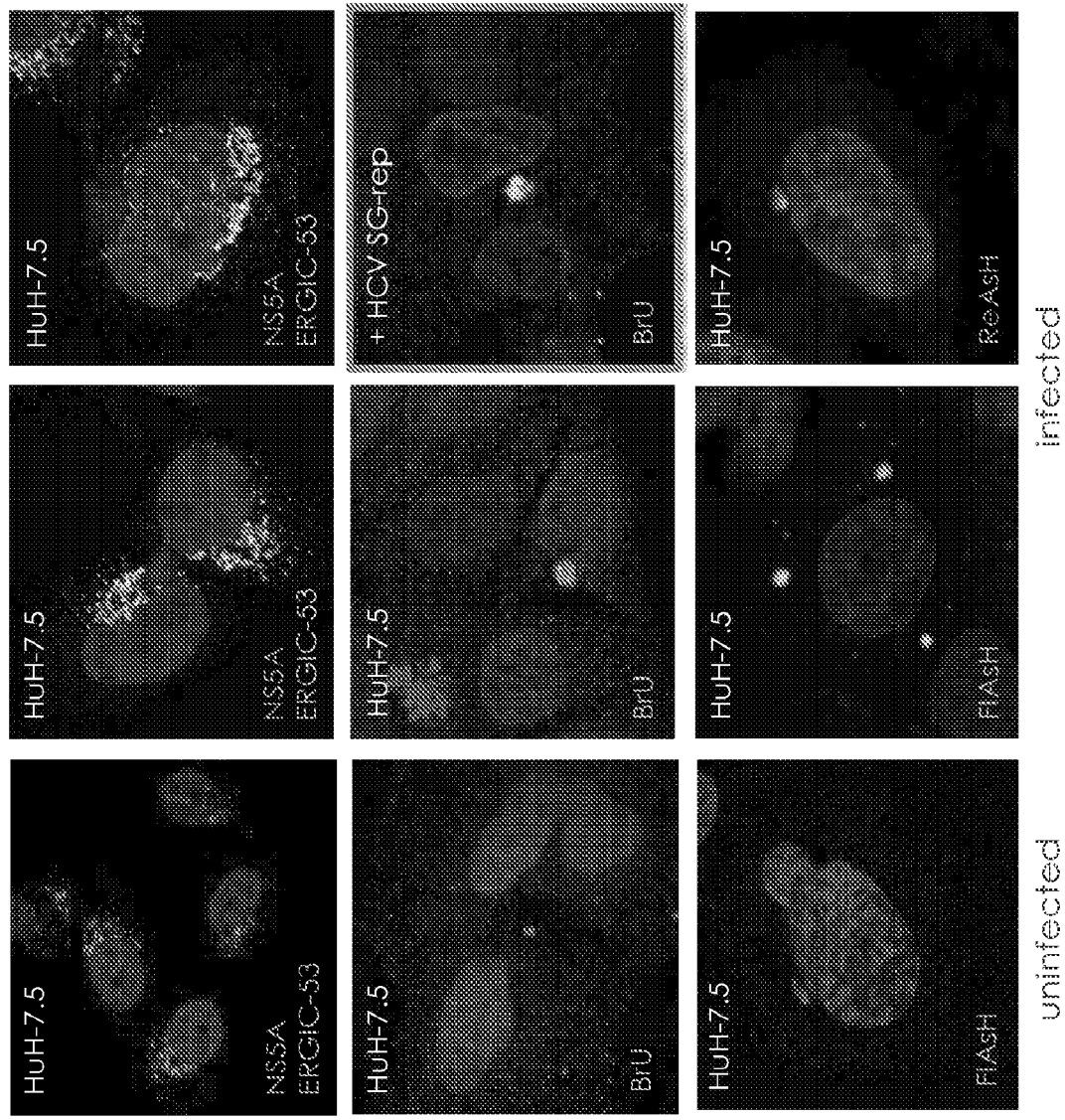

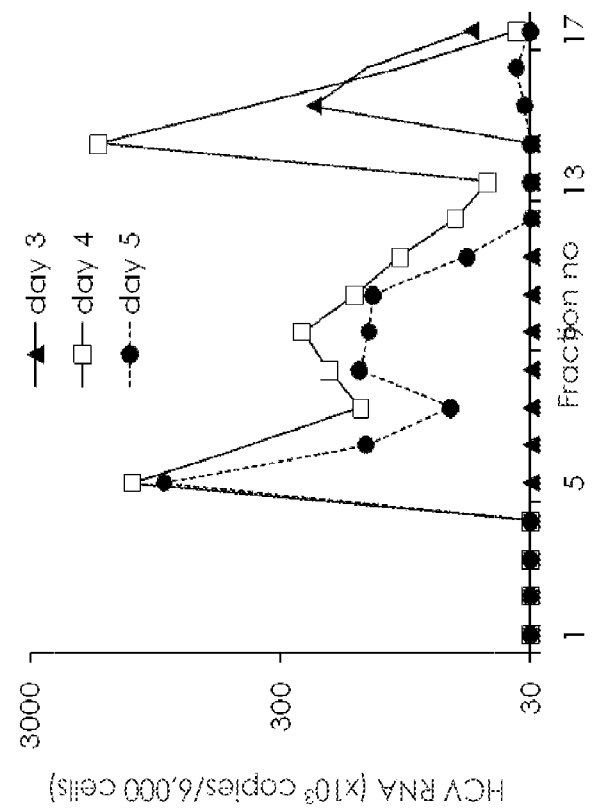

Figure 5B-C
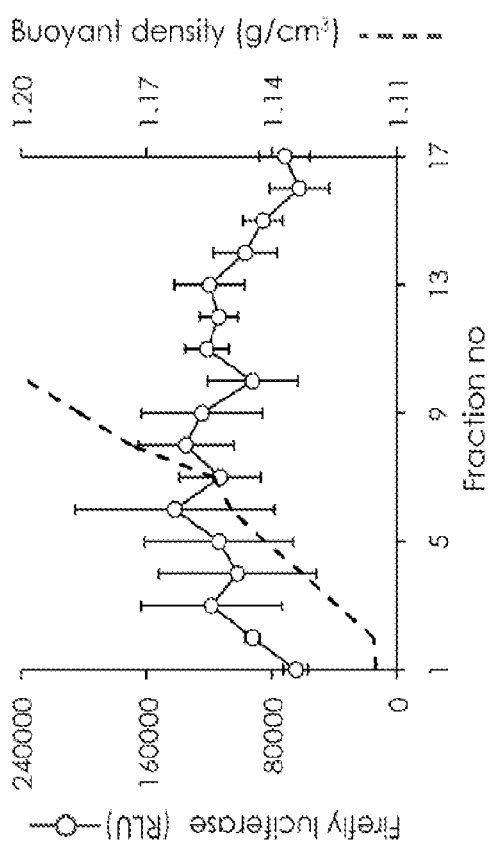
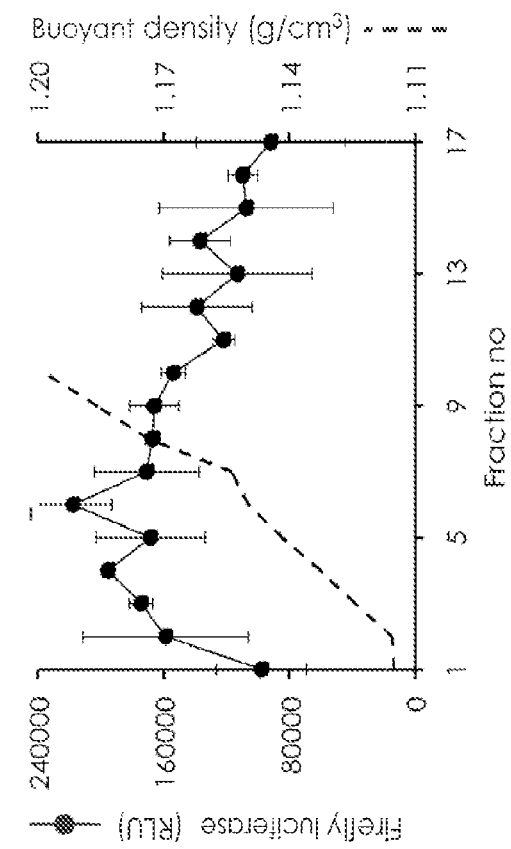

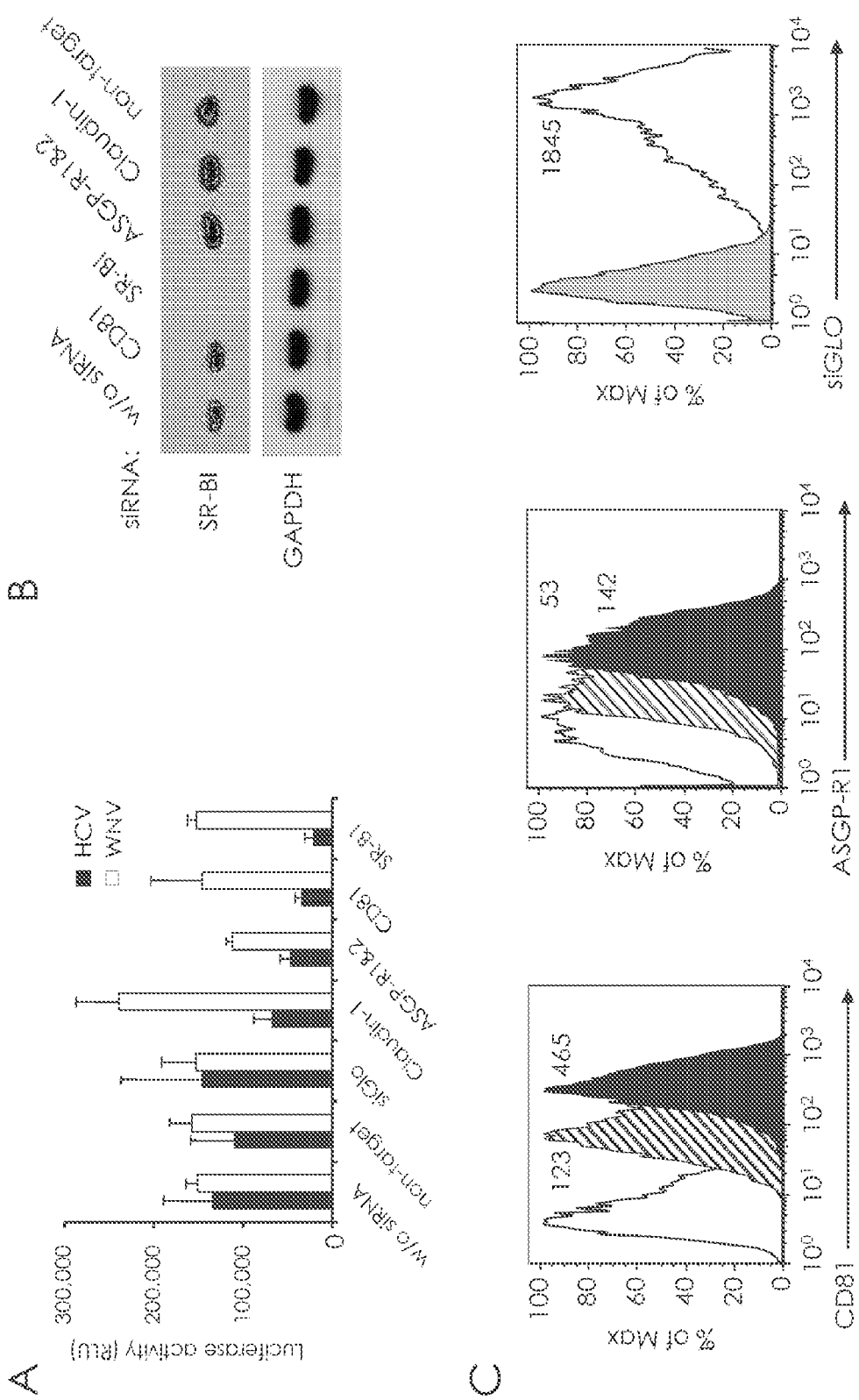
Figure 6A-C

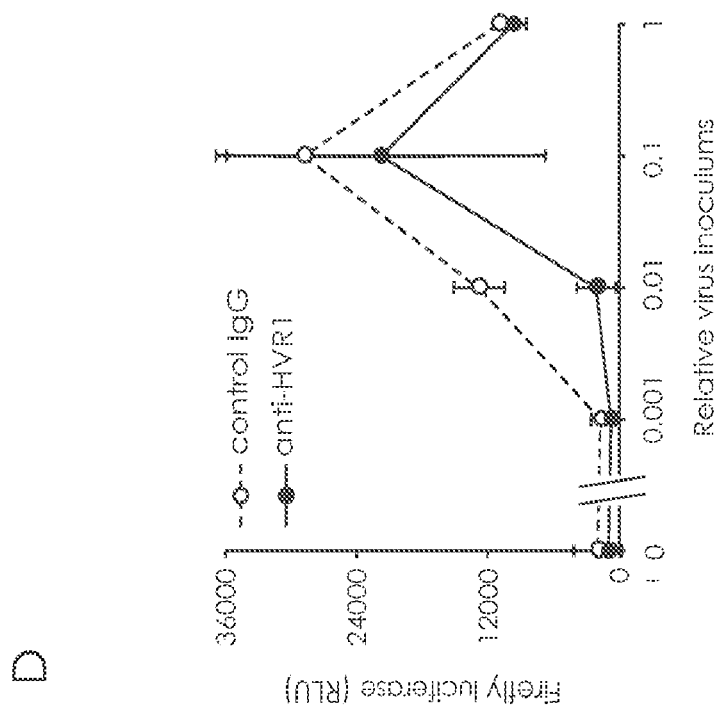
Figure 6D-E

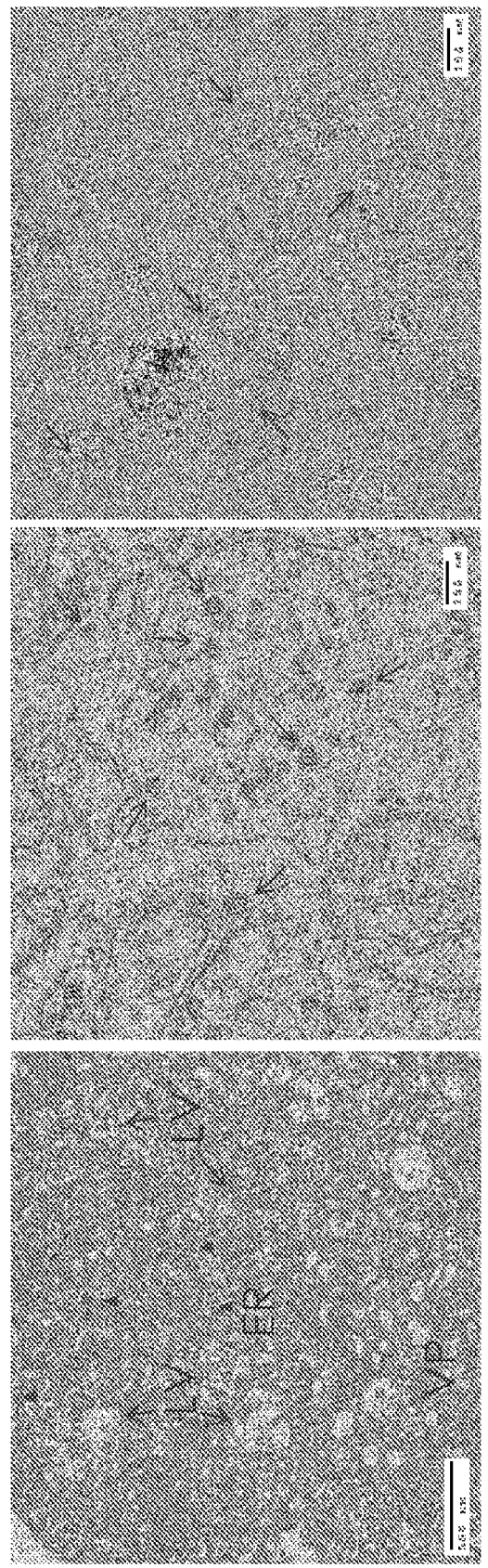

Figure 10A

BHK-WNV1 mRNA - - - - - → AAAAAAAAAAA
cDNA ══════════ TTTTTTTTTTT-AttB2-biot

2nd strand synthesis
+ AttB1 adaptor

AttB1 ◄══════ TTTTTTTTTTT-AttB2-biot
AttB1 ──────► AAAAAAAAAA-AttB2

BHK-WNV2.13

- - - - - - - - - - - → AAAAAAAAAAA
══════════ TTTTTTTTTTT

RNases H + A

TTTTTTTTTTT mix + heat denaturing + hybridization

×1

TTTTTTTTTTT-AttB2-biot
AAAAAAAAAA-AttB2

×3 or 10

TTTTTTTTTTT
TTTTTTTTTTT
AAAAAAAAAA-AttB2-biot

OR

AttB1 ◄══════
AttB1 ◄══════ streptavidin beads + recombinase cloning

AttB1 ◄══════
AttB1 ──────►

×2 rounds

BHK-WNV1-specific genes

Table 2. BHK-WNV1 transcripts identified after subtractive cloning with mRNA from BHK-WNV2.13 cells

| Gene name | # clones | Gene name | # clones |
|---|---|---|---|
| **Calnexin, variant 3, 2 *** | 10 | Ribosomal protein L6 | 4 |
| **Small EDRK-rich factor 2 *** | 3 | Ribosomal protein S12 | 4 |
| **Melanocortin 5 receptor *** | 2 | Cytochrome C oxidase chain 1 | 4 |
| **Tubulin alpha-4a *** | 1 | Ribosomal protein S28 | 1 |
| v-src homolog protein* | 1 | ATPase subunit 6 | 1 |
| Ryudocan (heparan sulfate proteoglycan core protein) | 1 | ATPase inhibitory factor 1 | 1 |
| Ubiquitin specific peptidase 33 | 1 | Mitochondrial transcript (?) | 1 |
| LRR-containing 58 | 1 | Unidentified short transcript (?) | 1 |

See differential screening strategy in Fig. 10A and protocol in Methods. * siRNA targeting calnexin (CANX), small EDRK-rich factor 2 (SERF2), melanocortin-5 receptor (MC5R), tubulin alpha-4A (TUBA4) and c-src knocked down their expressions; resulting effects on HCV production and release were tested (Fig. 10C).

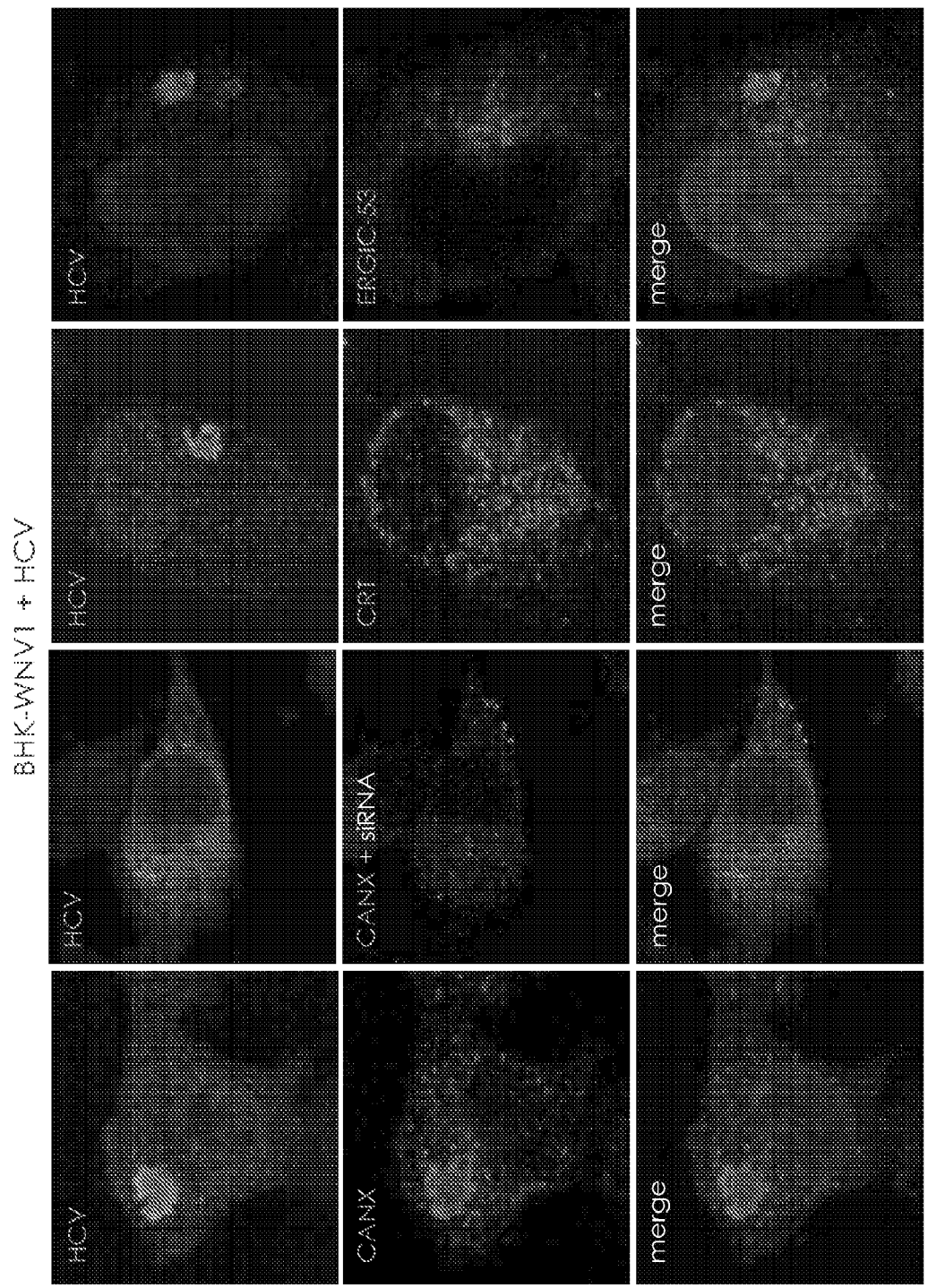

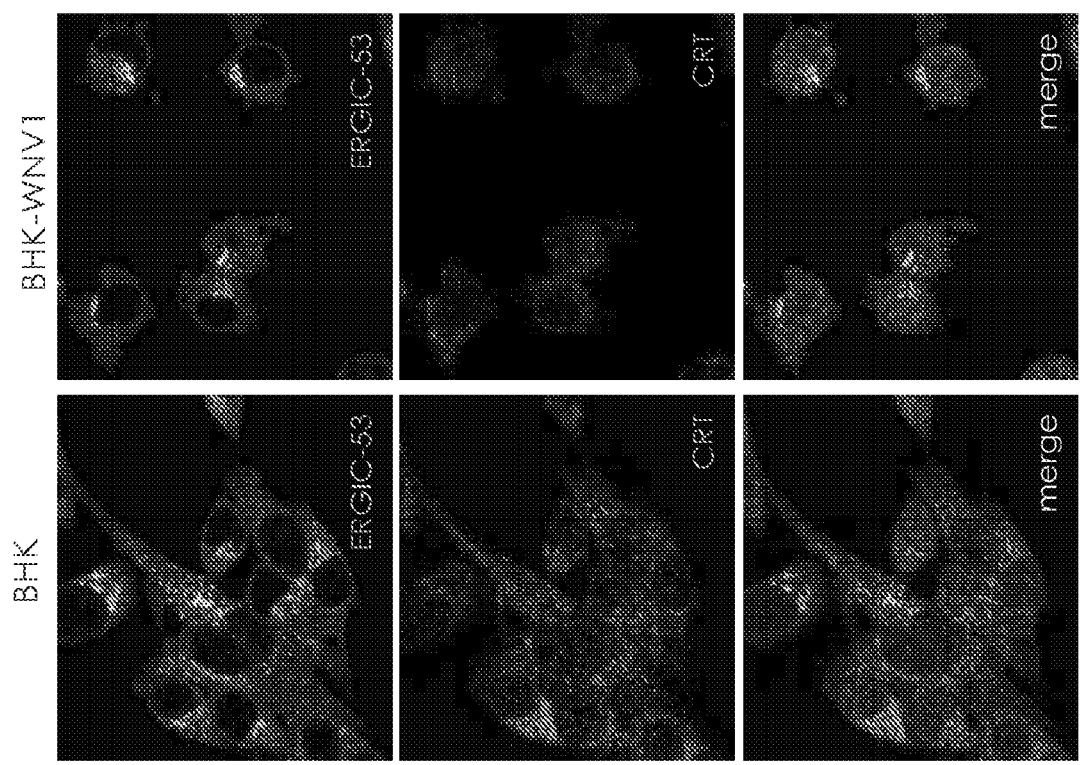

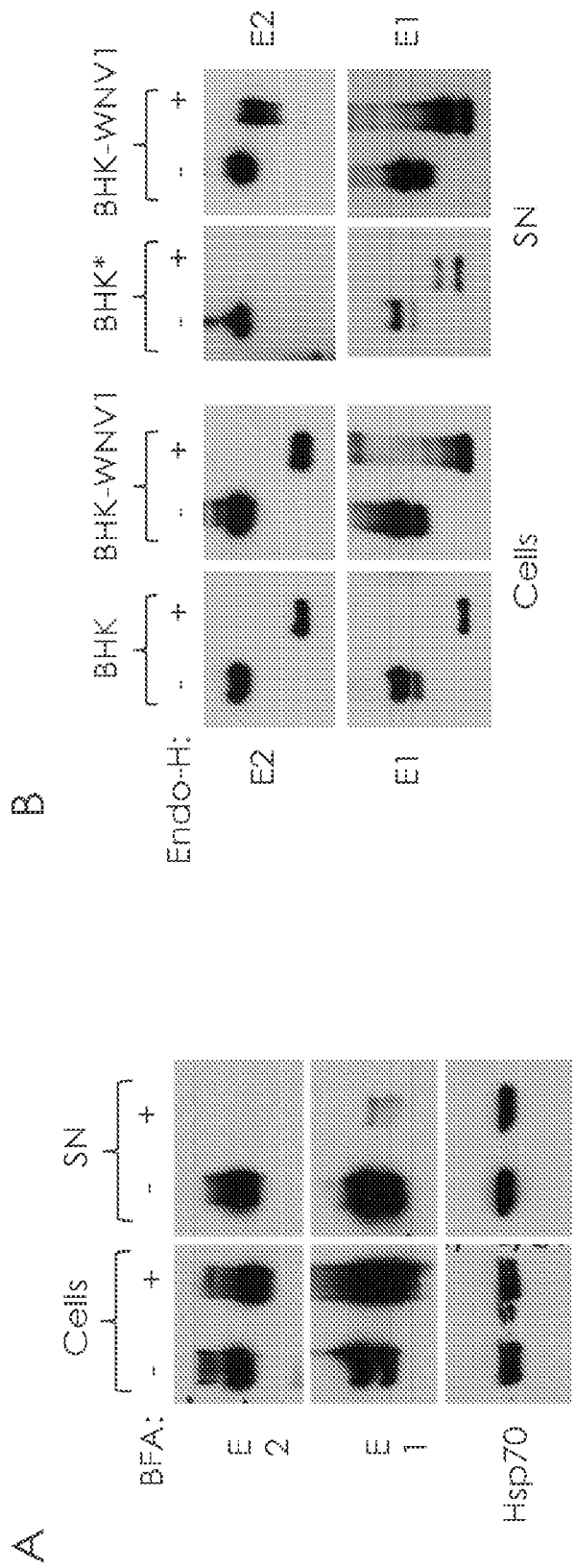
Figure 11A-B

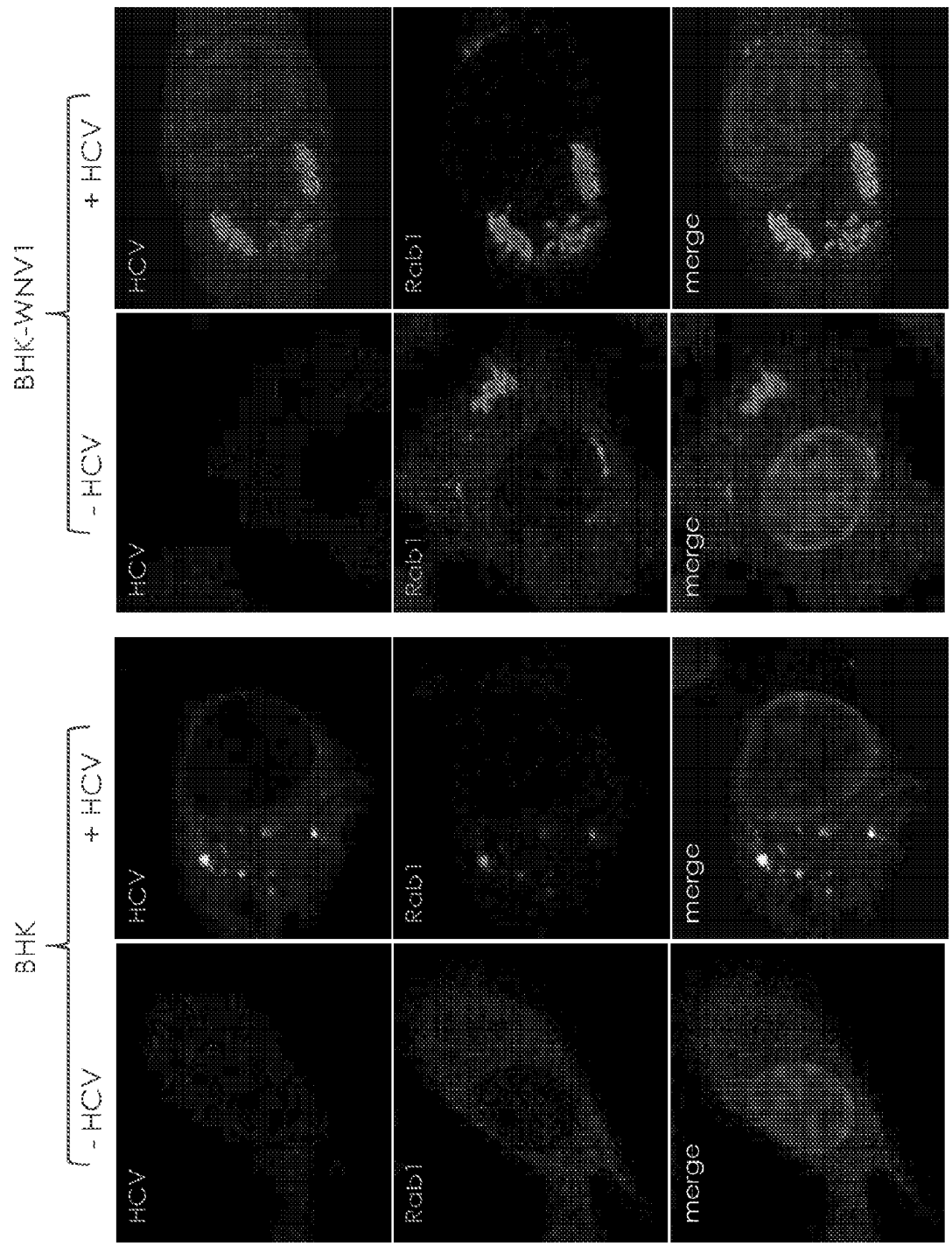

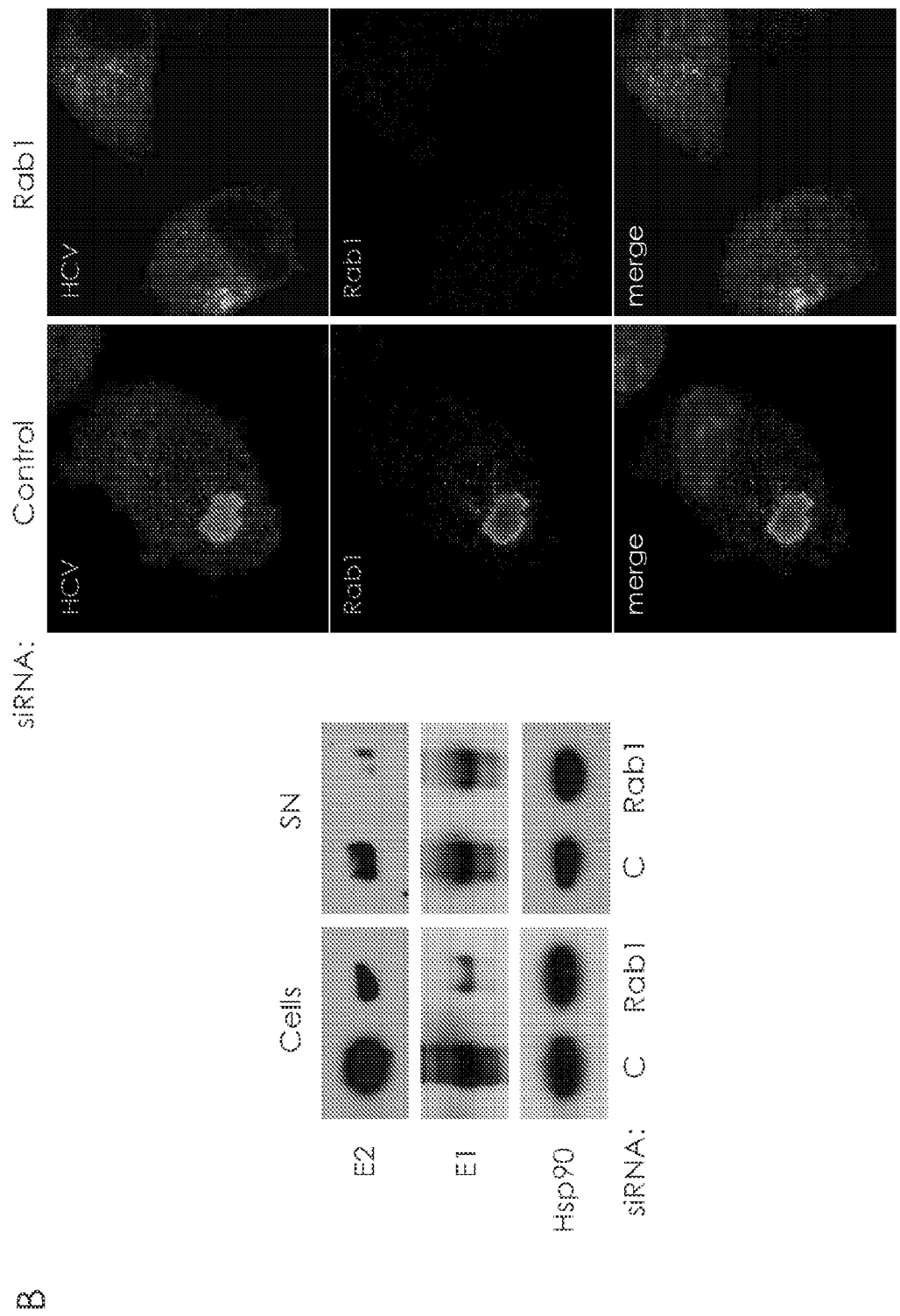

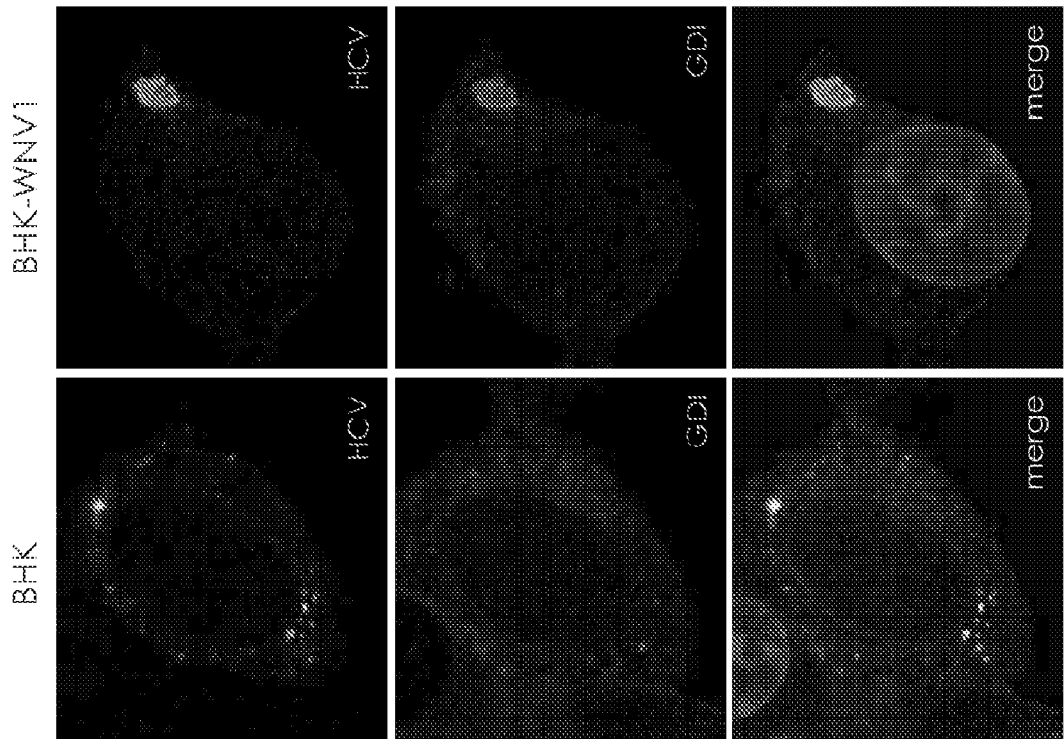

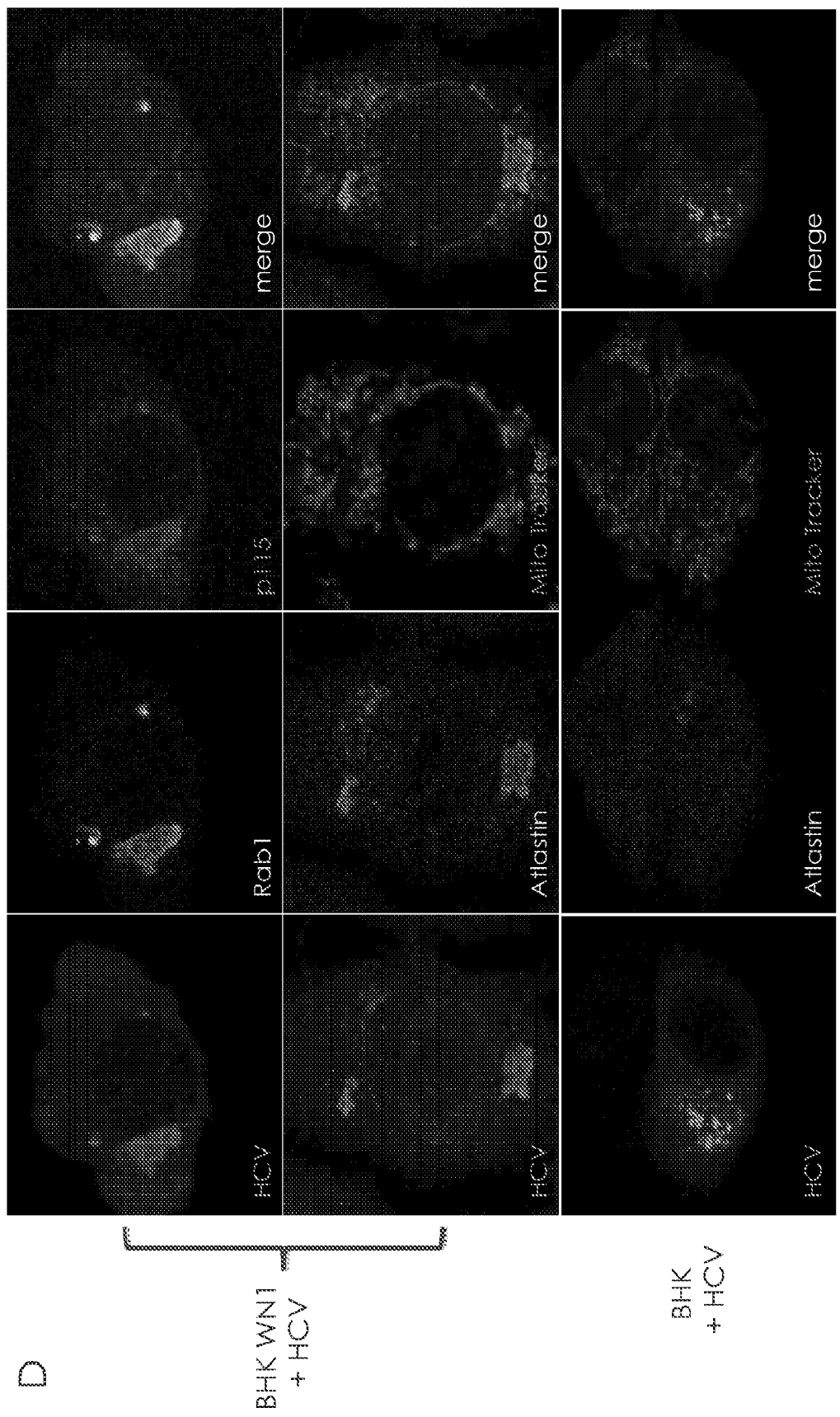

Figure 13A

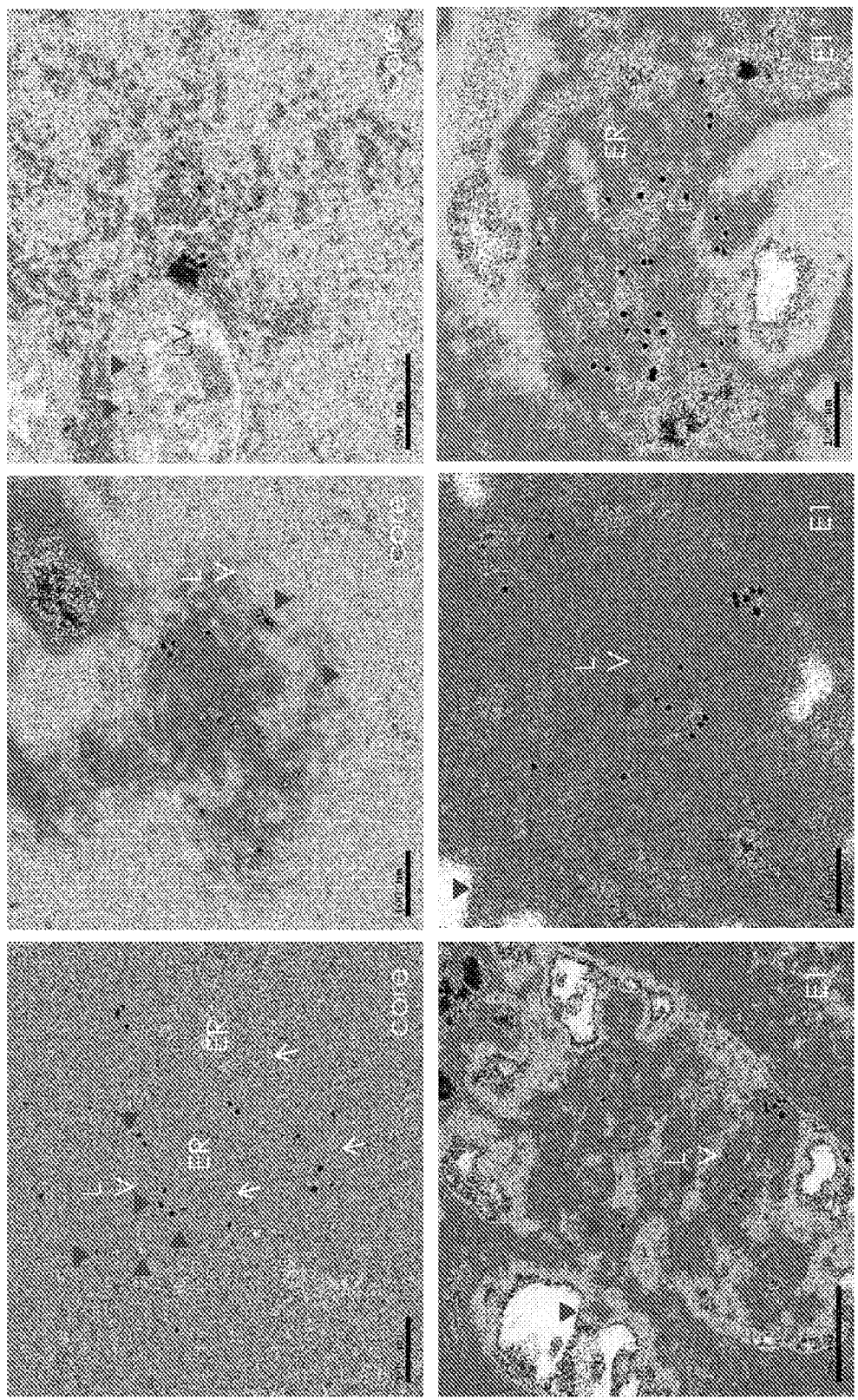

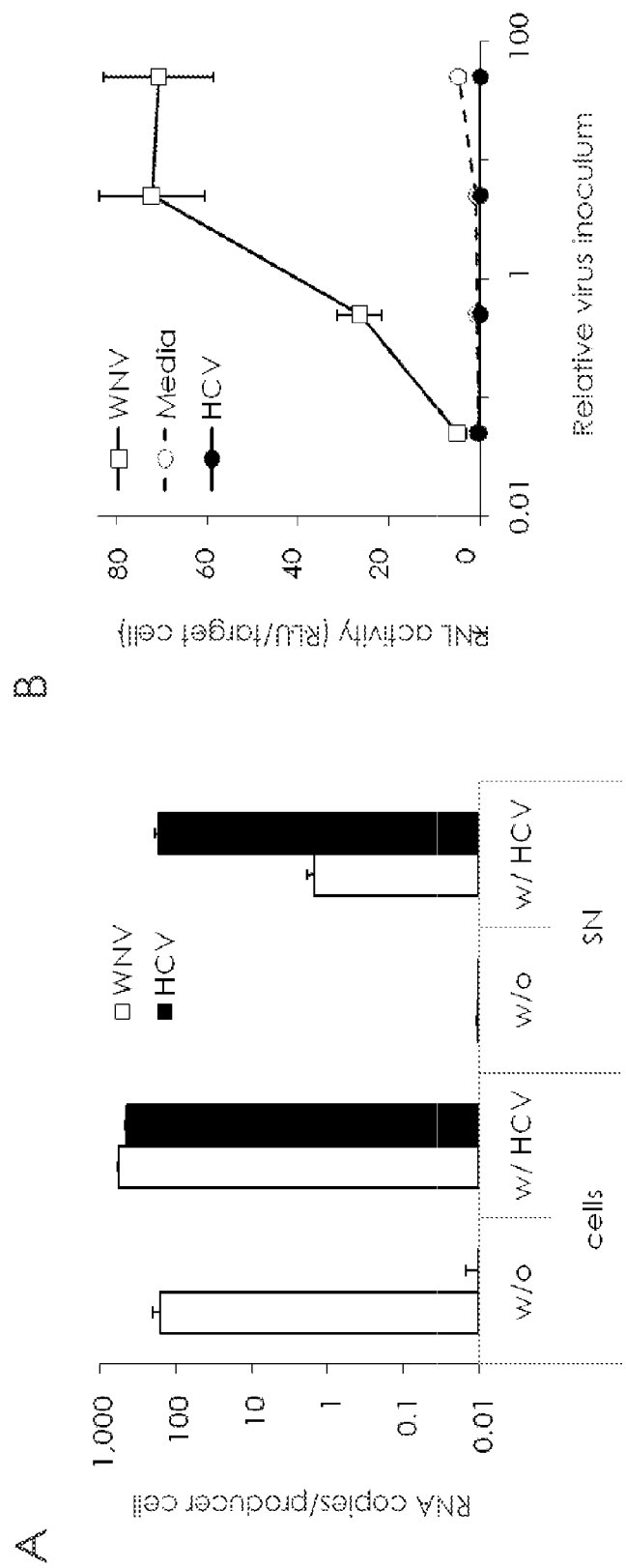
Figure 14A-B

US 9,052,321 B2

FLAVIVIRUS-BASED SYSTEM FOR PRODUCTION OF HEPATITIS C VIRUS (HCV)

STATEMENT OF FEDERALLY SPONSORED RESEARCH

This invention was made with Government support under Division of Intramural Research (DIR), NIAID, NIH.

CROSS-REFERENCE TO RELATED APPLICATIONS

This application is the national stage of PCT/US2009/058598, filed Sep. 28, 2009, which claims the benefit of priority to U.S. Provisional Application No. 61/195,088, filed Oct. 3, 2008, the disclosures of which are incorporated herein by reference in their entireties.

TECHNICAL FIELD

The present invention relates to systems and methods for producing hepatitis C virus (HCV) particles and structural proteins. It also relates to systems and methods for assaying HCV entry into a cell.

BACKGROUND

Hepatitis C virus (HCV) is a member of the hepacivirus genus in the Flaviviridae family and has infected 180 million people worldwide amongst whom 130 millions are chronic carriers at risk of developing liver cirrhosis or hepatocellular carcinoma. With an incidence of 3-4 million infections per year, HCV is responsible for 50-76% of all liver cancer cases and two thirds of all liver transplants in the developed world. The current standard of care, consisting of pegylated interferon-α2 combined with ribavirin, results in about 50% sustained virological response (Moradpour, D. et al., 2007. *Nat. Rev. Microbiol.* 5, 453-463). It is even less efficient against subtypes 1b and 1a, the two most prevalent in Europe and North America, respectively. (Manns, M. P. et al., 2007. *Nat. Rev. Drug Discov.* 6, 991-1000).

The virus replicates at a very rapid rate ($10^{12}$ virion/day) (Layden, T. J. et al., 2000. *Semin. Liver Dis.* 20, 173-183) and viral polymerase's lack of proofreading activity results in the emergence of viral quasispecies rapidly evolving with any kind of selective pressure. Several viral protease and polymerase inhibitors are now in the latter stages of clinical development and, despite their potent antiviral effects, have been complicated by the rapid selection of drug-resistance mutants (Thompson & McHutchison. 2009. *J. Viral Hep.* 2009. 16, 377-387). For similar reasons, there is no effective vaccine available yet, in vivo. Not surprisingly, antibody against hypervariable region 1 (HVR 1) of E2 failed to protect against the emergence of neutralization escape mutants (Farci, P. et al., 1996. *Proc. Natl. Acad. Sci. USA* 93, 15394-15399). In addition, serum antibodies from chronically HCV-infected individuals demonstrate broadly neutralizing properties in vitro and yet fail to control infection in vivo (Timpe, J. et al., 2008. *Hepatology* 47, 17-24). Anti-Envs antibodies have even been reported to enhance in vitro infectivity (Meyer, K. et al., 2008. *J. Virol.* 82, 2140-2149), as previously described for flaviviruses (e.g. West Nile (WN) and dengue viruses), or fail to inhibit cell-to-cell transmission (Timpe, J. M. et al., 2008. *Hepatology* 47, 17-24). Alternative antiviral strategies less prone to quickly select viral mutants are in high need; other steps of the HCV life cycle, such as cellular factors involved in viral production (assembly/release) and entry/genome uncoating, could represent such alternative.

HCV genomic RNA directly encodes an 3,000-amino-acid polyprotein that is processed by cellular as well as viral proteases. The first part of the genome encodes the structural proteins: core likely forms the nucleocapsid in viral particles (Yasui, K. et al., 1998. *J. Virol.* 72, 6048-6055) and E1, E2 envelope glycoproteins carry the fusogenic activities required for viral entry (Penin, F. et al., 2004. *Hepatology* 39, 5-19; Voisset, C., et al., 2004. *Biol. Cell.* 96, 413-420). p7 and NS2 are required for viral assembly and/or egress (Steinmann, E., F. et al., 2007. *PLoS Pathog* 3, e103; Jones, C. T. et al., 2007. *J. Virol.* 81, 8374-8383). The non-structural proteins NS3 to NS5B, together with 5'- and 3'-untranslated regions, support the viral replication (Lohmann, V. et al., 1999. *Science* 285, 110-113; Blight, K. J. et al., 2000. *Science* 290, 1972-1974). Soluble, truncated HCV E2 was used to identify cell surface binding molecules such as CD81 (Pileri, P. et al., 1998. *Science* 282, 938-941) and SR-BI (Scarselli, E. et al., 2002. *Embo J.* 21, 5017-5025) involved in HCV entry. Pseudotyping retrovirus with HCV envelope proteins, Bartosch et al (2003. *J. Exp. Med.* 197, 633-642) demonstrated that released particles (HCVpp) could enter target cells via CD81, SR-BI and claudin-1 (Evans, M. J. et al., 2007. *Nature* 446, 801-805) and occludin (Ploss, A. et al., 2009. *Nature* 457, 882-886)-dependent mechanisms. Lastly, a strain of genotype 2a (JFH-1; Kato, T. et al., 2001. *J. Med. Virol.* 64, 334-339) was identified reproducing a full infectious cycle in replication-permissive hepatocellular carcinomas cells in culture (Wakita, T. et al., 2005. *Nat. Med.* 11, 791-796; Zhong, J. et al., 2006. *J. Virol.* 80, 110892-11093).

There remains a need for a system for production of HCV particles that may be employed with multiple genotypes. There also remains a need for a method of uncoupling viral entry from its replication in order to specifically study the interactions of viral envelopes with target cell surface molecules and their involvement in internalization mechanisms. This method theoretically will also allow studying HCV production steps (translation, assembly and egress) and their mechanisms without interference from viral RNA replication. In essence, this method could lead to the identification of cellular factors that are specifically involved in HCV assembly and egress.

SUMMARY

Provided herein is a mammalian cell transformed to contain a plasmid encoding a T7 or SP6 promoter operably linked to one or more HCV genes, a subgenomic replicon from a flavivirus and a cytoplasmic T7 and SP6 RNA amplification system.

Also provided herein are isolated replication-competent HCV particles produced by the method comprising the steps of providing a transformed mammalian cell as described supra, culturing the cell, and recovering the replication-competent HCV particles from the cell culture.

Also provided herein are isolated HCV structural proteins produced by the method comprising the steps of providing a transformed mammalian cell as described supra, culturing the cell, and recovering the HCV structural proteins from the cell culture.

Further provided herein are systems for assaying HCV particle entry into a cell comprising a first plasmid encoding a T7 (or SP6) promoter operably linked to an HCV polynucleotide comprising at least the 5'-untranslated region (UTR) to NS2 operably linked to an encephalomyocarditis virus (EMCV) internal ribosome entry site (IRES) in frame with an SP6 (or T7, in the case of an SP6 promoter) polymerase gene, a first host cell line expressing a subgenomic replicon from a flavivirus and comprising a cytoplasmic T7 and SP6 RNA amplification system, a second plasmid encoding a reporter gene operably linked to both T7 and SP6 promoters in tandem, and a second host cell line comprising a cytoplasmic T7 polymerase or SP6 polymerase RNA amplification system. Preferably, the system utilizes a T7 promoter operably linked to HCV 5'-UTR to NS2 operably linked to an EMCV IRES in frame with an SP6 polymerase gene. In another embodiment, the SP6 promoter is operably linked to HCV 5'-UTR to NS2 operably linked to an EMCV IRES in frame with a T7 polymerase gene.

Still further provided herein are methods for assaying HCV particle entry into a cell. The system described supra for assaying HCV particle entry into a cell is provided. HCV particles produced by the first host cell line are collected. The second host cell line is incubated with the HCV particles produced by the first host cell line. Expression of the reporter gene is then measured, wherein expression of the reporter gene is proportional to HCV particle entry. Preferably, the system utilizes a T7 promoter operably linked to HCV 5'-UTR to NS2 operably linked to an EMCV IRES in frame with an SP6 polymerase gene. In another embodiment, the SP6 promoter is operably linked to HCV 5'-UTR to NS2 operably linked to an EMCV IRES in frame with a T7 polymerase gene.

Also provided herein are methods for identifying cellular proteins necessary for HCV particle entry into the host cell. The system described supra for assaying HCV particle entry into a cell is provided. HCV particles produced by the first host cell line are collected. A second host cell is transfected with siRNA targeting a cellular protein, and this second host cell line is incubated with the HCV particles produced by the first host cell line. Expression of the reporter gene is then measured, wherein expression of the reporter gene is proportional to HCV particle entry, and wherein a decrease in viral entry indicates that the cellular protein targeted by the siRNA is a cellular protein necessary for HCV particle entry into the host cell.

This application also discloses other methods for identifying cellular proteins necessary for HCV particle entry into the host cell. The system described supra for assaying HCV particle entry into a cell is provided. HCV particles produced by the first host cell line are collected. A second plasmid encoding a reporter gene operably linked to both T7 and SP6 promoters in tandem is provided. The second plasmid is expressed in a second host cell line comprising a cytoplasmic T7 polymerase or SP6 polymerase RNA amplification system. The second host cell line is transfected with a plasmid encoding a promoter operably linked to a candidate protein gene. The second host cell line is incubated with the HCV particles produced by the first host cell line, and expression of the reporter gene is measured, wherein expression of the reporter gene is proportional to HCV particle entry, and wherein an increase in viral entry indicates that the candidate protein is a cellular protein necessary for HCV particle entry into the host cell.

This application also discloses methods for identifying cellular proteins necessary for HCV particle entry into the host cell. The system described supra for assaying HCV particle entry into a cell is provided. HCV particles produced by the first host cell line are collected. The second host cell line is transduced with a recombinant lentivirus expressing a candidate protein gene. The second host cell line is incubated with the HCV particles produced by the first host cell line, and expression of the reporter gene is measured, wherein expression of the reporter gene is proportional to HCV particle entry, and wherein an increase in viral entry indicates that, depending on its location, the candidate protein is a cellular receptor for, or another cellular protein favoring HCV particle entry.

The application is also directed to methods for identifying HCV glycoproteins that are necessary for HCV particle entry into the cell. The system described supra for assaying HCV particle entry into a cell is provided. HCV particles produced by the first host cell line are collected. The second host cell line is incubated with the HCV particles produced by the first host cell line. Expression of the reporter gene is measured, wherein expression of the reporter gene is proportional to HCV particle entry. Incubation of the HCV particles with antibody to a candidate HCV glycoprotein is performed prior to infection with the HCV particles. A decrease in HCV particle entry indicates that said HCV glycoprotein is necessary for HCV particle entry into the cell.

The application is also directed to methods for identifying test compounds effective at blocking HCV particle entry into the cells or viral genome uncoating. The system described supra for assaying HCV particle entry into a cell is provided. HCV particles produced by the first host cell line are collected. The second host cell line is incubated with the HCV particles produced by the first host cell line. Expression of the reporter gene is measured, wherein expression of the reporter gene is proportional to HCV particle entry or viral genome uncoating. Incubation of the second host cells with a test compound is performed prior to infection with the HCV particles, wherein a decrease in HCV particle entry indicates that said test compound is effective at blocking HCV particle entry or viral genome uncoating.

Still further provided herein are methods of identifying cellular factors that are involved in the release of infectious HCV particles by host cells expressing WNV subgenomic replicon. A clone of said host cell line that fails to produce infectious HCV particles is identified. cDNA from said clone is isolated. Two-round subtractive hybridization is then performed between cDNA from said host cell line and an excess of cDNA from said clone to isolate said host cell line specific genes encoding cellular factors that are involved in the release of infectious HCV particles. In preferred embodiments, the clone is BHK-WNV2.i and the host cell line is BHK-WNV1.

This application also discloses methods for identifying a test compound that inhibits HCV particle assembly, maturation and/or egress, or genome packaging. The system described supra for assaying HCV particle production by measuring their entry in a target cell is provided. The first host cell line is incubated with a test compound. Any HCV particles produced by the first host cell line are collected. The second host cell line (target cell) is incubated with the HCV particles produced by the first host cell line, and expression of the viral proteins, genomic RNA replication, particle forming unit (infectious titer), with or without trans-complementation (cf. below), and/or reporter gene is measured, wherein expression of those is proportional to HCV particle assembly, maturation and/or egress, or genome packaging in said first host cell line, and wherein a decrease in viral entry (as measured above) indicates that said test compound inhibits HCV particle assembly, maturation and/or egress, or genome packaging.

Also provided herein are methods for studying the contribution of HCV structural proteins to viral spreading. A cell according to the first embodiment is provided wherein the plasmid encodes a T7 or SP6 promoter operably linked to an HCV full-length bi-cistronic genome wherein HCV nonstructural proteins are expressed from an EMCV IRES and HCV structural proteins are expressed from the HCV IRES. A second host cell line is incubated with the HCV particles produced by the first cell and is transfected with a second plasmid encoding a promoter operably linked to one or more HCV structural proteins. The production of infectious HCV particles containing the bi-cistronic RNA is measured, wherein an increase in the production of infectious HCV particles containing the bi-cistronic RNA indicates that said one or more HCV structural proteins assist in producing infectious HCV particles.

Also provided herein are methods for studying the contribution of candidate HCV non-structural proteins to viral production through their involvement in viral assembly or egress. A cell according to the first embodiment is provided wherein the plasmid encodes a T7 or SP6 promoter operably linked to an HCV construct wherein one or more HCV structural proteins are expressed from an HCV IRES and one or more candidate HCV non-structural proteins are expressed from a EMCV IRES. The production of infectious HCV particles containing the bi-cistronic RNA is measured, wherein an increase in the production of infectious HCV particles containing the bi-cistronic RNA indicates that said one or more candidate HCV non-structural proteins assist in producing infectious HCV particles through their involvement in viral assembly or egress.

Also provided herein are methods for producing infectious HCV containing wild type full-length genome without adaptive mutations. A cell according to the first embodiment is provided wherein the plasmid is constructed encoding a T7 or SP6 promoter operably linked to an HCV full-length wild type genome wherein HCV proteins are expressed from an HCV IRES. HCV particles containing the full-length wild type genome RNA are then recovered from the cell culture.

Also provided is a method for studying viral spreading and dissemination in an organ, tissue and/or animal. A cell according to the first embodiment is provided, wherein the plasmid encodes a T7 or SP6 promoter operably linked to a full-length HCV genome that has been engineered to encode a tetracysteine (TC) tag. The cell is cultured, and tagged HCV particles produced by the cell are collected. A target organ, tissue or animal is incubated or exposed to the tagged HCV particles. The target organ, tissue or animal is incubated with biarsenical dyes. The spread of the tagged HCV particles is studied in the target organ, tissue or animal, wherein fluorescence of the biarsenical dyes indicates the presence of the TC tag. In preferred embodiments, the TC tag is in a non-structural gene.

The cell described in the first embodiment can also be used in methods for identifying cellular factors that are involved in the release of HCV particles by host cells expressing WNV subgenomic replicon. BHK-WNV1 cells are provided and are transfected with a plasmid encoding siRNA directed to a target candidate cellular protein. The cells are also transfected with a plasmid encoding HCV. HCV release by the cells is quantified, wherein a decrease in HCV release indicates that the candidate cellular protein is involved in the release of HCV particles.

The cell described in the first embodiment can also be used in methods for identifying cellular proteins involved in viral assembly, maturation or egress. A candidate protein that is a connecting partner of a previously identified cellular protein involved in viral assembly, maturation or egress is identified through bioinformatic analysis. BHK-WNV1 cells are provided and are transfected with a plasmid encoding siRNA directed to said candidate connecting partner. The cells are also transfected with a plasmid encoding HCV. Viral assembly, maturation or egress is quantified in the cells, wherein a decrease in viral assembly, maturation or egress indicates that the candidate protein is involved in HCV assembly, maturation or egress.

The cell described in the first embodiment can also be used in methods for assaying HCV particle entry into a cell. A cell according to the first embodiment is provided. HCV particles produced by the cell are collected, and a second host cell line is incubated with the HCV particles produced by the first cell. The presence of viral proteins or viral RNA in the second host cell line is measured, wherein the presence of viral proteins or viral RNA in the second host cell line is proportional to HCV particle entry.

The cell described in the first embodiment can also be used in methods for identifying cellular proteins necessary for HCV particle entry into the host cell. A cell according to the first embodiment is provided. HCV particles produced by the first cell are collected. A second host cell line is transfected with siRNA targeting a cellular protein. The second host cell line is incubated with the HCV particles produced by the first cell. The presence of viral proteins or viral RNA in the second host cell line is measured, wherein the presence of viral proteins or viral RNA in the second host cell line is proportional to HCV particle entry, and wherein a decrease in viral entry indicates that the cellular protein targeted by the siRNA is a cellular protein necessary for HCV particle entry.

Another use for the cell described in the first embodiment is in methods for identifying cellular proteins necessary for HCV particle entry into the host cell. A cell according to the first embodiment is provided. HCV particles produced by the first cell are collected. A second host cell line is transfected with a plasmid encoding a promoter operably linked to a candidate protein gene. The second host cell line is incubated with the HCV particles produced by the first cell. The presence of viral proteins or viral RNA in the second host cell line is measured, wherein the presence of viral proteins or viral RNA in the second host cell line is proportional to HCV particle entry, and wherein an increase in viral entry indicates that the candidate protein is a cellular protein necessary for HCV particle entry.

The cell described in the first embodiment can also be used in other methods for identifying cellular proteins necessary for HCV particle entry into the host cell. A cell according to the first embodiment is provided. HCV particles produced by the first cell are collected. A second host cell line is transduced with a recombinant lentivirus expressing a candidate protein gene. The second host cell line is incubated with the HCV particles produced by the first cell line. The presence of viral proteins or viral RNA in the second host cell line is measured, wherein the presence of viral proteins or viral RNA in the second host cell line is proportional to HCV particle entry, and wherein an increase in viral entry indicates that the candidate protein is a cellular protein necessary for HCV particle entry.

Another use for the cell described in the first embodiment is in methods for identifying HCV glycoproteins that are necessary for HCV particle entry into the cell. A cell according to the first embodiment is provided. HCV particles produced by the first cell are collected. A second host cell line is incubated with the HCV particles produced by the first cell line. The presence of viral proteins or viral RNA in the second host cell line is measured, wherein the presence of viral proteins or viral RNA in the second host cell line is proportional to HCV particle entry, and incubating the HCV particles with antibody to a candidate HCV glycoprotein is performed prior to infection with the HCV particles, and wherein a decrease in HCV particle entry indicates that the candidate HCV glycoprotein is necessary for HCV particle entry into the cell.

The cell described in the first embodiment can also be used in other methods for identifying test compounds effective at blocking HCV particle entry into the cells or viral genome uncoating. A cell according to the first embodiment is provided. HCV particles produced by the first cell are collected. A second host cell line is incubated with the HCV particles produced by the first cell line. The presence of viral proteins or viral RNA in the second host cell line is measured, wherein the presence of viral proteins or viral RNA in the second host cell line is proportional to HCV particle entry or viral genome uncoating. The second host cells are incubated with a test compound prior to infection with the HCV particles, wherein a decrease in HCV particle entry or viral genome uncoating indicates that the test compound is effective at blocking HCV particle entry or viral genome uncoating.

The cell described in the first embodiment can also be used in other methods for identifying cellular factors that are involved in the release of infectious HCV particles by host cells expressing WNV subgenomic replicon. A cell according to the first embodiment is provided. HCV particles produced by the first cell are collected. A second host cell line is incubated with the HCV particles produced by the first cell. The presence of viral proteins or viral RNA is measured in the second host cell line, wherein the presence of viral proteins or viral RNA in the second host cell line is proportional to HCV particle entry. A clone of the first cell that fails to produce HCV particles capable of entering the second host cell line is identified. cDNA is isolated from the clone and two-round subtractive hybridization is performed between first cell transcriptome under the form of double-stranded cDNA and an excess of cDNA from the clone, wherein first cell-specific genes are isolated. In preferred embodiments, the clone is BHK-WNV2.i and the first cell is BHK-WNV1.

The cell described in the first embodiment can also be used in other methods for identifying a test compound that inhibits HCV particle assembly, maturation, egress or genome packaging. A cell according to the first embodiment is provided. The first cell is incubated with a test compound. HCV particles produced by the first cell are collected. A second host cell line is incubated with the HCV particles produced by the first cell. The presence of viral proteins or viral RNA is measured in the second host cell line, wherein the presence of viral proteins or viral RNA in the second host cell line is proportional to HCV particle assembly, maturation and/or egress or genome packaging in the first cell, and wherein a decrease in viral entry indicates that the test compound inhibits HCV particle assembly, maturation, egress or genome packaging.

BRIEF DESCRIPTION OF THE DRAWINGS

FIG. 1 illustrates constructs to produce HCV and HCV-like particles. Production of recombinant plasmids in *E. coli* in which a bacteriophage DNA-dependent RNA polymerase (DdRp) expression is under the control of its own cognate promoter (referred to as autogenes) are highly unstable and results in low yields and high mutation rates. We designed a new system to amplify the cytoplasmic transcription of plasmids in which the gene of interest is under the control of a DdRp's cognate promoter; this system consists of a set of two plasmids generating T7 polymerase (FIG. 1a): A) Amplification system to produce T7 and Sp6 RNA polymerase: i) pCR-T7p/SP6pol in which bacteriophage SP6 DdRp (SP6pol) open reading frame was cloned into pCR2.1 plasmid (Invitrogen) in frame with the second ATG start codon of EMCV IRES under the control of T7 promoter; it) pSL-SP6p/T7pol in which bacteriophage T7 DdRp (T7pol) open reading frame was cloned into pSL1180 plasmid (Clontech) in frame with the second ATG start codon of EMCV IRES under the control of SP6 promoter. Upon stimulation, the two plasmids cross-amplify each other's transcription; the leakiness of the system is favorable for a stronger expression of HCV proteins in the producer cells, but it is purposely reduced in target cells by adding low concentrations of actinomycin D. This system of plasmids was used for all T7 promoter-driven HCV coding plasmids, in which a sequence coding for an HDV antigenomic ribozyme (Wadkins, T. S., & Been, M. D. 2002. *Cell. Mob Life Sci.* 59, 112-125) was added at their C termini. As a consequence, all HCV transcripts were uncapped and have correct 3'-ends. We used p90 HCVconFLlongpU plasmid (Kolykhalov, A. A. et al., 1997. *Science* 277, 570-574) plus or minus cell-culture adaptive mutations (Blight, K. J. et al., 2003. *J. Virol.* 77, 3181-3190) as templates to construct all HCV coding plasmids. B) Production of full-length HCV bicistronic particles (HCVbp) and HCV wild-type (HCVwt): HCVbp was produced from p684-SG(L+I)-HDV plasmid (FIG. 1b) in which the neomycin resistance gene in H-Neo-SG(L+I) construct (Blight, K. J. et al., 2003., *J. Virol.* 77, 3181-3190) was replaced with HCV structural gene sequence (5'-UTR to NS2) between the T7 promoter and EMCV IRES. T7 polymerase is driving the cytoplasmic transcription of this plasmid from its cognate promoter and the transcripts are, therefore, uncapped. To produce HCV-wt i.e. HCV particles containing the full-length, consensus sequence of H77 strain from p90-T7p/H77FL-HDV plasmid (FIG. 1b), we introduced a HDV antigenomic ribozyme at the 3'-end of p90HCVconFLlongpU. C) Production of bicistronic HCV-reporter particles (HCVrp) and reporter system: HCVrp was produced from pCMV(−)T7p/HCV-SP6pol-HDV plasmid (FIG. 1c) that encodes HCV 5'-UTR and structural genes followed by those of bacteriophage SP6 DNA-dependent RNA polymerase (entry signal) gene in frame with EMCV IRES and a sequence encoding carboxy-terminus of HCV NS5B (kissing loops) (Friebe, P., et al., 2005. *J. Virol.* 79, 380-392) and 3'-UTR. To detect incoming-SP6pol RNA upon HCVrp entry into target cells, pT7-SP6p2/EGFPLuc reporter plasmid was made (FIG. 1c). This plasmid was derived from pEGFPLuc plasmid (Clontech) in which EMCV-IRES-EGF-PLuc expression is under the control of both bacteriophage T7pol and SP6pol cognate promoters in tandem. This construct lacks eukaryotic promoter and therefore is responsive either to T7pol, SP6pol, or both; it was found responding to either incoming DdRp protein or encoding RNA (data not shown). The reporter plasmid is transfected with the amplification system (A) in target cells following their infection.

FIG. 11 illustrates that secretion of HCV particles involves maturation of HCV glycoproteins in Golgi apparatus: A) Twelve hours after transfection of BHK-WNV1 cells with pHCVp7, cells were treated with 20 µM brefeldin-A (BFA) for 24 hours and the amounts of HCV E1 and E2 proteins in cell lysates and released particles were analyzed by WB; Hsp70=control. B) BHK and BHK-WNV1 cells were transfected with pHCVp7. Three days later, cells and particles in SN were harvested and treated with endo-H, followed by WB analysis. *, 30 ml culture media was used for parental BHK cells (15 ml for BHK-WNV1 cells).

FIG. 12 illustrates the release of HCV particles by BHK-WNV1 cells requires Rab1 in a specific cytoplasmic subcompartment. A) Three days after transfection of BHK-21 or BHK-WNV1 cells with plasmid encoding HCVbp, IF was performed with anti-HCV serum and anti-Rab1 antibody, followed by confocal microscopy analysis. B) (left) BHK-WNV1 cells treated with Rab1 siRNA were transfected with HCVbp-coding plasmid. Cells and SN were harvested 3 days later, and analyzed by WB; Hsp90=control. (right) BHK-WNV1 cells treated with Rab1 siRNA (or not) were transfected with HCVbp-coding plasmid. IF was performed three days later as above. C-D), Three days after transfection of BHK-WNV1 cells with HCVbp-coding plasmid, IF was performed with anti-HCV serum and anti-GDI-α (C), or, anti-Rab1, -p115, and -Atlastin-1 antibodies (D). Mitochondria were labeled with Mito Tracker Orange CMTMRos.

FIG. 14 illustrates that HCV particles do not trans-encapsidate WNV SG-rep. A) Upon transfection of BHK-WNV1 cells with HCVbp-coding plasmid [p684-SG(L+I)-HDV], WNV and HCV RNA were extracted from cells and pelleted supernatants (SN) and were analyzed by RT-qPCR; a similar protocol was used for non-transfected cells. Represented RNA copies originated from the same number of producer cells, for both cells and SN, are shown. B) BHK-WNV1 cells were transfected with either p684-SG(L+I)-HDV, pIRES1hyg-WNV (cf. Method) or mock plasmid. SN were harvested 3 days later; particles were pelleted, resuspended in complete medium, serially diluted and incubated with HuH-7.5 cells for 2 hr; cells were further grown for 48 hr and RNL activity was measured in cell lysates.

DETAILED DESCRIPTION OF ILLUSTRATIVE EMBODIMENTS

Figure 2B:
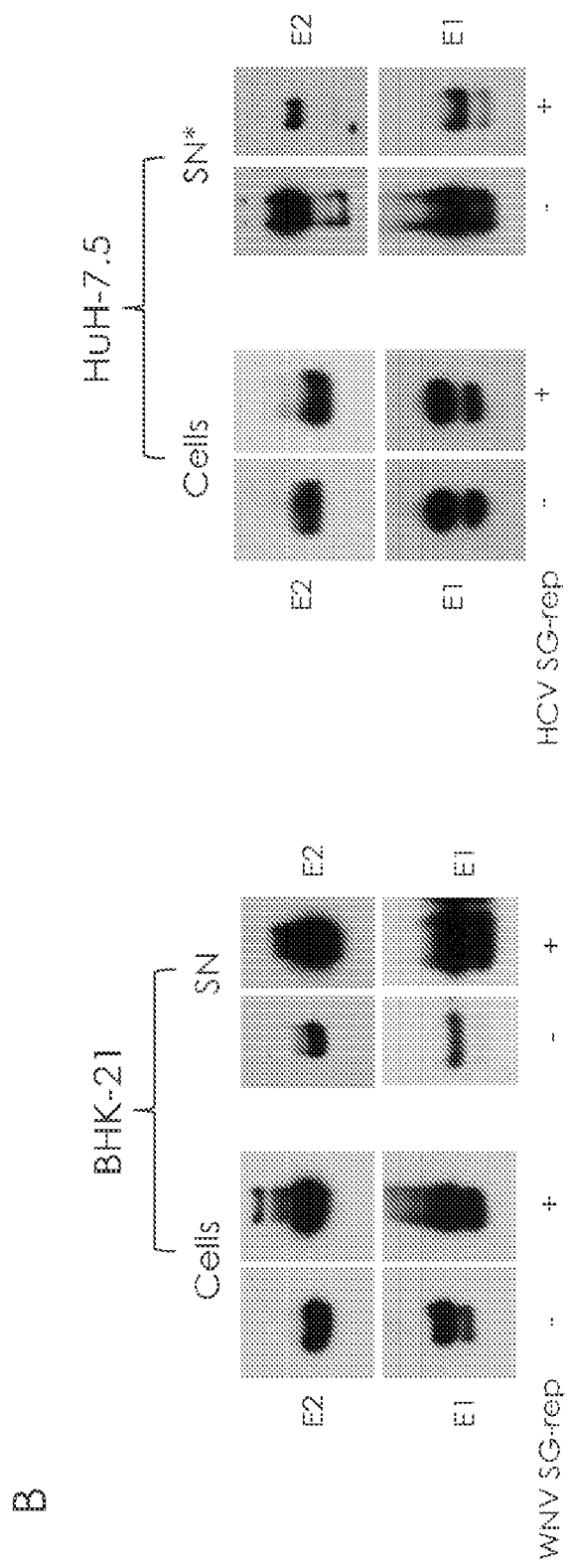
FIG. 2 illustrates factors affecting the release of HCV structural proteins: A) Enhancement by flavivirus, but not alphavirus subgenomic, replicons in BHK-21 cells: BHK-21 parental cells (lane 1) or bearing WNV1 (lane 2), Den2 (lane 3) or Semliki Forest virus SG-replicon (lane 4) were transfected with pHCVp7 (plasmid encoding HCV core to p7). Three days later, clarified culture media were pelleted over 15% sucrose cushion, then pellets were analyzed by Western blot with the following monoclonal antibodies: i) anti-HCV E2: AP33; ii) anti-HCV E1: A4, and iii) anti-HCV core: C1. B) WNV- and HCV-SG rep differentially affect the release of HCV-like particles. (left) BHK-21 cells, parental or bearing WNV1 SG-rep, were transfected with HCVp7, a plasmid encoding HCV core to p7. Three days later, HCV proteins in the lysate and supernatants (SN) were analyzed by Western Blot (WB). (right) HuH-7.5 cells (parental or harboring HCV 1a SG-rep) transfected with the same plasmid, were analyzed by WB. *, the E1/E2 signals were obtained with 60 ml of culture media instead of 15 ml for BHK parental and -WNV1 cells. C) N-glycosylation but not O-glycosylation is required for the release of HCV particles: BHK cells were transfected with pHCVp7, then treated or not with 3 mM deoxynojirimycin (dnj), 3 mM phenyl acetyl galactosaminide (pag) or 0.3 mM alloxan (all) for 2 days; HCV E1 Envelope released by BHK-21 parental or BHK-WNV1 cells was analyzed by Western blot after incubation with or without endoglycosidase H (endo-H).

Various terms relating to aspects of the description are used throughout the specification and claims. Such terms are to be given their ordinary meaning in the art unless otherwise indicated. Other specifically defined terms are to be construed in a manner consistent with the definitions provided herein.

All references cited herein are incorporated by reference in their entirety and for all purposes.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "promoter" as used herein describes minimal sequence sufficient to direct transcription. Also included in the definition are those promoter elements which are sufficient to render promoter-dependent gene expression controllable for cell-type specific, tissue-specific or inducible by external signals or agents; such elements may be located in the 5' or 3' regions of the native gene.

The term "operably linked" as used herein describes when a gene and one or more regulatory sequences are connected in such a way as to permit gene expression when the appropriate molecules (e.g., transcriptional activator proteins) are bound to the regulatory sequences.

The term "reporter gene" as used herein describes a gene whose expression may be assayed. Such genes include, without limitation, green fluorescent protein (GFP), enhanced green fluorescent protein (EGFP), glucuronidase (GUS), luciferase, firefly luciferase (FFL), chloramphenicol transacetylase (CAT), and β-galactosidase.

The term "transformed cell" as used herein describes a cell into which (or into an ancestor of which) has been introduced, by means of recombinant DNA techniques, a DNA molecule.

The term "transformation" as used herein describes any method for introducing foreign molecules into cells. Examples of transformation include, without limitation, lipofection, calcium phosphate precipitation, retroviral delivery, electroporation and biolistic transformation.

The term "replicon" as used herein describes a segment of DNA, when encoded sequence is under the form of a plasmid, or a single stranded positive RNA with correct 5' and 3' termini (e.g. capped in 5' for flaviviruses, but not for pesti- or hepaciviruses that have an IRES) that, upon translation, encodes all proteins required for its own replication in the cytoplasm of permissive cells; a replicon also encodes the proteins required for its production (assembly and egress). If the replicon is missing one or more genes required for its production (generally structural genes), it is referred to as subgenomic replicon. A selection (e.g. blasticidin) and/or a reporter (e.g. Renilla luciferase) gene is often added in place of removed viral genes, for example a plasmid, that can replicate independently. The term "sub-genomic flavivirus replicon" as used herein describes segment of DNA comprising sub-genomic sequences derived from a flavivirus. In some embodiments, the sub-genomic flavivirus replicon has had one or more structural genes removed and further expresses an antibiotic selection gene and a Renilla luciferase (RNL) gene marker. (See Pierson, T. et al., 2006. Virology 346, 53-65).

The term "test compound" as used herein comprises modified and unmodified antibodies, antibody fragments, proteins, glycosylated proteins or pharmaceutical compounds.

The term "substractive hybridization" as used herein is a technology that allows for PCR-based amplification of only cDNA fragments that differ between a control and experimental transcriptome. The technique relies on the removal of dsDNA formed by hybridization between a control and test sample, thus eliminating cDNAs or genomic DNAs of similar abundance, and retaining differentially expressed, or variable in sequence, transcripts or genomic sequences. (Diatchenko L, et al., 1996. Proc. Natl. Acad. Sci. USA 93 (12), 6025-6030).

It is to be understood that the embodiments described herein are not limited to particular methods, reagents, compounds, compositions or biological systems, which can, of course, vary. It is also to be understood that the terminology used herein is for the purpose of describing particular promoter or reporter gene sequences only, and is not intended to be limiting.

Provided herein is a mammalian cell transformed to contain a plasmid encoding a T7 or SP6 promoter operably linked to one or more HCV genes, a subgenomic replicon from a flavivirus and a cytoplasmic T7 and SP6 RNA amplification system. In preferred embodiments, the one or more HCV genes comprise an HCV full-length bi-cistronic genome. In other embodiments, the one or more HCV genes comprise an HCV full-length wild type genome. In further embodiments, the one or more HCV genes comprise one or more HCV structural proteins or one or more HCV non-structural proteins. In certain preferred embodiments, the one or more HCV structural proteins are selected from C, E1 or E2. In other preferred embodiments, the one or more HCV non-structural proteins are selected from p7 or NS5B.

Also provided is the recombinant mammalian cell according to any one of the preceding embodiments wherein the host cell line is a BHK-21 stable cell line or a HuH-7.5 stable cell line. In other embodiments, the recombinant mammalian cell may be any human hepatic cell, including other hepatic cell lines, fetal cell lines, primary cells, liver slices or other organotypic liver culture or bioreactor.

Also provided is the recombinant mammalian cell according to any one of the preceding embodiments wherein the flavivirus is West Nile virus or dengue virus. In further embodiments, the replicon also expresses an antibiotic selection gene, preferably blasticidin, and a Renilla luciferase (RNL) gene marker.

Provided herein is a mammalian cell transformed to contain a plasmid encoding a T7 or SP6 promoter operably linked to an HCV full-length bi-cistronic genome, a subgenomic replicon from a flavivirus and a cytoplasmic T7 and SP6 RNA amplification system. In preferred embodiments, the HCV full-length bi-cistronic genome is of genotype 1a. In other embodiments, the HCV full-length bi-cistronic genome is of any one of genotypes 1 to 6/7 or their subtypes, mutated and/or engineered, or not, provided they encode a RNA sequence with correct 5' and 3' ends and encoding genes required for viral production. In other embodiments, the HCV full-length bi-cistronic genome is operably linked to a hepatitis delta antisense ribozyme at the 3' end. In further embodiments, the HCV full-length bi-cistronic or wild type genome has been tagged with a tetracysteine (TC)-tag.

Further provided is the recombinant mammalian cell according to any one of the preceding embodiments wherein the one or more HCV genes are isolated from a HCV recovered from a patient. Also provided is the recombinant mammalian cell according to any one of the embodiments wherein the HCV genotype is 1a.

Further provided is the recombinant mammalian cell according to any one of the embodiments wherein the cytoplasmic T7 polymerase or SP6 polymerase RNA amplification system comprises a plasmid encoding a T7 polymerase promoter operably linked to an EMCV IRES in frame with the SP6 polymerase open reading frame, and a plasmid encoding an SP6 polymerase promoter operably linked to an EMCV IRES in frame with the T7 polymerase open reading frame.

Provided is a method for producing an HCV structural protein or replication-competent HCV particles comprising the steps of providing a recombinant mammalian cell according to any one of the preceding embodiments, culturing the cells, and recovering the HCV structural protein or replication-competent HCV particles from the cell culture. In preferred embodiments, the recovered HCV structural protein or replication-competent HCV particles are produced without HCV virus replication. In other preferred embodiments, the HCV particles or structural proteins are purified by passing them through a sucrose cushion or gradient. In further preferred embodiments, the HCV particles or structural proteins are purified by passing them through a filter for purifying and concentrating them.

Also provided herein are isolated replication-competent HCV particles produced by the method comprising the steps of providing a transformed mammalian cell as described in the first embodiment, culturing the cell, and recovering the replication-competent HCV particles from the cell culture.

Provided herein are isolated HCV structural proteins produced by the method comprising the steps of providing a transformed mammalian cell as described in the first embodiment, culturing the cell, and recovering the HCV structural proteins from the cell culture.

System for Assaying HCV Particle Entry into a Cell.

Provided herein is a system for assaying HCV particle entry into a cell comprising a first plasmid encoding a T7 (or SP6) promoter operably linked to an HCV polynucleotide comprising at least the 5'-UTR to NS2 operably linked to an EMCV IRES in frame with an SP6 (or T7, in the case of an SP6 promoter) polymerase gene, a first host cell line expressing a replicon from a flavivirus and comprising a cytoplasmic T7 and SP6 RNA amplification system, a second plasmid encoding a reporter gene operably linked to both T7 and SP6 promoters in tandem, and a second host cell line comprising a cytoplasmic T7 polymerase or SP6 polymerase RNA amplification system. In preferred embodiments, the host cell line is a BHK-21 stable cell line or a HuH-7.5 stable cell line or other HCV-permissive target cell line. In other embodiments, the second host cell line is incubated with actinomycin D. Actinomycin D blocks RNA-polymerase II-dependent transcription in the nucleus. In further embodiments, the reporter gene is Enhanced Green Fluorescent Protein (EGFP) fused with Firefly luciferase (FFL). In other embodiments, the reporter gene expression is proportional to HCV entry. In preferred embodiments, the cytoplasmic T7 polymerase or SP6 polymerase RNA amplification system comprises a plasmid encoding a T7 polymerase promoter operably linked to an EMCV IRES in frame with the SP6 polymerase open reading frame and a plasmid encoding an SP6 polymerase promoter operably linked to an EMCV IRES in frame with the T7 polymerase open reading frame. In certain preferred embodiments, a sucrose cushion or gradient is provided for purifying HCV particles or structural proteins. In other embodiments, a filter is provided for purifying HCV particles or structural proteins.

Methods Employing the System for Assaying HCV Particle Entry into a Cell.

The system described above can also be used in methods for assaying HCV particle entry into a cell. HCV particles produced by the first host cell line are collected, and the second cell line is incubated with the HCV particles produced by the first cell line. The expression of the reporter gene is measured, wherein the expression of the reporter gene is proportional to HCV particle entry. In certain preferred embodiments, actinomycin D is added to the second cell line. Actinomycin D is added to block RNA polymerase II-dependent transcription in the nucleus. In other preferred embodiments, the reporter gene is firefly luciferase or EGFP.

The system described above can also be used in methods for identifying cellular proteins necessary for HCV particle entry into the cell, wherein the second host cell is transfected with siRNA targeting a cellular protein. The expression of the reporter gene is proportional to HCV particle entry, and a decrease in viral entry indicates that the protein targeted by the siRNA is a cellular protein necessary for HCV particle entry. In preferred embodiments, the cellular protein is a membrane protein. In some preferred embodiments, the membrane protein is SR-BI, CD81, ASGP-R subunit 1, ASGP-R subunit 2, or claudin-1.

The system described above can also be used in methods for identifying cellular proteins necessary for HCV particle entry into the host cell wherein the second host cell line is transfected with a plasmid encoding a promoter operably linked to a candidate protein gene. The expression of the reporter gene is proportional to HCV particle entry, wherein an increase in viral entry indicates that the candidate protein is a cellular protein necessary for HCV particle entry.

Another use for the system described above is in methods for identifying cellular proteins necessary for HCV particle entry into the host cell, wherein the second host cell line is transduced with a recombinant lentivirus expressing a candidate protein gene. The expression of the reporter gene is proportional to HCV particle entry, and an increase in viral entry indicates that, depending on its location, the candidate protein is a cellular receptor for HCV particle entry.

The system described above can also be used in methods for identifying HCV glycoproteins that are necessary for HCV particle entry into the cell. Incubation of the HCV particles with antibody to a candidate HCV glycoprotein is performed prior to infection of the second host cells with the HCV particles, and expression of the reporter gene is proportional to HCV particle entry. A decrease in HCV particle entry indicates that the candidate HCV glycoprotein is necessary for HCV particle entry into the cell.

Further applications of the system described above include methods for identifying test compounds effective at blocking HCV particle entry into the cells or viral genome uncoating. Incubation of the second host cells with a test compound is performed prior to infection with the HCV particles, wherein a decrease in HCV particle entry or viral genome uncoating indicates that the test compound is effective at blocking HCV particle entry or viral genome uncoating. This is a novel way of testing the effectiveness of potential neutralizing antibodies or vaccines, compared to the use of existing retroviral particles pseudotyped with HCV envelope proteins (HCVpp) or particles produced in, and adapted to, cell culture with a genotype 2a (JFH-1) background (HCVcc).

The system described above can also be used in methods of identifying cellular factors that are involved in the release of infectious HCV particles by host cells expressing WNV subgenomic replicon. A clone of said first host cell line that fails to produce HCV particles capable of entering said second host cell line is identified. cDNA from said clone is isolated. Total RNA was extracted from BHK-WNV1 and from said clone. BHK-WNV1 biotinylated dsDNA was synthesized using CloneMiner cDNA Library Construction kit (Invitrogen) according to the manufacturer's protocol. Biotin-AttB2-oligo(dT) primer was employed to synthesize the first cDNA strand. Second strand synthesis was completed, followed by ligation of AttB1 adapter. cDNA from said clone was synthesized using oligo(dT) primer. Two-round subtractive hybridization is then performed between BHK-WNV1 cDNA and an excess of cDNA from said clone. Biotinylated DNA was pulled down with streptavidin dynabeads and used for recombination cloning and isolation of clones with proper attB1-attB2 ends. Thus, BHK-WNV1 specific genes are isolated. In preferred embodiments, the BHK-WNV1 specific genes comprise calnexin (CANX), small EDRK-rich factor 2 (SERF2), melanocortin 5 receptor (MC5R), alpha-tubulin 4A or v-src homolog protein.

Another use of the system described above is in methods for identifying a test compound that inhibits HCV particle assembly, maturation and/or egress, or genome packaging. Expression and release of the viral proteins and/or reporter gene is measured, wherein expression of the viral proteins and/or reporter gene is proportional to HCV particle assembly, maturation and/or egress, or genome packaging in the first host cell line, and wherein a decrease in viral entry indicates that the test compound inhibits HCV particle assembly, maturation and/or egress, or genome packaging. In certain embodiments, viral production may be measured by the amounts of viral RNA (RT-qPCR), protein (WB, ELISA) and number of particles (EM) released by the producer cell line. In other preferred embodiments, the second host cell line (target cell) is incubated with the HCV particles produced by the first host cell line, and expression of the viral proteins, genomic RNA replication, particle forming unit (infectious titer), with or without trans-complementation (cf. below), and/or reporter gene is measured, wherein expression of those is proportional to HCV particle assembly, maturation and/or egress, or genome packaging in said first host cell line, and wherein a decrease in viral entry (as measured above) indicates that said test compound inhibits HCV particle assembly, maturation and/or egress, or genome packaging.

Methods Employing the Recombinant Mammalian Cell

The recombinant mammalian cell described in the first embodiment can be used in methods for studying the contribution of HCV structural proteins to viral spreading, methods for studying the contribution of HCV non-structural proteins to viral production or in methods for producing infectious HCV containing wild type full length genome without adaptive mutations. The cell may also be used in methods for studying viral spreading and dissemination in an organ, tissue and/or animal, wherein the full-length bi-cistronic genome has been tagged with a TC tag. Another use for the cell is in methods for identifying cellular factors that are involved in the release of HCV particles by host cells expressing WNV subgenomic replicon.

The method for studying the contribution of HCV structural proteins to viral spreading comprises providing a cell according to the first embodiment, wherein the plasmid encodes a T7 or SP6 promoter operably linked to an HCV full-length bi-cistronic genome wherein HCV non-structural proteins are expressed from an EMCV IRES and HCV structural proteins are expressed from an HCV IRES. A second host cell line is incubated with the HCV particles produced by the first host cell line and is transfected with a second plasmid encoding a promoter, operably linked to one or more HCV structural proteins. In preferred embodiments, the promoter is T7, SP6 or cytomegalovirus (CMV) promoter. The production of infectious HCV particles containing the bi-cistronic RNA is measured, wherein an increase in the production of infectious HCV particles containing the bi-cistronic RNA indicates that said one or more HCV structural proteins assist in producing infectious HCV particles.

Also provided herein are methods for studying the contribution of candidate HCV non-structural proteins to viral production through their involvement in viral assembly or egress. A cell according to the first embodiment is provided wherein the plasmid encodes a T7 or SP6 promoter operably linked to an HCV construct wherein one or more HCV structural proteins are expressed from an HCV IRES and one or more candidate HCV non-structural proteins are expressed from a EMCV IRES. If more than one non-structural gene is added, NS3/NS4A protease should be present or another type of cleavage site should be added for processing purposes. The production of infectious HCV particles containing the bi-cistronic RNA is measured, wherein an increase in the production of infectious HCV particles containing the bi-cistronic RNA indicates that said candidate HCV non-structural proteins assist in producing infectious HCV particles through their involvement in viral assembly or egress.

The method for producing infectious HCV containing wild type full-length genome without adaptive mutations comprises providing a cell according to the first embodiment, wherein the plasmid encodes a T7 or SP6 promoter operably linked to an HCV full-length wild type genome wherein HCV proteins are expressed from an HCV IRES. HCV particles containing the bi-cistronic RNA may then be recovered from the cell culture.

In preferred methods employing the system described above or the cell described in the first embodiment, the first host cell line is a BHK-21 stable cell line and the second host cell line is a HuH-7.5 stable cell line. In other embodiments, the recombinant mammalian cell may be any human hepatic cell, including other hepatic cell lines, fetal cell lines, primary cells, liver slices or other organotypic liver culture or bioreactor.

The cell described in the first embodiment can also be used in methods for studying viral spreading and dissemination in an organ, tissue and/or animal, wherein the full-length HCV genome has been tagged with a TC tag. A target organ, tissue or animal is incubated or exposed to the tagged HCV particles, and is then incubated with biarsenical dyes. The spread of the tagged HCV particles is studied in the target organ, tissue or animal, wherein fluorescence of the biarsenical dyes indicates the presence of the TC tag. In certain embodiments the TC tag is within a structural gene, and in other embodiments the TC tag is within a non-structural gene. In certain preferred embodiments, the TC tag is within a non-structural gene. In certain embodiments, the full-length HCV genome is bicistronic. In other embodiments, the full-length HCV genome is monocistronic wild-type. For full-length bicistronic HCV genome, trans-complementation may be performed by plasmid transfection for cells or tissues, or using a lenti-retroviral vector for cells, tissues or animals The cell described in the first embodiment can also be used in methods for identifying cellular factors that are involved in the release of HCV particles by host cells expressing WNV subgenomic replicon. BHK-WNV1 cells are provided and are transfected with a plasmid encoding siRNA directed to a target candidate cellular protein. In certain embodiments, the BHK-WNV1 cells are instead transfected with siRNA or with a plasmid encoding a RNA polymerase III promoter operably linked to small hairpin RNA (shRNA) directed to a target candidate cellular protein. The cells are also transfected with a plasmid encoding HCV. HCV release by the cells is quantified, wherein a decrease in HCV release indicates that the candidate cellular protein is involved in the release of HCV particles. In preferred embodiments, the candidate cellular protein comprises calnexin (CANX), small EDRK-rich factor 2 (SERF2), melanocortin 5 receptor (MCR5R), tubulin alpha 4A, v-src homolog protein, rab1 or atlastin.

The cell described in the first embodiment can also be used in methods for identifying cellular proteins involved in viral assembly, maturation or egress. A candidate protein that is a connecting partner of a previously identified cellular protein involved in viral assembly, maturation or egress is identified through bioinformatic analysis. BHK-WNV1 cells are provided and are transfected with a plasmid encoding siRNA directed to said candidate connecting partner. In certain embodiments, the BHK-WNV1 cells are instead transfected with siRNA or with a plasmid encoding a RNA polymerase III promoter operably linked to small hairpin RNA (shRNA) directed to a target candidate connecting partner. The cells are also transfected with a plasmid encoding HCV. Viral assembly, maturation or egress is quantified in the cells, wherein a decrease in viral assembly, maturation or egress indicates that the candidate protein is involved in HCV assembly, maturation or egress. In preferred embodiments, the candidate protein comprises Rab1, atlastin, GM130 or p115/USO1. Virus assembly can be analyzed by EM, maturation of viral glycoproteins can be analyzed by endo H sensitivity, and virus egress can be analyzed by Western Blot, ELISA and RNA reverse transcription-quantitative PCR (RT-qPCR).

The cell described in the first embodiment can also be used in methods related to those employing the system for assaying HCV particle entry into the cell described supra. For example, the cell described in the first embodiment may be used in methods for assaying HCV particle entry into a cell, in methods for identifying cellular proteins necessary for HCV particle entry into a host cell, and in methods for identifying HCV glycoproteins that are necessary for HCV particle entry into the cell. It can also be used in methods for identifying test compounds effective at blocking HCV particle entry into the cells or viral genome uncoating. It can also aid in identifying cellular factors that are involved in the release of infectious HCV particles by host cells expressing WNV subgenomic replicon, as well as in identifying a test compound that inhibits HCV particle assembly, maturation, egress or genome packaging.

The method for assaying HCV particle entry into a cell comprises providing a cell according to the first embodiment. HCV particles produced by the cell are collected, and a second host cell line is incubated with the HCV particles produced by the first cell. The presence of viral proteins or viral RNA in the second host cell line is measured, wherein the presence of viral proteins or viral RNA in the second host cell line is proportional to HCV particle entry. In preferred embodiments, the presence of viral proteins is detected by ELISA or Western blot. In other preferred embodiments, the presence of viral RNA is detected by Northern blot or RT-PCT.

The method for identifying cellular proteins necessary for HCV particle entry into the host cell comprises providing a cell according to the first embodiment. HCV particles produced by the first cell are collected. A second host cell line is transfected with siRNA targeting a cellular protein. The second host cell line is incubated with the HCV particles produced by the first cell. The presence of viral proteins or viral RNA in the second host cell line is measured, wherein the presence of viral proteins or viral RNA in the second host cell line is proportional to HCV particle entry, and wherein a decrease in viral entry indicates that the cellular protein targeted by the siRNA is a cellular protein necessary for HCV particle entry.

The method for identifying cellular proteins necessary for HCV particle entry into the host cell comprises providing a cell according to the first embodiment. HCV particles produced by the first cell are collected. A second host cell line is transfected with a plasmid encoding a promoter operably linked to a candidate protein gene. The second host cell line is incubated with the HCV particles produced by the first cell. The presence of viral proteins or viral RNA in the second host cell line is measured, wherein the presence of viral proteins or viral RNA in the second host cell line is proportional to HCV particle entry, and wherein an increase in viral entry indicates that the candidate protein is a cellular protein necessary for HCV particle entry.

The method for identifying cellular proteins necessary for HCV particle entry into the host cell comprises providing a cell according to the first embodiment. HCV particles produced by the first cell are collected. A second host cell line is transduced with a recombinant lentivirus expressing a candidate protein gene. The second host cell line is incubated with the HCV particles produced by the first cell. The presence of viral proteins or viral RNA in the second host cell line is measured, wherein the presence of viral proteins or viral RNA in the second host cell line is proportional to HCV particle entry, and wherein an increase in viral entry indicates that the candidate protein is a cellular protein necessary for HCV particle entry.

The method for identifying HCV glycoproteins that are necessary for HCV particle entry into the cell comprises providing a cell according to the first embodiment. HCV particles produced by the first cell are collected. A second host cell line is incubated with the HCV particles produced by the first cell. The presence of viral proteins or viral RNA in the second host cell line is measured, wherein the presence of viral proteins or viral RNA in the second host cell line is proportional to HCV particle entry, and incubating the HCV particles with antibody to a candidate HCV glycoprotein is performed prior to infection with the HCV particles, and wherein a decrease in HCV particle entry indicates that the candidate HCV glycoprotein is necessary for HCV particle entry into the cell.

The method for identifying test compounds effective at blocking HCV particle entry into the cells or viral genome uncoating comprises providing a cell according to the first embodiment. HCV particles produced by the first cell are collected. A second host cell line is incubated with the HCV particles produced by the first cell. The presence of viral proteins or viral RNA in the second host cell line is measured, wherein the presence of viral proteins or viral RNA in the second host cell line is proportional to HCV particle entry or viral genome uncoating. The second host cells are incubated with a test compound prior to infection with the HCV particles, wherein a decrease in HCV particle entry or viral genome uncoating indicates that the test compound is effective at blocking HCV particle entry or viral genome uncoating.

The method for identifying cellular factors that are involved in the release of infectious HCV particles by host cells expressing WNV subgenomic replicon comprises providing a cell according to the first embodiment. HCV particles produced by the first cell are collected. A second host cell line is incubated with the HCV particles produced by the first cell. The presence of viral proteins or viral RNA is measured in the second host cell line, wherein the presence of viral proteins or viral RNA in the second host cell line is proportional to HCV particle entry. A clone of the first cell that fails to produce HCV particles capable of entering the second host cell line is identified. cDNA is isolated from the clone and two-round subtractive hybridization is performed between BHK-WNV1 transcriptome under the form of double-stranded cDNA and an excess of cDNA from the clone, wherein BHK-WNV1 specific genes are isolated.

The method for identifying a test compound that inhibits HCV particle assembly, maturation, egress or genome packaging comprises providing a cell according to the first embodiment. The first cell is incubated with a test compound. HCV particles produced by the first cell are collected. A second host cell line is incubated with the HCV particles produced by the first cell. The presence of viral proteins or viral RNA is measured in the second host cell line, wherein the presence of viral proteins or viral RNA in the second host cell line is proportional to HCV particle assembly, maturation and/or egress or genome packaging in the first cell, and wherein a decrease in viral entry indicates that the test compound inhibits HCV particle assembly, maturation, egress or genome packaging. Virus assembly can be analyzed by EM, maturation of viral glycoproteins can be analyzed by endo H sensitivity, and virus egress can be analyzed by Western Blot, ELISA and RNA reverse transcription-quantitative PCR (RT-qPCR).

EXAMPLES

Example 1

Materials and Methods

T7 DdRP Protein (Invitrogen) Using Proteojuice (Novagen)

Plasmid Constructs:

A) Production of recombinant plasmids in *E. coli* in which a bacteriophage DdRP expression is under the control of its own cognate promoter (referred to as autogenes) are unstable and results in low yields and high mutation rates. We therefore designed a new system to amplify the cytoplasmic transcription of plasmids in which the gene of interest is under the control of a DdRP's cognate promoter; this system consists of a set of two plasmid constructs (FIG. 1A): A) Amplification system: 1) pCR-T7p/SP6pol in which bacteriophage SP6 DdRP open reading frame was cloned into pCR2.1 plasmid (Invitrogen) in frame with the second ATG start codon of EMCV IRES under the control of T7 promoter; 2) pSL-SP6p/T7pol in which bacteriophage T7 DdRP open reading frame was cloned into pSL1180 plasmid (Clontech) in frame with the second ATG start codon of EMCV IRES under the control of SP6 promoter. B) HCV-bicistronic (HCVbp) and -wild type (HCVwt)-coding constructs (FIG. 1B): consist of sequences placed under the control of T7 promoter with their first nucleotide matching the transcription start: 1) p684-SG (L+I)-HDV encodes a bicistronic HCV FL genomic RNA under the control of T7 promoter and was obtained by replacing HCV IRES neomycin resistance gene in H-Neo-SG (L+I) construct (Blight, 2003) with HCV structural gene sequence (5'-UTR to NS2) between the T7 promoter and the EMCV IRES. 2) p90-T7p/H77FL-HDV (FIG. 1B) encodes full length genome of wild-type H77 strain, and was obtained by adding hepatitis delta virus (HDV) antigenomic ribozyme at the 3'-end of p90 HCVconFLlongpU; C) HCV reporter (HCVrp)-coding construct and reporter plasmid (FIG. 1C): 1) pCMV(−)T7p/HCV-SP6pol-HDV encodes a bicistronic entry signal transcript in which the HCV 5'-UTR and structural genes sequence is followed by that of a DdRP in frame with EMCV IRES and a sequence encoding the HCV carboxy-terminus of NS5B (kissing loops; Friebe, P. et al., 2005. *J. Virol.* 79, 380-392) and 3'-UTR. A sequence coding for an HDV antisense ribozyme (Wadkins and Been, 2002. *Cell. Mol. Life. Sci.* 59, 112-125) was added at the 3'-end of both constructs to ensure proper termini of the transcripts (the 5'-end is uncapped by design). This plasmid will produce HCV particles that encapsidate Sp6pol-containing RNA. 2) To detect this incoming RNA in the target cells, a reporter plasmid pT7-SP6p2/EGFPLuc was made. This plasmid was derived from pEGFPLuc plasmid (Clontech) in which EMCV-IRES-EGFPLuc expression is under the control of two bacteriophage T7 and SP6 DdRP cognate promoters in tandem; this construct lacks eukaryotic promoter and therefore is responsive either to T7 DdRP, SP6 DdRP or both; it was found responding to either incoming DdRP protein or encoding RNA (data not shown). D) pHCVp7, is pcDNA3.1 (+) (Invitrogen) plasmid encoding HCV 1a structural genes (core, E1, E2, p7) under a CMV early promoter. E) pIRES1hyg plasmid (Clontech) encoding West Nile virus structural genes (core, prM and E) under a CMV promoter was given by Ted Pierson (Pierson et al., 2006. *Virology* 346, 53-65).

Antibodies.

ALP98 and AP33 are anti-E2 monoclonal antibodies (Owsianka, A. et al., 2001. *J. Gen. Virol.* 82, 1877-1883), kindly provided by Arvind Patel (MRC, Glasgow). An anti-E1 monoclonal antibody (A4), and anti-core Mab, both were provided by Ramsey Cheung (Stanford University). Rabbit polyclonal antibody against HVR1 of E2 (Farci, P., et al., 1996. *Proc. Natl. Acad. Sci. USA* 93, 15394-15399) was a gift from R. Purcell and S. Emerson (LID/NIAID/NIH). To produce rabbit antibody against NS5A, 48-amino-acid peptide corresponding to amino acids 2261-2308 of H77 strain (1a genotype): (SEQ ID NO:1: $NH_2$-AEEDEREVSVPAEILRKSRRFARALPVWARPDYNPPLVETWKKPDYEP-COOH) was synthesized by Peptide Synthesis and Analysis Laboratory (RTB/NIAID/NIH, Twinbrook I, Rockville, Md. 20852), a cysteine was added at the amino-terminus for coupling purpose and peptide was coupled to KLH. Two rabbits were immunized from which two sera were harvested with the following titers (as measured by ELISA against the peptide): 1/315,000 (works best for Western blot) and 1/140,000 (works best for immunofluorescence), respectively; both IgGs were peptide affinity-purified. Sequence of the peptide is almost identical (but amino acids 22, 25, 43 and 46) to that of Con1 (genotype 1b) and second half (23 to 46) is shared with that of JFH-1 (genotype 2a).

Antibodies against cellular proteins/markers are as follows: MAbs against human CD81 (JS-81) and heat shock proteins (hsp90 and hsp70) were obtained from BD Biosciences; rabbit polyclonal anti-SR-BI (NB400-104) was purchased from Novus Biologicals, mAb against ASGPR1 (clone 8D7) was from Santa Cruz Biotechnology, anti-claudin mAb was obtained from Zymed (Invitrogen), monoclonal anti-ERGIC53 (clone G1/93) antibody was from Alexis Biochemicals, anti-BrdU mAb was from Molecular Probes (Invitrogen). For flow cytometry and immunofluorescence (confocal microscopy) analysis, the secondary antibodies used were Alexa Fluor 488- or 635-conjugated goat anti-mouse and Alexa Fluor 594-conjugated goat anti-rabbit antibodies from Molecular Probes (Invitrogen, Carlsbad, Calif.).

Antibodies against HCV candidate receptors are as follow: JS-81 mAb for CD81 (BD Biosciences); rabbit polyclonal anti-SR-BI (Novus Biologicals); ASGPR1 (clone 8D7) mAb (Santa Cruz Biotechnology), and anti-claudin mAb (Invitrogen). Antibodies against various cellular proteins are as followed: Hsp90, Hsp70, and p115 (BD Biosciences); ERGIC-53 (Alexis Biochemicals); BrdU and GDI (Invitrogen); Rab 1 and atlastin (Santa Cruz Biotechnology); calnexin (Abcam); and calreticulin (Cell Signaling Technology). FlAsH- and ReAsH-EDT2 labeling reagents, Hoechst 33342, and Mito Tracker Orange CMTMRos were obtained from Molecular Probes (Invitrogen). For flow cytometry and immunofluorescence (confocal microscopy) analysis, the secondary antibodies used were Alexa Fluor 488-, 594-, or 635-conjugated goat anti-mouse and anti-human antibodies, and Alexa Fluor 594-, 635-, or -680 conjugated goat anti-rabbit antibodies from Molecular Probes (Invitrogen).

Cell Cultures:

A) Baby hamster kidney (BHK-21) cells and derived clones: (i) BHK-21 cells were grown in EMEM supplemented with 10% fetal bovine serum (FBS; HyClone); (ii) BHK cells harboring WN virus lineage II SG-replicon (herein referred to as BHK-WNV1 cells, provided by Ted Pierson, LVD, NIAID) were propagated in DMEM (Biofluids) supplemented with 10% FBS, Glutamax-I (Gibco, Invitrogen) and 5 µg/ml blasticidin; (iii) BHK cells harboring Dengue 2 virus SG-replicon (BHK-Den2 cells, provided by R. Padmanabhan, Georgetown University) were grown in EMEM supplemented with 10% FBS, Glutamax-I and 400 µg/ml G-418. B) HuH-7.5 cells (provided by Charlie M. Rice/Apath) and derived clones: (i) HuH-7.5 cells were maintained in DMEM supplemented with 10% FBS, Glutamax-I, non-essential amino acid mix (Gibco, Invitrogen) and penicillin/streptomycin (Biofluids); (ii) HuH-7.5 cells harboring HCV SG-replicon of 1a genotype (H77) with mutations in NS3 and NS5A (HuH-7.5-1a rep) were obtained by electroporating the parental cells with in vitro transcript RNA generated from H-SG (L+I) plasmid (a gift from Charlie M. Rice; Blight, K. et al., 2003. *J. Virol.* 77, 3181-3190). HuH-7.5-1a rep cells were grown in same medium as parental cells supplemented with 750 µg/ml G-418. C) Human embryonic kidney (HEK-293) cells and derived clones: (i) HEK-293 cells were grown in DMEM supplemented with 10% FBS and Glutamax-I; (ii) 293T cells harboring WN virus lineage II SG-replicon (obtained by electroporating the parental cells with total RNA from BHK-WN1 cells) were grown in same medium supplemented with 5 µg/ml blasticidin; (iii) 293F cells were grown in DMEM supplemented with 10% FBS, Glutamax-I, non-essential amino acid mix, 25 mM Hepes (Gibco, Invitrogen) and penicillin/streptomycin. D) Other cell lines: (i) Human osteosarcoma cells expressing CCR5 (HOS-CCR5) were grown in DMEM supplemented with 10% FBS, Glutamax-I and 1 µg/ml puromycin; (ii) HeLa, SW13 and HepG2 were grown in EMEM supplemented with 10% FBS, Glutamax-I and non-essential amino acid mix.

Production of HCV Particles in Mammalian Cells:

One day before transfection, BHK-WNV1 cells were seeded at a density of $8 \times 10^6$ cells per 162-cm$^2$ flask. Plasmids encoding HCV sequence under the control of CMV early promoter or bacteriophage T7 promoter (cf. above) were transfected using Lipofectamine LTX and Plus reagent according to the manufacturer's protocol (Invitrogen). Culture medium after transfection was DMEM supplemented with 10% FBS, non-essential amino acid mix, Glutamax-I, 25 mM Hepes, 3.7 g/l sodium bicarbonate and Penicillin-Streptomycin. Cells were incubated at 37° C. for 3-4 days in an incubator with a 95% air/5% $CO_2$ atmosphere saturated in humidity. Culture medium were harvested, centrifuged at 30,000×g for 30 min at 4° C. to remove cell debris, then clarified supernatants were centrifuged at 100,000×g for 3 hrs at 4° C. Pellets were resuspended in ice-cold Tris-buffered saline solution (TBS; Quality Biologicals, MD) containing protease inhibitor cocktail (Roche) and loaded on the top of a discontinuous gradient: equal volumes of 30, 45 and 60% sucrose in phosphate-buffered saline solution (PBS), then centrifuged at 85,000×g for 11 hrs at 4° C. Gradients were manually harvested from the top in 20×200 µl fractions; density was evaluated by measuring optical deviation of each fractions (Baush & Lomb densitometer).

Alternatively, the following protocol may be used: One day before transfection, BHK-WNV1 cells were seeded at a density of $6 \times 10^6$ cells per 162-cm$^2$ flask. Plasmids encoding HCV sequence under the control of CMV early promoter or bacteriophage T7 promoter (cf. above) were transfected using Lipofectamine LTX and Plus reagent according to the manufacturer's protocol (Invitrogen). Culture medium after transfection was D-MEM supplemented with 10% FBS, non-essential amino acid mix, Glutamax-I, 25 mM Hepes and 3.7 g/L sodium bicarbonate. Cells were incubated at 37° C. for 3 days in an incubator with a 95% air/5% $CO_2$ atmosphere saturated in humidity. Culture medium were harvested, centrifuged at 30,000×g for 30 min at 4° C. to remove cell debris, then clarified supernatants were filtered with 0.45 µm PVDF membrane (Millipore) and centrifuged at 100,000×g for 3 hrs at 4° C. Pellets were resuspended in ice-cold Tris-buffered saline solution (TBS; Quality Biologicals, MD) containing protease inhibitor cocktail (Roche) and loaded on the top of a 20-60% sucrose gradient in phosphate-buffered saline solution (PBS), then submitted to centrifugation with a SW55Ti rotor (Beckman) at 100,000×g for 16 hrs at 4° C. Gradients were manually harvested from the top in 30×150 µl fractions.

Transmission Electron Microscopy (TEM) Analysis.

BHK-WNV1 SG-rep cells seeded in a 6-well plate ($2.5 \times 10^5$ cells) were transfected with HCVbp-coding construct plus the amplification system. Three days later, cells were fixed in 2% glutaraldehyde in 0.1 M sodium cacodylate for 1 hr at RT, then at 4° C., overnight. Cells were subsequently processed for TEM analysis, as previously described (Dussupt, V. et al., 2009. *PLoS Pathog.* 5, e10000339. doi:10.1371/journal.ppat. 10000339).

Pools of sucrose fractions containing HCVwt were diluted with PBS then pelleted in Beckman SW55Ti (100,000×g, for 2 hr) at 4° C. Pellets were resuspended in 4% paraformaldehyde in PBS and analyzed for negative staining EM.

Analyses of the Glycosylation of HCV Envelope Proteins and its Effects.

To test the sensitivity of HCV glycoproteins produced in BHK-21 cells to endo-beta-N-acetyl-glucosaminidase H (endoglycosidase H/endo-H; New England Biolabs), cells were transfected with pHCVp7 plasmid. Three days later, supernatant was harvested as above; cell lysate and supernatant were then incubated in the presence of endo-H according to the manufacturer's protocols. For deoxyrijinomycin (DNJ) and brefeldin A (BFA) treatment, cells were transfected with pHCVp7 and, 12 hr later, the medium was replaced with DMEM containing 5 μg/ml BFA (Sigma), or 3 mM DNJ. Cells were grown for another 24 hr and supernatant was harvested.

RNA Analysis and RT-qPCR.

A) Total RNA from sucrose fractions was extracted with Trizol LS (Invitrogen). RT-qPCR (TaqMan) of HCV 5'-UTR RNA was performed with QuantiTect Probe PCR kit (Qiagen) using IVT RNA standard corresponds to the HCV 5'-UTR. Briefly, nt 1-587 of p90HCVconFLlongpU was cloned into pCRII (Invitrogen) downstream of T7 promoter, resulted in pCRII-5'UTR. Plasmid was linearized with Kpn I, ethanol precipitated and used as DNA template for IVT RNA standard using T7 MEGAScript (Ambion). After Turbo DNAse treatment and acid phenol extraction, IVT RNA standard was resuspended in RNA storage solution (Ambion). For cDNA synthesis, IVT RNA standards were diluted 10-folds ranging from 1 ng to 1 fg in $H_2O$. RT was performed with Superscript III (Invitrogen) at 50° C., for 1 hr with p322 reverse primer (CTC CCG GGG CAC TCG CAA GC). One-tenth of cDNA products were used for TaqMan PCR using p44 forward (CCT GTG AGG AAC TAC TGT CTT CA) and p265 reverse (AAC ACT ACT CGG CTA GCA GTC TT) primers, together with a dual-labeled probe (CAL Fluor Gold 540 fluorophore-TCT GCG GAA CCG GTG AGT ACA-BHQ-1 quencher) (Biosearch Technologies, CA). TaqMan PCR was carried out at 94° C. (15 sec), 56° C. (30 sec), and 76° C. (30 sec) for 45 cycles on a 7900HT thermocycler (Applied Biosystems). B) HCV RNA analysis in HuH-7.5 cells after infection with HCVbp: see below. C) HCV and WNV RNA analysis from BHK-WNV1 cells: Total RNA was extracted from cells and pelleted supernatants as in (A) followed by RT using random hexamer and Superscript III at 50° C., for 1 hr. qPCR was performed with HCV specific primers as above, or, *Renilla* luciferase-specific primers as the target gene for WNV-SG rep RNA.

Infectivity Assay with HCVbp:

BHK-WNV1 cells were co-transfected with p684-SG (L+I)-HDV and the amplification system plasmids (pCR-T7p/SP6pol and pSL-SP6p/T7pol). Fractions were harvested as described above or pellet was suspended and serially diluted in Opti-MEM I before directly adding onto target cells. A) Indirect immunofluorescence analysis: HuH-7.5 cells were seeded on 8-well chambered coverglass (Lab-Tek II, Nalgen Nunc) at a density of $7 \times 10^3$ cells per well. One day after seeding, cells were incubated with HCV particles for 1 hr at 37° C., after which virus inoculum was removed, and cells were grown for another 48 hr. Expression of HCV NS5A protein was detected at 2 day post-infection. Briefly, cells were washed twice with ice-cold PBS and fixed with 4% paraformaldehyde and 0.15 M sodium cacodylate buffer, pH 7.4, for 20 min at room temperature, followed by washing (for 5 minutes, twice) with PBS containing 50 mM glycine to quench excess paraformaldehyde. After washing with PBS, cells were permeabilized with 0.3% Triton X-100 in PBS for 15 minutes at room temperature, then incubated with blocking solution (10% FBS, 3% BSA, 0.3% Triton X-100 in PBS) for 30 min. Cells were then incubated with primary antibodies: rabbit anti-NS5A IgG (in-house) and anti-ERGIC-53 mAb (in 1% BSA, 0.1% Triton X-100 in PBS) overnight at 4° C. The fluorescent secondary antibodies were Alexa Fluor 488-conjugated anti-mouse IgG antibody and Alexa Fluor 594- or 635-conjugated anti-rabbit IgG antibodies. Nuclei were labeled with 4',6-diamino-2-phenylindole dihydrochloride (DAPI) with antifade (Chemicon, CA). Analysis was performed on a Leica SP2 confocal microscope (Leica, Heidelberg, Germany). B) Bromo-uridine incorporation: HuH-7.5 cells were seeded in 8-well chambered coverglass ($7 \times 10^3$ cells/chamber) and one day later, were infected with HCV particles. At 48 hr post-infection, medium was replaced with DMEM complete medium containing 2.5 μg/ml actinomycin D (Sigma) for 30 min and transfected with 5-bromo-uridine 5'-triphosphate (BrUTP; Sigma) using Lipofectamine 2000 (Invitrogen). Briefly, 1 μl of Lipofectamine 2000 was added to 10 mM BrUTP, both in 25 μl Opti-MEM I, and incubated for 20 min at room temperature. The BrUTP-Lipofectamine complex was added drop wise onto cells and further incubated for 6 hours. Cells were then fixed, permeabilized and incubated with anti-BrdU mAb conjugated with Alexa Fluor 488. Confocal microscopy analysis was performed as above. C) Live-cell imaging of infected cells with HCVbp-4-cys: HuH-7.5 cells were infected with HCVbp-4-cys for 3 days, then incubated with the cell-permeant FlAsH-$EDT_2$ or ReAsH-$EDT_2$ biarsenical dye (Molecular Probes, Invitrogen) according to the manufacturer's protocol. Adding FlAsH (or ReAsH) dye onto live cells expressing TC-tagged proteins should result in a specific fluorescent signal where the tag is present. Thus, infected cells that had accumulated enough TC-tagged non-structural protein upon viral replication will display a specific staining in the cytoplasm. Cells were observed with a Leica SP5 X-WLL (white light laser) mono-photon confocal microscope (Leica, Heidelberg, Germany). D) HCV RNA analysis in HuH-7.5 cells after infection with HCVbp: HuH-7.5 cells (5,000 cells/well) were seeded in triplicate on collagen-coated 96-well plates (BD BioCoat). The next day, cells were infected with aliquots of sucrose fractions containing HCVbp for 3 hr; after virus inoculum removal, cells were allowed to recover for another 3 hr, then transfected with pcDNA 3.1-based plasmid encoding HCV core-NS2, or, pcDNA 3.1 empty vector. HCV RNA was analyzed directly from infected cells harvested daily until day 5 using TaqMan Gene Expression Cells-to-Ct kit (Ambion). Briefly, cells were washed once with 150 μl ice-cold PBS, then dissociated with 25 μl TrypLE (Invitrogen) for 15 min at 37° C. After inactivation of TrypLE with D-MEM, cells were pelleted (1500 rpm, 10 min, 4° C.), then washed with ice-cold PBS (1500 rpm, 10 min, 4° C.) and stored at −80° C. RT step was performed directly from cell lysates according to the manufacturer's protocol, followed by TaqMan PCR with some modifications. Briefly, PCR was performed with HCV specific primers and probe as above; the PCR condition was 50° C. for 2 min, 95° C. for 10 min, then 95° C., 15 sec; 55° C., 30 sec; 72° C., 30 sec for 45 cycles.

Entry Assay with the Reporter System:

BHK-WNV1 cells were co-transfected with pCMV(−)T7p/HCV-SP6pol-HDV and the amplification system plasmids (pCR-T7p/SP6pol and pSL-SP6p/T7pol). Previous validation of amplified reporter system was achieved either after transfecting target cells with T7pol RNA produced in HuH-7 cells infected with vTF7-3, a recombinant vaccinia virus encoding T7pol (Fuerst, T. R. et al., 1986. *Proc. Natl. Acad. Sci. USA* 83, 8122-8126) or, more directly, with recombinant T7pol using ProteoJuice (Novagen) (not shown). Fractions were harvested as described above or pellet was suspended and serially diluted in Opti-MEM I before directly adding onto target cells. HuH-7.5 cells or other tested target cells were split one day before the assay and, depending on cell type, seeded at a density of $2.5-4 \times 10^4$ cells/well in sterile cell culture-treated 96-well opaque white plates (Nunclon). Unless otherwise specified, infectivity assays were performed in triplicates. After removing culture medium, fraction aliquots diluted in Opti-MEM I were added onto the cells and incubated at 37° C. for an hour. At the end of the incubation period, unbound material was removed and, using Lipofectamine LTX and Plus reagent, cells were transfected with a mix of plasmids containing the amplification system and reporter plasmid. After transfection, culture medium containing 0.05 µg/ml actinomycin D (added to reduce background of amplified reporter system, generally <1% of maximum signal) and cells were further incubated at 37° C. for a period of 20-24 hours. Cells were then washed once with ice-cold PBS and lysed with 20 µl 1× Glo Lysis Buffer (Promega) and incubated at room temperature for at least 15 minutes. Luciferase activities were measured in each well using 50 µl Bright-Glo Luciferase Substrate (Promega) using a Clarity luminescence plate reader (Biotek).

To address the question that HCV particles only encapsidate their own genomic RNA, and not that of WN SG-replicon RNA, we performed the following. The WNV SG-replicon of BHK-WNV1 cells encodes *Renilla* luciferase (RNL), in addition to the antibiotic selection marker (Pierson, T. et al., 2006. *Virology* 346:53-65). To analyze if WNV SG-replicon RNA was associated with the HCV particles, we performed i) RT-qPCR to detect WNV5' UTR in the pelleted SN, and ii) RNL activity in the target cells using Enduren (Promega). Total RNA was extracted from cells and pelleted supernatants as described above followed by RT using random hexamer and Superscript III at 50° C., for 1 hr. qPCR was performed with HCV specific primers as above, or, *Renilla* luciferase-specific primers as the target gene for WNV-SG rep RNA We tested various cell lines used in previous HCV entry studies: HuH-7, Bsc-1, 293T, HeLa, Hos-CCR5, SW13 and HepG2 cells (Table 1); the entry signal in the last four cell types was either weak or totally absent. Positive cells expressed the asialoglycoprotein receptor (ASGP-R or Ashwell receptor), which was, however, not sufficient (HepG2 cells). We have previously shown that ASGP-R was required for the internalization of HCV materials, including in non-target cells (Saunier, B. et al., 2003. *J. Virol.* 77, 546-559). In the liver, ASGP-R is involved in endocytosis via clathrin-coated pits (Katzir et al., 1994. *J. Biol. Chem.* 269, 21568-21575) and HCV has since been reported entering cells by clathrin-coated pits (Meertens, et al., 2006. *J. Virol.* 80, 11571-11578; Codran, et al., 2006. *J. Gen. Virol.* 87, 2583-2593; Blanchard, et al., 2006. *J. Virol.* 80, 6964-6972).

siRNA in HuH-7.5 Cells:

HuH-7.5 cells were seeded in 6-well plates ($3\times10^5$ cells/well); 24 hrs after plating, cells were transfected with 2 µM siRNA (Dharmacon) targeting either CD81, SR-BI, Claudin-1, or ASGPRs 1 and 2 siRNA following the manufacturer's instruction. To test the specificity and efficiency of siRNA delivery, cells were transfected with non-target siRNA and siGlo (Dharmacon), respectively. The efficiency of siRNA to knock down the intended target gene was confirmed 3 days post-transfection by flow cytometry (CD81, ASGPR and siGlo) or Western Blot (Claudin-1 and SR-BI).

To test the siRNA effect on HCVrp infectivity with the reporter system, siRNA-treated cells were dissociated at 48 hr post transfection and seeded in 96-well plate at $5\times10^4$ cells/well. Twenty-four hours later, cells were infected with HCVrp (prepared from BHK-WNV1 transfected with pCMV(−)T7p/HCV-SP6pol-HDV; see plasmid constructs) for 1 hr and transfected with the reporter system. The efficiency of siRNA to inhibit HCVrp entry was assessed by the reduction of firefly luciferase activity compared to the control cells the next day.

HuH-7 cells had been shown to be permissive for WNV infection and capable of producing infectious particles (Fredericksen et al., 2004. *J. Virol.* 78, 7737-7747). Likewise, HuH-7.5 cells were also susceptible to WNVrp infection (FIG. 6A). BHK-WNV1 cells were transfected with a plasmid encoding the structural genes of WNV (core, prM and E); after three days, particles from supernatant were harvested by centrifugation through 15% sucrose cushion at 100,000×g for two and half hours. The pellet containing WNVrp was resuspended and used for infection of HuH-7.5 cells (siRNA-treated or non-treated). After two days, the level of RNL activity in target cells was measured using the *Renilla* Luciferase Assay System (Promega) as recommended by the manufacturer using a Clarity luminescence plate reader (Biotek), or using the live-cell/permeant RNL substrate Enduren over a period of 1 to 3 days.

Transduction of HepG2 with Lentivirus-hCD81.

To obtain human CD81 DNA, total RNA was extracted from HuH-7.5 cells, and CD81 cDNA was synthesized with gene specific primer using Superscript RT III (Invitrogen) at 55° C., followed by PCR to amplify the full-length CD81 coding region. The PCR product was cloned into pENTR 2B (Invitrogen), its sequence was verified by sequencing, and the pENTR-hCD81 was used for recombination with pLenti6.2/V5-DEST (Invitrogen) according to the manufacturer's protocol. To produce recombinant lentivirus-hCD81 using ViraPower Lentiviral Expression Systems (Invitrogen), $5\times10^6$ cells of 293 FT cells were seeded in a 10 cm tissue culture dish containing 10 ml D-MEM supplemented with 10% FBS, 0.1 mM NEAA, 1% Glutamax, 1 mM sodium pyruvate, overnight. The following day, the medium was replaced with 5 ml fresh medium. Meanwhile, 9 µg ViraPower Packaging Mix was mixed with 3 µg pLenti6.2-hCD81 in 1.5 ml Opti-MEM I. In a separate tube, 36 µl of Lipofectamine 2000 was diluted in 1.5 ml Opti-MEM I. After 5 min incubation, DNA was mixed with Lipofectamine 2000, and further incubated for 20 min at RT. The transfection mixture was added drop wise to cells and incubated overnight. On day 3, the medium was replaced with fresh 10 ml complete medium, and virus-containing supernatant was harvested at 72 hr post-transfection. To remove cell debris, supernatant was centrifuged (3000 rpm, 15 min, 4° C.) and filtered through Millex-HV 0.45 µm. Viral stock was stored at −80° C. To transduce HepG2 cells, $5\times10^5$ cells were seeded in a 6-well tissue culture plate, overnight. The following day, the medium was aspirated and cells were transduced with lentivirus-hCD81 diluted in Opti-MEM I (total volume of 1 ml) containing 10 µg/ml Polybrene. Virus-containing medium was replaced 24 hr later with 2 ml fresh medium. Three days after transduction, the medium was replaced with fresh medium containing 2 µg/ml Blasticidin, and medium was replaced every 3-4 days. The antibiotic-resistance colonies was expanded and analyzed for CD81 expression by flow cytometry. Parental HepG2 and HepG2-hCD81 cells were seeded on collagen-coated 8-well chamber slides and, the following day, were incubated with HCVbp for 2 hour. After virus inoculum removal, cells were further grown for 48 hours, then fixed, permeabilized and analyzed for NS5A expression by confocal microscopy.

Treatment of BHK-WNV1 Cells with Antiviral Drugs.

BHK-WNV1 cells were treated with IFN from human leukocytes (Sigma) at 3,000 IU/ml for 10 days, then further treated for 7 days with either: i) IFN alone (1,500 IU/ml), ii) IFN (1,500 IU/ml) plus mycophenolic acid (MPA; 0.5 µg/ml (Sigma), or iii) IFN (1,500 IU/ml) plus Ribavirin (25 µM) (Sigma). The inhibition of WNV SG-rep after antiviral treatments was assessed by their RNL activity. Cells were then transfected with HCVbp-coding plasmid; three days later, the level of HCV secretion was analyzed by WB and compared to that produced by the untreated cells.

Subtractive Hybridization.

To identify cellular factor(s) responsible for the enhanced release/infectivity of HCV particles produced in BHK-WNV1 cells, a subtractive cloning was performed between BHK-WNV1 and its subclone that is not yet capable of producing infectious HCV particles, as tested in HuH-7.5 cells. First, total RNA was extracted from BHK-WNV1 and electroporated into naïve BHK-21 cells. More than 20 clones were selected by limiting dilution in the presence of blasticidin; each clone was tested for WNV replication function by RNL activity and compared to that produced by BHK-WNV1. All clones showed similar level of RNL activity (not shown); we then tested these clones for their ability to produce infectious HCV particles. One clone, BHK-WNV2.13, was chosen because it failed to produce infectious HCVrp, as measured with the reporter system. A modified version of two-round subtractive hybridization (Sagerström, C. G. et al., 1997. *Annu. Rev. Biochem.* 66, 751-783) was performed between BHK-WNV1 double-stranded (ds) DNA and three- or ten-times excess of fresh BHK-WNV2.13 cDNA (FIG. 10A). Briefly, total RNA were extracted from cells by Trizol (Invitrogen) followed by mRNA isolation using Oligotex mRNA maxi kit (Qiagen). BHK-WNV1 biotinylated dsDNA was synthesized using CloneMiner cDNA Library Construction kit (Invitrogen) according to the manufacturer's protocol; the attB1-attB2-flanked dsDNA was then purified through cDNA size column fractionation. Meanwhile, BHK-WNV2.13 cDNA was synthesized using oligo $(dT)_{20}$ and Superscript RT III (Invitrogen) at 50° C. for 1 hr; after the RT step, mRNA template and mRNA-cDNA hybrid were digested with RNAse H and RNAse A at 37° C. for 30 min and cDNA was purified with QIAquick PCR purification column (Qiagen). After elution at 70° C. and ethanol precipitation, cDNA was resuspended in 10 mM Tris, 1 mM EDTA buffer. First round of subtractive hybridization was performed between biotinylated attB1-attB2-flanked dsDNA obtained from BHK-WNV1 mRNA and cDNA from BHK-WNV2.13 mRNA at ratio 1:3 in 40 μl annealing buffer (12.5 mM Hepes-HCl, pH 8.3, 125 mM NaCl, 2.5% PEG 8000, 2.5 mM $MgCl_2$). Hybridization was carried out with a stepwise temperature gradient in a thermocycler (98° C. for 5 sec; 91° C. for 5 sec, 79° C. for 10 sec: 2 cycles; 88° C. for 5 sec, 77° C. for 10 sec: 2 cycles; 85° C. for 5 sec, 75° C. for 10 sec: 2 cycles; 82° C. for 5 sec, 73° C. for 10 sec: 2 cycles; 79° C. for 5 sec, 71° C. for 10 sec: 2 cycles; 76° C. for 5 sec, 69° C. for 10 sec: 2 cycles; 73° C. for 5 sec, 67° C. for 10 sec: 2 cycles; 70° C. for 5 sec, 65° C. for 10 sec: 2 cycles; 67° C. for 5 sec, 63° C. for 10 sec: 2 cycles; 64° C. for 5 sec, 61° C. for 10 sec: 2 cycles; 61° C. for 5 sec, 59° C. for 10 sec: 2 cycles; 58° C. for 1 sec; 56° C. for 1 sec; 54° C. for 1 sec; 52° C. for 1 sec; 50° C. for 1 sec). Following this step, biotinylated DNA was pulled down with Dynabeads MyOne Streptavidin C1 (Invitrogen): 50 μl beads were washed and resuspended in 10 μl 2× Binding & Washing (B&W) buffer (10 mM Tris-HCl pH 7.5, 1 mM EDTA, 2 M NaCl), then saturated with 50 μg salmon sperm DNA at 25° C. for 15 min; after two washes with 1×B&W buffer, beads were resuspended in 32 μl of 2×B&W buffer and incubated at 25° C., for 30 min with gentle mixing (300 rpm) with the biotinylated attB1-attB2-flanked dsDNA: cDNA mix described above. After a three-round wash, biotinylated DNA was eluted from Streptavidin beads with $H_2O$ at 70° C. for 2 min and ethanol precipitated. The DNA pellet was resuspended in 10 μl TE buffer and subjected to a second round of subtractive hybridization, this time at a ratio of 1:10 between eluted DNA and fresh cDNA from BHK-WNV2.13, as described above. The eluted biotinylated dsDNA after this second round was then used for recombination with pDONR 222 (Invitrogen) followed by transformation of ElectroMAX DH10B T1 competent cells according to the manufacturer's protocol. Thirty-seven (37) clones with proper attB1-attB2 ends were sequenced (Table 2, See FIG. 10B).

BHK-WNV1 Cell Gene Knockdown Using siRNAs.

The genes most frequently identified from the subtractive hybridization (see above): calnexin (CANX), small EDRK-rich factor 2 (SERF2), and melanocortin 5 receptor (MC5R), together with tubulin alpha 4A, and v-src, were analyzed for their effects on HCV release. BHK-WNV1 cells were treated with the corresponding siRNA (Dharmacon) for 2 days, re-seeded and transfected the next day with HCV-coding plasmid. Cells and supernatants were harvested 48 hrs later, and analyzed by Western blot. To verify the effects of these genes on HCV release, CNX, SERF2 and TUBA4 cDNAs were synthesized from BHK-WNV1 mRNA, and cloned into pTracer-CMV/Bsd (Invitrogen) Inhibition of HCV release by CANX, SERF2 and TUBA4 siRNAs could partially be overcome when pTracer expressing the respective gene was co-transfected with HCV into the producer cells (FIG. 10C), showing specificity of their knockdown.

Effect of Rab1 on HCV Production by BHK-WNV1 Cells.

A) Co-localization of HCV and Rab1 in the producer cells: BHK and BHK-WNV1 cells were transfected with HCVbp-coding plasmid, and the following day, re-seeded on 8-well chambered coverglass ($5\times10^3$ cells/well). Two days later, cells were fixed and permeabilized as above, then incubated with serum from HCV-infected patient (HCV genotype 1a) and anti-Rab 1 antibodies. B) BHK-WNV1 cells were treated w/siRNA against Rab1 (Dharmacon) for 2 days, re-seeded, and the following day were transfected with HCVbp-coding plasmid. Cells and supernatants were harvested 3 days after transfection; cell lysates and particles released in the supernatants were analyzed by Western blot.

Example 2

Production of HCV-Like Particles by BHK-21 Cells and its Specific Enhancement by Flavivirus SG-Replicons Albeit retained in the endoplasmic reticulum (ER), HCV E1, E2 proteins were previously shown budding into the ER lumen of BHK-21 cells (Dubuisson, J. et al., 1994. *J. Virol* 68, 6147-6160; Blanchard et al., 2003. *J. Virol.* 77, 10131-10138). Flaviviridae replication induces membrane rearrangements, mostly derived from the ER (Egger, D. et al., 2002. *J. Virol.* 76, 5974-5984; Mackenzie et al., 2005. *Traffic* 6, 967-977; Roosendaal et al., 2006. *J. Virol.* 80, 4623-4632), that are probably required for viral assembly and/or release (Sklan, E. H. et al., 2007. *J. Biol. Chem.* 282, 36354-36361); we could, however, not stably establish a HCV subgenomic (SG)-replicon in BHK-21 cells. Although distantly related within the Flaviviridae family, hepaciviruses and flaviviruses still share several features in common (Murray, C. et al., 2008. *Nat. Rev. Microbiol.* 6, 699-708). BHK-21 cells have previously been used to pseudotype flaviviruses. Here we show that replicating flavivirus SG-replicons from West Nile (WN) and dengue 2 (Den2) viruses drastically enhanced the release of HCV particulate materials by BHK-21 cells (FIG. 2A). Effect of WNV SG-replicon was higher than that of Den2 (FIG. 2A, lane 2 and 3). Such enhancement was not observed with Semliki Forest alphavirus SG-replicon (FIG. 2A, lane 4).

We next compared the release in such cells to that of HCV replication permissive HuH-7.5 cells bearing HCV 1a SG-replicon. In HuH-7.5 cells, HCV 1a SG-replicon negatively interfered with the release of HCV envelope proteins (FIG. 2B, right). In addition, HCV structural proteins did not enhance the basal release of HCV SG-replicon (not shown) suggesting these cells were deemed unsuitable for trans-pseudotyping HCV 1a.

Both WNV1 and Den2 SG-replicons express antibiotic selection and *Renilla* luciferase (RNL) genes (Pierson, T. et al., 2006. *Virology* 346, 53-65; Padmanabhan, personal communication). Very high levels of RNL activity were detected in BHK-WNV1 or -Den2 cells (not shown). Nevertheless RNL coding sequence was not detected by RT-qPCR in the released HCV particles suggesting WNV1 or Den2 SG-replicons were not encapsidated or released (not shown). This was confirmed by the lack of detection of RNL activity (measured with a RNL assay kit or the live-cell-permeant RNL substrate Enduren) in HuH-7.5 cells over a period of two days after their incubation with HCV particles, at variance with what we observed with WNVrp (FIG. 6A). These results strongly suggest that, if WN or Den2 SG-replicon were trans-encapsidated in WNVrp (FIG. 6A) or Den2 pseudo-typed particles (Padmanabhan, personal communication), this was not the case in the released HCV-related materials.

Example 3

N-Glycosylation, and not β-Glycosylation, is Required for Processing of HCV Structural Proteins in Producer Cells We treated BHK cells with deoxynojirimycin (DNJ), an early N-glycosylation inhibitor (Mellor et al., 2004. *Biochem J.* 381, 867-875; Jacob, et al., 2007. *J. Microbiol.* 45, 431-440; Steinman, et al., 2007. *Hepatology* 46, 330-338; Wu, et al., 2002. *J. Virol.* 76, 3596-3604), phenyl acetyl galactosaminide (Sadeghi et al., 1999; *Glycobiology* 9, 731-737) or alloxan (Kudlow et al., 2006. *J. Cell. Biochem.* 98, 1062-1075), both are O-glycosylation inhibitors. The latter two had marginal effects, whereas DNJ strongly inhibited the secretion of HCV envelope (FIG. 2C) as well as core (not shown) proteins by BHK parental and -WNV SG-replicon cells. In lysates of BHK parental, or -WNV1 cells, fully cleaved HCV E1 was mainly detected as a doublet of about 35-40 kDa band by Western blot, the lower band predominating, and E2 as a diffuse band around 62 kDa; virtually all E1 and E2 species were endoglycosidase H-sensitive (FIG. 11B) consistently with previous reports with hepatoma cell lines (Dubuisson, J. et al., 1994. *J. Virol* 68, 6147-60; Nielsen et al., 2004. *J. Gen. Virol.* 85, 1497-1507). In the supernatants, in contrast, it was the upper E1 band that was mainly detected (FIG. 2C) and had partially become resistant to a treatment by endoglycosidase H. The partial digestion with endoglycosidase H of the carbohydrate residues of higher molecular weight E1 species was consistent with the existence of multimers with up to four glycosylated sites (FIG. 2C); most released E1 species had three glycosylated sites, amongst which only one was resistant to endoglycosidase H. E1 sensitivity to endoglycosidase H in cell lysates suggests that secretion of HCV particles quickly followed the maturation/processing of the E1 glycosylation site that became resistant. E2 was still mainly visible as a band of 62 kDa with most glycosylation sites becoming resistant to endoglycosidase H (FIG. 11B).

Example 4

Figure 3:
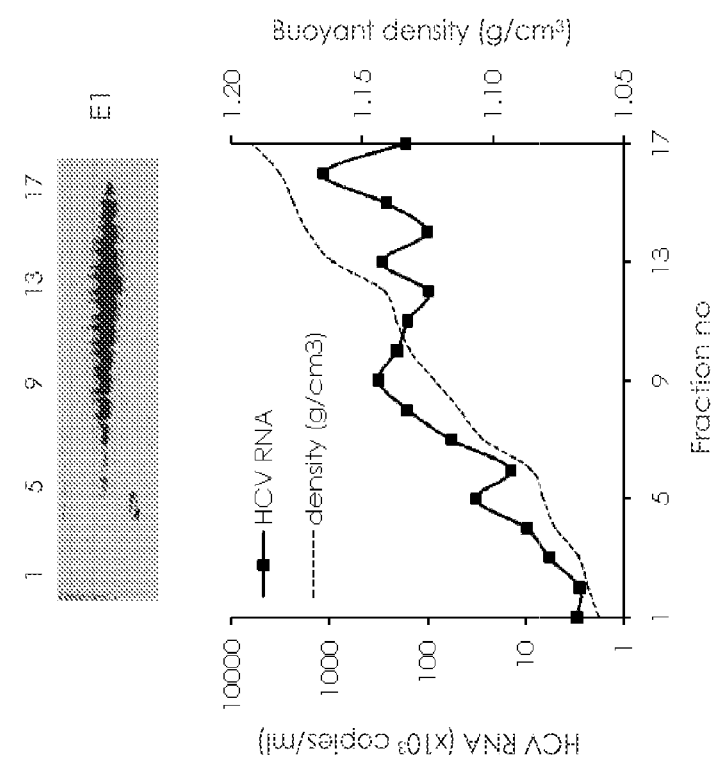
FIG. 3 illustrates the characterization of full-length HCV-bicistronic particles (HCVbp) produced by BHK-WNV1 cells. A) Transmission EM analyses of BHK-WNV1 cells three days after transfection with the system of plasmids producing HCVbp. (upper panels) Membrane rearrangements in BHK-WNV1 cells: convoluted membranes (CM), vesicle packets (VP); (lower panels) Upon transfection, large vesicles (LV) filled with virus-like structures appeared (black arrow) next to ER (white arrow); insets=higher magnification: electron-dense, then cultured for 8 days. Co-immunostaining with anti-HCV antibodies was then observed over a thickness of 60-70 µm with a multifocal confocal microscope. (Lower panels) Human liver slices were infected with BHK-WNV1-derived HCVwt-4-cys for 6 days, then stained with FlAsH and observed over a thickness of ~150 µm with a multiphoton confocal microscope; ML=mediolobular area; PP=periportal space; white arrows indicate positive cells.
Figure 5A:
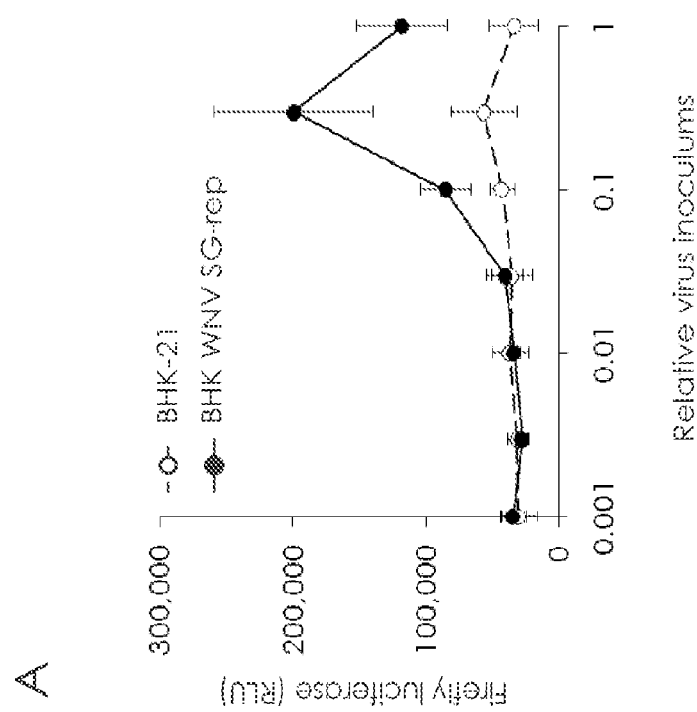

Transmission Electron Microscopy Analysis of BHK-WNV1 Cells Transfected with HCVbp-Coding Plasmid Without any adaptive mutation, FL genomic RNA of HCV genotype 1a (H77) does not highly replicate in cultured HuH-7 cells (Blight et al., 2003. *J. Virol.* 77, 3181-3190). In contrast, SG-replicons bearing cell-culture-adaptive mutations (Blight et al., 2003. *J. Virol.* 77, 3181-90) have been shown replicating to a much higher extent in HCV replication-permissive HuH-7.5 cells (Blight et al., 2002. *J. Virol.* 76, 13001-13014). To address whether HCV particles released in the supernatant of BHK-WNV1 cells could encapsidate an infectious RNA and infect cultured HuH-7.5 cells, we introduced the sequence encoding HCV structural genes upstream that of an adaptive HCV SG-replicon (given by Charles Rice; cf. Materials and Methods and FIG. 1B). In the resulting transcript, translation of HCV structural genes is relying on HCV IRES while EMCV IRES is driving that of the adaptive HCV SG-replicon. Expression of HCV proteins encoded by the bicistronic construct p684-SG(L+I)-HDV in BHK-WNV1 cells resulted in the production of virus particles, herein called HCV-bicistronic particles (HCVbp), as observed by TEM (FIG. 3A, bottom, left panel): large vesicles (LV; not classical multi-vesicular bodies) and filled with ~50-60 nm particles were observed in the vicinity of dilated rough ER protrusions and mitochondria; a higher magnification revealed enveloped particles budding into their lumen (FIG. 3A, right, bottom panel). Control BHK-WNV1 cells only displayed extensive membrane rearrangements, such as vesicle packets (VP, site of RNA replication) and convoluted membranes (CM, site of RNA translation and polyprotein processing) triggered by the WNV SG-rep (Mackenzie, J. 2005. *Traffic* 6, 967-977), but no or empty LV (FIG. 3A, upper panels). Although HCV expression induced the release of WNV SG-rep (FIG. 14A), contrasting with the previous finding that WNV core protein is required (Chang, D. C. et al., 2008. *Nat. Biotech.* 26, 571-577), the secreted HCVbp preferentially contained the bicistronic HCV RNA (FIG. 14B). They displayed buoyant densities ranging from 1.05 to 1.16 g/cm$^3$ (FIG. 3B) and, upon incubation with HuH-7.5 cells, no RNL activity was detected (FIG. 14B), indicating that WNV SG-rep was not trans-packaged within infectious HCV particles.

BHK-WNV1 Cell-Produced HCVbp is Infectious for HuH-7.5 Cells.

Culture media of BHK-WNV1 cells transfected with HCVbp-coding plasmid was harvested 3 days later, and clarified supernatant was filtered then concentrated (60-fold) with Amicon Ultracel-100K (Millipore) and used to infect HuH-7.5 cells. Two days after infection, HuH-7.5 cells were analyzed using a laser-scanning confocal microscope. NS5A-positive patches were detected in the cytoplasm of infected cells (FIG. 4A, top panels). Cells were then incubated with actinomycin D to block RNA polymerase II-dependent transcription in the nucleus, and loaded with 5-bromo-UTP, a nucleotide analog incorporated into RNAs during their elongation. Anti-bromo-uridine (BrU) antibody recognized structures in the cytoplasm of HuH-7.5 cells incubated with HCVbp or stably expressing HCV SG-rep (FIG. 4A, middle panels), which likely reflected the local incorporation of BrU into replicating HCV RNA, like for flaviviruses (Westaway, E. G. et al., 1999. *Virology* 258, 108-117). A variant of HCVbp was obtained by inserting a tetra-cysteine tag (Griffin, B. A. et al., 1998. *Science* 281, 269-272) within one of the non-structural genes. NS5A was the non-structural gene that was tagged in this experiment, but other non-structural genes could also be tagged. Functionality of the RNA packaged in released particles (HCVbp-4-cys) was analyzed in live HuH-7.5 cells. After 3-day infection, incubation of the cells with permeant bi-arsenical dyes (Methods) elicited a specific staining predominantly in the perinuclear area (FIG. 4A, bottom panels), suggesting that replicating RNA had produced enough tag-labeled protein.

Figure 7:
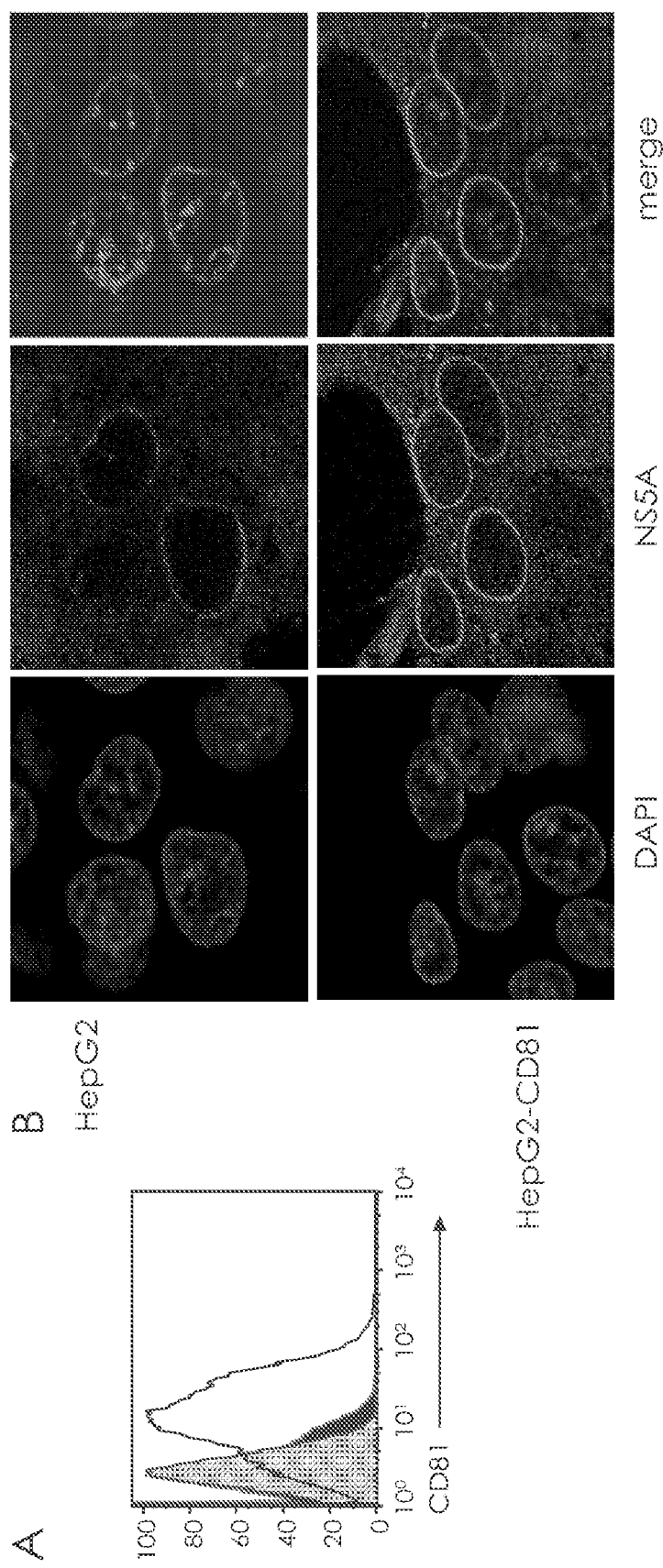
Figure 8:
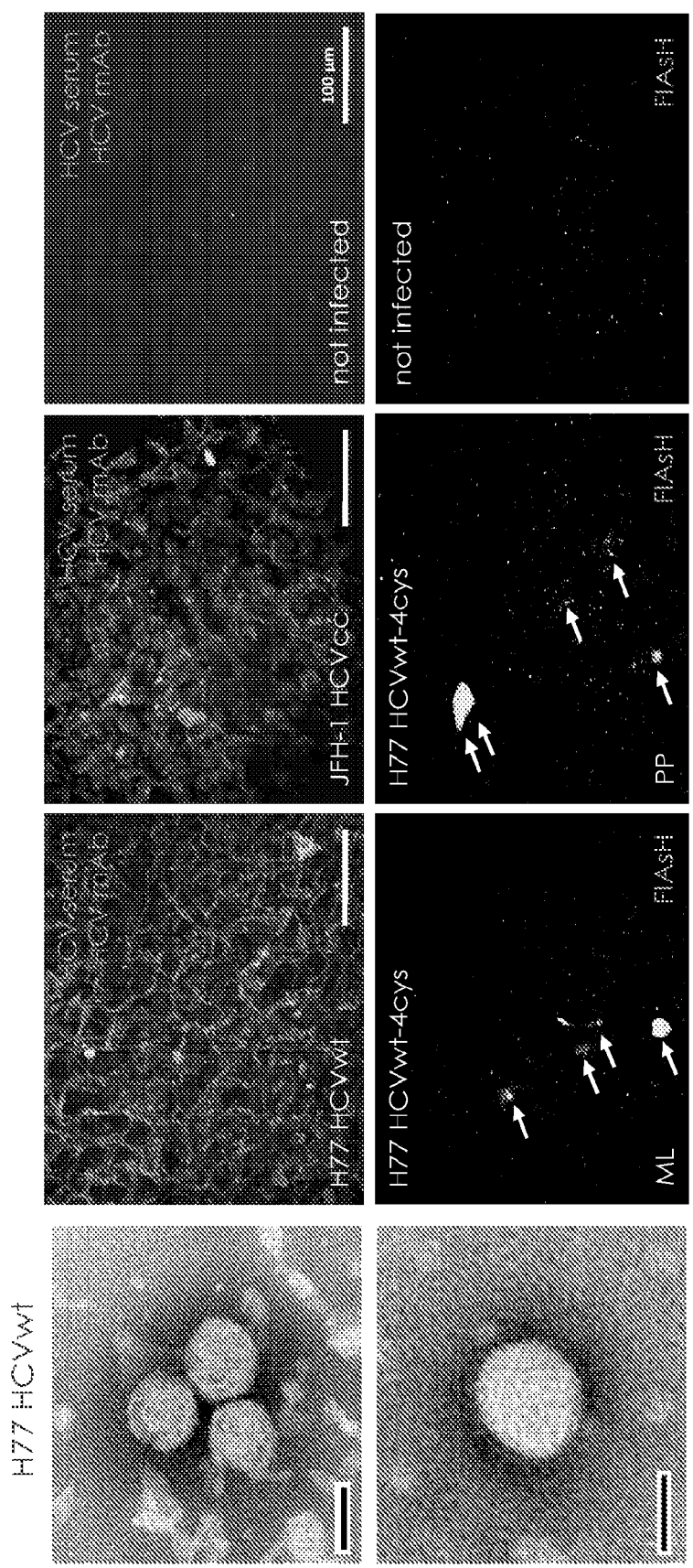

Incubation of HuH-7.5 cells with HCVbp yielded a low infectivity signal, which could be due to the small number of positive cells and low levels of structural proteins expressed in their cytoplasm (not shown). To ensure amplification of the infection signal by viral spreading, a plasmid expressing HCV core-to-NS2 genes (without genomic 5'-UTR) under CMV promoter was transfected into HuH-7.5 cells a few hours after viral infection. Viral 5'-UTR was detected at significant levels only as from the third day of infection (FIG. 4B). As previously reported, full-length HCV particles display a broad range of buoyant densities and infectivity, the latter not directly correlating with the amount of RNA they associate with (Yi, M. et al., 2006. *Proc. Natl. Acad. Sci. USA* 103, 2310-2315). The peak of infectivity was generally obtained with HCVbp displaying densities of 1.08-1.13 g/cm$^3$, which corresponded to a low peak of HCV RNA (FIG. 3B). We also confirmed that CD81 expression was required for HCVbp entry. Albeit of hepatic origin, HepG2 cells lack CD81 and are poorly permissive for HCVpp or HCVcc infection (Flint, M. et al., 2006. *J. Virol.* 80, 11331-11342). Their stable transduction with a recombinant lentivirus expressing human CD81 enhanced HCVbp entry as detected by NS5A expression after a few days (FIG. 7A-B).

BHK-WNV1 Cells Produce Authentic Wild Type HCV.

Next, we tested the possibility that BHK-WNV1 cells could also produce authentic virus by expressing 'wild type' genome (HCVwt; consensus sequence of H77 strain (Kolykhalov, A. A. et al., 1997. *Science* 277, 570-574). The materials released in the supernatants were fractionated on sucrose gradient and analyzed by negative staining EM. Spherical particles of 50-60 nm in diameter were observed in fractions with buoyant densities of 1.08-1.13 g/cm$^3$ (FIG. 8, left panels). As HCV isolates from patients are poorly infectious in HuH-7.5 cells, the infectivity of HCVwt was tested in human liver slices. Like primary human hepatocytes (Buck M., 2008. *PLoS One* 3, e2660), liver slices can be infected ex vivo with HCVcc (manuscript in preparation). After incubation of liver slices with BHK-WNV1-produced HCVwt (H77 strain (Kolykhalov, A. A. et al., 1997. *Science* 277, 570-574) or HuH-7.5-produced HCVcc (JFH-1 strain (Wakita, T. et al., 2005. *Nat. Med.* 11, 791-796), specific staining by anti-HCV antibodies was observed with a multifocal confocal microscope (FIG. 8, upper middle panels); the signal appeared within the slices after a few days and increased up to 6-10 days. Similar results were obtained with HCVwt-4-cys, i.e. encoding a tetra-cysteine tag (Griffin, B. A. et al., 1998. *Science* 281, 269-272) within one of its non-structural genes, as previously validated in HuH-7.5 cells (cf. above). Six to eight days after infection of liver slices with HCVwt-4-cys, they were incubated with a permeant biarsenical dye and observed using a two-photon confocal microscope; specific staining was detected predominantly in periportal spaces, and also in mediolobular areas (FIG. 8C, lower panels) of HCVwt-4-cys-incubated slices, indicating that BHK-WNV1 cells produced HCVwt-4-cys that could infect human liver slices, ex vivo.

Example 5

Reporter Gene Readout in HCV Replication-Permissive and Non-Permissive Target Cells As HCV replication was reported to be mostly restricted to hepatic cells (Jopling, C. L. et al., 2005. *Science* 309, 1577-1581), we designed a system of plasmids for detecting entry without relying on viral replication by amplifying the incoming signal. A new bi-cistronic HCV construct was made, in which the EMCV IRES is in frame with the ORF of bacteriophage SP6 DNA-dependent RNA polymerase (SP6pol), the reporter gene therefore replacing the HCV replication genes (FIG. 1C; cf. Materials and Methods). This new construct was expressed in BHK-WNV1 cells to produce reporter RNA-containing particles (HCVrp; FIG. 1C). Since the SP6pol-encoding RNA to be encapsidated into HCVrp is not a replicon, a system of reporter plasmids was designed to detect viral entry by amplifying the incoming signal in trans and produce EGFP-Firefly luciferase (FFL) fusion protein under the control of both T7 and SP6 promoters (FIG. 1C). To ensure sufficient sensitivity of detection, two plasmids are co-transfected that encode SP6 or T7 polymerase under the control of T7 or SP6 promoters, respectively; upon stimulation, the two plasmids cross-amplify each other's transcription, providing required sensitivity for detecting few incoming RNA molecules. Previous validation of amplified reporter system has been achieved either by transfecting T7 DdRP RNA produced in HuH-7 cells infected with vTF7-3, a recombinant vaccinia virus encoding T7 DdRP (Fuerst, T. R. et al., 1986. *Proc. Natl. Acad. Sci. USA* 83, 8122-8126), or, more directly, T7 DdRP protein (with Proteojuice, not shown). The leakiness of the system, i.e. the detection of FFL activity in the absence of incoming RNA, was greatly reduced by incubating the target cells with low concentrations of actinomycin D following their transfection, without blocking the readout of specific incoming signal.

Study of HCV Cell Entry with BHK-WNV1 Cell-Produced HCVrp (HCV Reporter Particles).

To adapt these systems for entry studies, the ORF of bacteriophage SP6 DNA-dependent RNA polymerase (SP6pol) was inserted in frame with the EMCV IRES, keeping the last third of NS5B upstream 3'-UTR. This new construct was expressed in BHK-WNV1 cells to produce reporter RNA-containing particles (HCVrp; FIG. 1). Since the SP6pol-encoding RNA to be encapsidated into HCVrp is not a replicon, a system of plasmids was designed to detect viral entry by amplifying the incoming signal in trans and produce EGFP-Firefly luciferase (FFL) fusion protein (Methods). With this system of detection, incubation of HuH-7.5 cells with HCVrp resulted in a FFL activity that increased in a dose-dependent fashion; in contrast, the activity remained at background levels with materials released by parental BHK-21 cells (FIG. 5A). No RNL activity was detected, confirming that WNV SG-rep was not packaged by infectious HCV particles. The maximum entry signal was generated by particles with buoyant densities of 1.13-1.15 g/cm$^3$ (FIG. 5B); HCVrp's slightly heavier density is perhaps linked to lesser association with lipid droplets (Miyanari, Y. et al., 2007. *Nat. Cell. Biol.* 9, 1089-1097). Construct encoding HCV proteins up to NS2 elicited a higher viral entry signal than one without NS2 (FIG. 5C), in line with previous observations in hepatic cells (Jones, C. T. et al., 2007. *J. Virol.* 81, 8374-8383).

Lack of requirement for HCV replication allowed us to test several cells lines for correlation between expression of candidate receptors and viral entry (Table 1). Pretreatment of HuH-7.5 cells with siRNA pools targeting HCV candidate receptors (SR-B1, CD81, ASGP-R subunits 1 and 2, or claudin-1 (Scarselli, E. et al., 2002. *EMBO J.* 21, 5017-5025; Pileri, P. et al., 1998. *Science* 282, 938-941; Saunier, B. et al., 2003. *J. Virol.* 77, 546-559; Evans, M. J. et al., 2007. *Nature* 446, 801-805) specifically inhibited the signal generated by HCVrp entry (FIG. 6A), SR-B1 siRNA being the most consistently effective (FIG. 6B). Consistently, antibodies against CD81 and SR-B1 significantly inhibited HCVrp entry (FIG. 6E). Pre-incubation of HCVrp with anti-HCV E2 hypervariable region 1 (HVR-1) antibody inhibited their entry into HuH-7.5 cells (FIG. 6D), supporting previous observation that HVR-1 interacts with SR-B1 (Scarselli, E. et al., 2002. *EMBO J.* 21, 5017-5025) is critical for neutralization (Farci, P. et al., 1996. *Proc. Natl. Acad. Sci. USA* 93, 15394-15399).

TABLE 1

Candidate receptor expression in cell lines

| Cell type | Reporter assay | Expressions of candidate receptors | ASGP-R expression |
|---|---|---|---|
| HuH-7 | ++ | CD81, SR-BI[b, c], claudin-1[d], occludin[e] | yes[f] |
| HuH-7.5 | ++/+++ | CD81, SR-BI, claudin-1, occludin | yes |
| Bsc-1 | ++/++++ | CD81, SR-BI (others ND) | yes |
| 293T | ++ | CD81, occludin[i] (no SR-BI or claudin-1) | yes (HEK-293 cells) |
| HeLa | ± | CD81, SR-BI, occludin[h] (no claudin-1) | ND |
| Hos-CCR5 | ± | ND | ND |
| SW13 | –[a] | ND | ND |
| HepG2 | –[a] | SR-BI, claudin-1[i], occludin[j] (no CD81) | yes |

ND = not determined.

[a] cells were transfected with plasmid expressing EGFP to assess their transfectability after infection
[b] another name for SR-BI in humans is Cla-1;
[c] Wadsack et al., 2003. *Int. J. Biochem. Cell Biol.* 35, 441-454;
[d] Evans et al., 2007. *Nature* 446: 801-5;
[e] Ploss et al., 2009. *Nature* 457, 882-886;
[f] Huang et al., 2002. *J. Biol. Chem.* 277, 37798-37803;
[g] Stewart et al., 2002. *Biochem. Biophys. Res. Commun.* 299, 62-73;
[h] Bordin et al., 2004. *Mol. Cancer Res.* 2, 692-701;
[i] Mee et al., 2009. *J. Virol.* 83, 6211-6221 and
[j] Schmitt et al., 2004. *J Hepatol.* 41, 274-83.

Example 6

To assess the CD81 requirement for HCV particles entry in this study, we transduced HepG2 cells with a recombinant lentivirus expressing human CD81. Albeit of hepatic origin, HepG2 cells lack CD81 and are poorly permissive for HCVpp or HCVcc infection (Flint, M. et al., 2006. *J. Virol.* 80, 11331-11342). We stably transduced HepG2 cells with a recombinant lentivirus expressing human CD81. The stable CD81 expression in these cells was confirmed by its detection at the cell surface of transduced cells (FIG. 7A, left panel) as it was absent in parental cells. Two days after infection with HCV particles produced in BHK-WNV1 cells, expression of NS5A was detected at higher levels in HepG2-CD81 than in parental cells (FIG. 7B), indicating that the presence of CD81 enhanced HCV entry in HepG2-CD81 cells.

Example 7

Figure 9A:
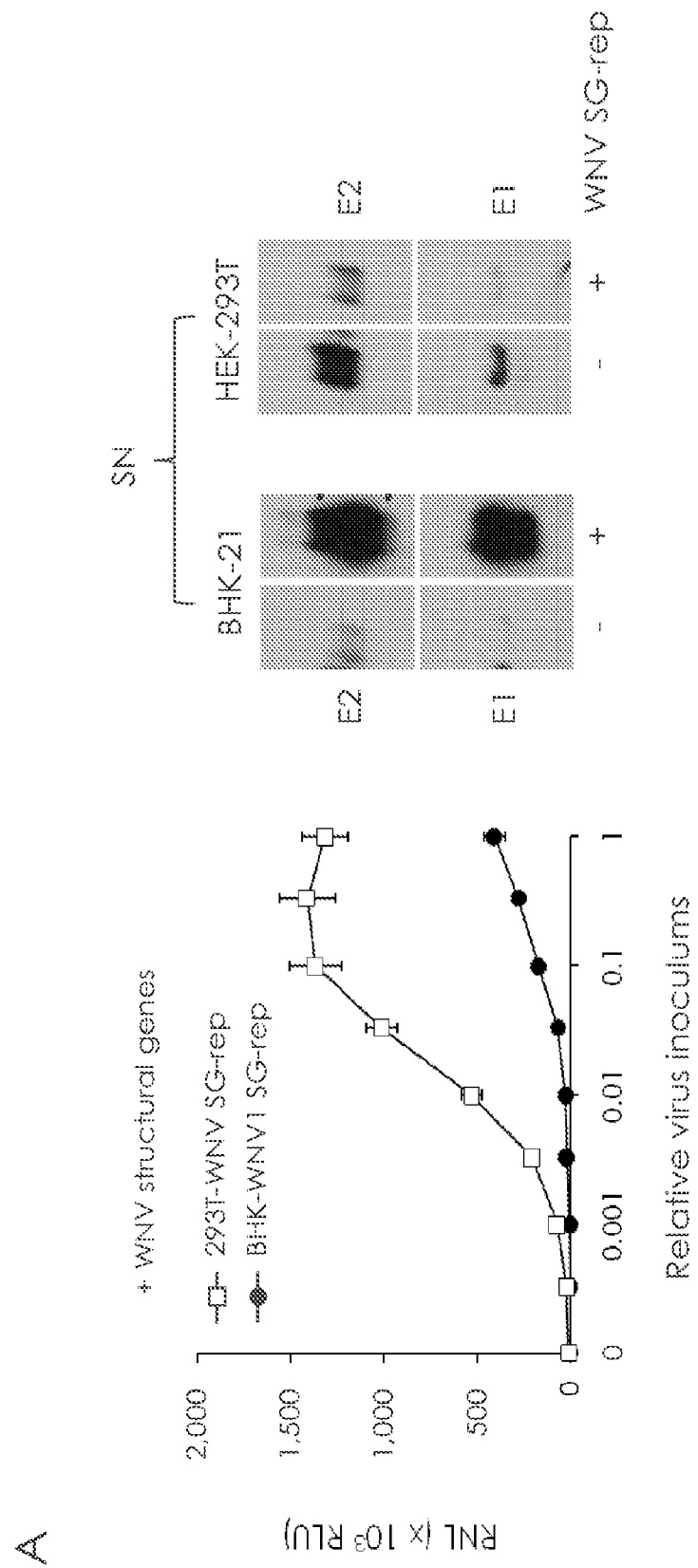
FIG. 9 illustrates enhanced release of HCV particles involves cellular factors induced by WNV-SG rep, not its replication per se. (A) (Left) BHK-21 or HEK-293T cells bearing a WNV SG-rep were transfected with a plasmid encoding the WNV core, prM and E; released WNVrp were incubated with HuH-7.5 cells and RNL activity was measured in cell lysates two days later. (Right) BHK-21 or HEK-293T cells were transfected with a plasmid encoding HCV structural genes, and E1 and E2 proteins released in particles were analyzed by WB. (B) (Left) BHK-WNV1 cells were treated with either IFN, IFN+MPA or IFN+Ribavirin, and RNL activity (indicating the level of WNV replication) was measured in 25,000 cells. (Right) Control and antiviral-treated BHK-WNV1 cells were transfected with plasmid encoding HCVbp; three days later, E1 content in the cell lysates and pelleted supernatants were determined by WB; RNL was used to confirm the WNV SG-rep inhibition by antivirals. (C) Antiviral-treated BHK-WNV1 cells were transfected with HCVbp-coding plasmid, and three days later, cells were fixed and observed by TEM; (left) Membrane rearrangements in IFN+MPA-treated cells and formation of virus-like particles within LV (arrows) next to the rough ER protrusions (arrowhead) (magnification 6,000×); (middle and right) At higher magnification, LV are filled with virus-like particles (magnification 20,000× and 25,000×, respectively).

Enhanced Release of HCV Particles Involves Cellular Factors Induced by WNV-SG Rep, not its Replication Per Se The mechanism of enhanced HCV release was our next question. After establishing WNV SG-rep in naïve 293T cells (293T-WNV cells), upon expression of WNV structural genes, released WNVrp were highly infectious in HuH-7.5 cells (FIG. 9A, left). However, HCVbp or HCVrp released by 293T-WNV cells did not infect HuH-7.5 cells (not shown), suggesting that additional, yet-unidentified cellular factors are required. As a matter of fact, WNV SG-rep failed to enhance, or even slightly inhibited, the production and release of HCV proteins in 293T cells (FIG. 9A, right).

Example 8

Treatment of BHK-WNV1 Cells with Antiviral Drugs.

Figure 9B:
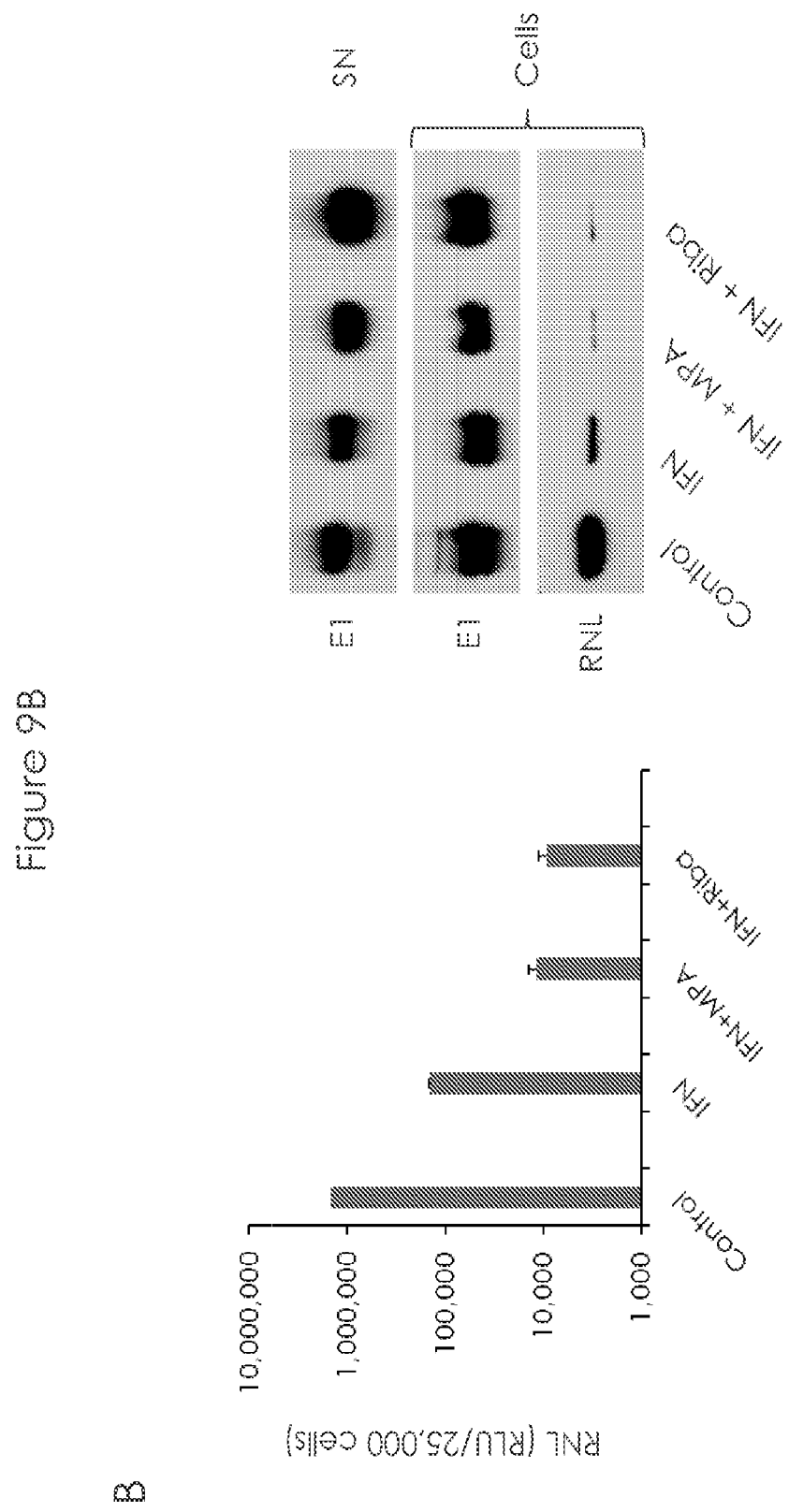

BHK-WNV1 cells were treated with IFN from human leukocytes (Sigma) at 3,000 IU/ml for 10 days, then further treated for 7 days with either: i) IFN alone (1,500 IU/ml), ii) IFN (1,500 IU/ml) plus mycophenolic acid (MPA; 0.5 μg/ml (Sigma), or iii) IFN (1,500 IU/ml) plus Ribavirin (25 μM) (Sigma). Cells were then transfected with HCV coding plasmids [p684-SG (L+I)-HDV]. The inhibition of WNV SG-rep by the antiviral treatments was assessed by the production of RNL activity and expression by WB and compared to that produced by the parental/untreated BHK-WNV cells. The treatment of BHK-WNV1 cells for up to two weeks with antivirals significantly reduced the replication of WNV SG-rep and, yet, only had marginal effect on HCVbp release (FIG. 9B). In HCV-infected patients, the standard of care (pegylated IFN alpha2+Ribavirin) is known to reduce viral loads within the first 48 hours (Layden, T. et al., 2000. *Semin. Liver Dis.* 20, 173-183), suggesting that HCVbp production in BHK-WNV1 cells, like for HCVrp, occurred without having to establish viral replication first. In spite of a significant inhibition of WNV SG-rep activity, cytoplasmic membrane rearrangements (VP and CM) persisted, and upon expression of bi-cistronic FL HCV, LV filled with virus particles developed (FIG. 9C, left panel). HCV particles in anti-viral treated cells showed no significant morphological difference with those in untreated cells (FIG. 9C, middle and right panels; compare to FIG. 3A), suggesting that changes in intracellular trafficking induced by WNV SG-rep, and not its function per se, favored the release of HCV particles.

Example 9

Identification of Cellular Factors Required for HCV Production

To test whether the production of infectious particles was restricted to BHK-WNV1 cells, WNV SG-rep was transferred into naïve BHK-21 cells, and twenty stable clones were obtained. At first, all of them failed to produce infectious particles or even release more HCV materials (not shown). A clone (BHK-WNV2.13 cells) was selected based on its ability of releasing, upon passages, increasing amounts of infectious HCVrp. This was a trend observed with most clones suggesting that, over time, BHK-21 cells further adapted to WNV SG-rep, which correlated with morphological changes (not shown). We used initial passages of BHK-WNV2.13 cells and performed a differential screening of its mRNAs with those of original BHK-WNV1 cells (Methods). After stringent screening (FIG. 10A), thirty-seven cDNA clones were obtained (FIG. 10B).

Example 10

Figure 10C:
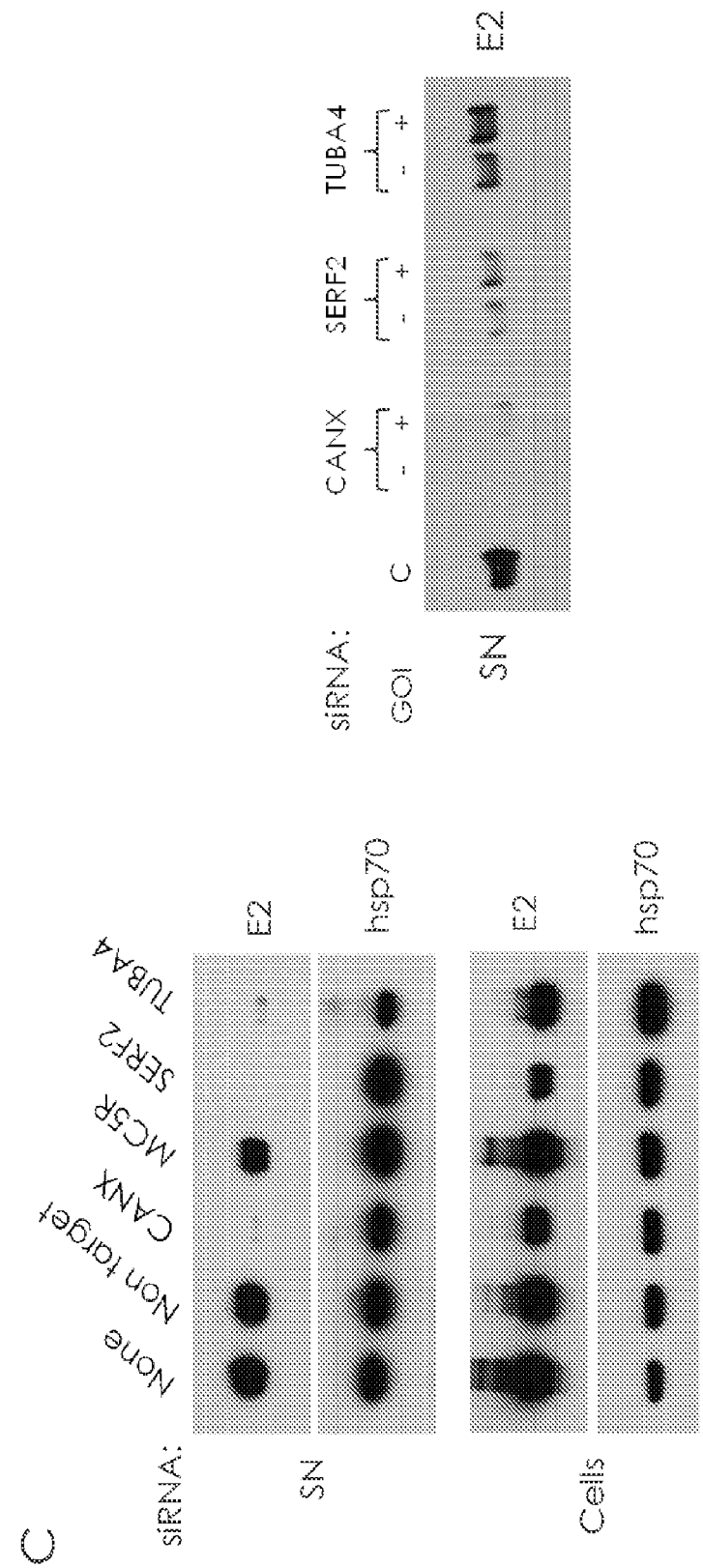
FIG. 10 illustrates the identification of cellular factors (calnexin, small-EDRK-rich factor 2/SERF2 and tubulin 4A) that are involved in the release of infectious HCV particles by BHK-WNV1 cells. A) Differential screening strategy between infectious HCV-producing and non-producing BHK-WNV cells: The flowchart describes how the differential screening was performed. See Subtractive hybridization, described in Methods, for more details. B) Table 2 illustrates the list of BHK-WNV1 transcripts identified after subtractive cloning with mRNA from BHK-WNV2.13 cells. C) (left) BHK-WNV1 cells were treated with the indicated siRNAs for 2 days then transfected with HCVp7 plasmid. Cells and pelleted supernatants were analyzed 48 hr later by Western blot. (right) BHK-WNV1 cells were treated with siRNA directed against CANX, SERF2 or TUBA4 genes for 2 days. Cells were then reseeded, and the following day, were transfected with HCVp7 alone, or, together with the plasmid expressing the knocked-out gene of interest (GOI); the particles released in the SN were analyzed by WB, showing partial reversal of inhibition. C=control siRNA. D) BHK-WNV1 cells control (first column), or previously transfected with calnexin siRNA (second column), were transfected with plasmid encoding HCVbp. Three days later, IF was performed with anti-HCV serum and anti-calnexin (CANX), followed by confocal microscopy analysis; (Other panels) BHK-WNV1 cells transfected with plasmid encoding HCVbp followed by immunofluorescence (IF) analysis with anti-HCV serum and calreticulin (CRT) or ERGIC-53 antibody. E) BHK and BHK-WNV1 cells were seeded on a 8-well chamber slide, and the next day, IF was performed with anti-ERGIC-53 and anti-CRT antibodies followed by confocal microscopy.

BHK-WNV1 cells were treated with siRNA targeting identified factors. Cellular v-src homolog (c-src; not shown) or melanocortin-5 receptor (MC5R; FIG. 10C) siRNAs did not alter HCV production or release; instead, these factors could be required for further adaptation of BHK cells to WNV SG-rep (Hirsch, A. J. et al., 2005. *J. Virol.* 79, 11943-11951), as also indicated by inhibition of WNV SG-rep activity with MC5R siRNA (not shown). siRNA targeting small EDRK-rich factor-2 (SERF2) partially inhibited HCV production, and, strongly, their release (FIG. 10C). SERF2 is a ubiquitous protein of unknown function, predicted to be a nucleic acid-binding protein (Scharf, J. M. et al., 1998. *Nat. Genet.* 20, 83-86), and potentially subject to lysine acetylation (Kim, S. C. et al., 2006. *Mol. Cell.* 23, 607-618); it could promote HCV production/secretion via proteasome activator PSME3/PA28gamma, an HCV core-binding protein (Moriishi, K. et al., 2003. *J. Virol.* 77, 10237-10249). siRNA targeting alpha-tubulin-4-a (TUBA4), a protein involved in the formation of microtubules, strongly decreased the release of HCV particles without affecting their production (FIG. 10C). Microtubules were recently reported to play a role in HCV entry via their interaction with core (Roohvand, F. et al., 2009. *J. Biol. Chem.* 284, 13778-13791).

Example 11

Maturation of Envelope Protein Carbohydrate Residues is Required for HCV Production Calnexin (CANX) was the most often identified cDNA (Table 2, See FIG. 10B), and it was recruited to an intracytoplasmic sub-compartment together with HCV proteins (FIG. 10D, left panels). The treatment of BHK-WNV1 cells with calnexin siRNA slightly decreased their amount and led to the scattering of HCV proteins (FIG. 10D, center left panels), thus reverting the phenotype induced by WNV SG-rep in parental cells (FIG. 12A). Together with calreticulin (CRT), calnexin is an ER-resident foldase ensuring the proper conformation of nascent glycoproteins. Another C-type lectin, ER-to-Golgi intermediary compartment protein of 53 kDa (ERGIC-53), is involved in targeting properly folded glycoproteins to the Golgi apparatus for maturation of their carbohydrate residues by resident glyco-enzymes (Ellgaard, L. & Helenius, A. 2003*Nat. Rev. Mol. Cell. Biol.* 4, 181-191). Both calreticulin and ERGIC-53 were excluded from the HCV sub-compartment (FIG. 10D, right panels) and their expression down-regulated by WNV SG-rep (FIG. 10E).

This led us to examine the involvement of envelope protein glycosylation in HCV release. In both parental BHK-21 and BHK-WNV1 cells, deoxynojirimycin that inhibits the trimming of nascent glycoproteins by ER glucosidase-I (Steinmann, E. et al., 2007. *Hepatology* 46, 330-338), decreased the release of HCV particles (FIG. 2C), indicating that glycosylation of HCV envelope proteins is critical for this process. We then tested the effect of brefeldin A (BFA) that blocks GDP-GTP exchange on sensitive ADP-ribosylation factor isoforms, thereby interrupting intracellular traffic to Golgi apparatus (Zeghouf, M. et al., 2005. *Biochem. Soc. Trans.* 33, 1265-1268); consequently, glycoproteins remain with low-mannose N-glycans and sensitive to endo-β-N-acetylglucosaminidase-H (endo-H). The treatment of BHK-WNV1 cells with BFA abrogated HCV secretion (FIG. 11A), and enhanced the electrophoretic mobility of intracellular HCV envelope proteins, their carbohydrate residues being likely trimmed by ER-resident glucosidases and mannosidases and not further matured by Golgi-resident enzymes. This result was consistent with the fact that, while all HCV E2 and E1 intracellular species in BHK-WNV1 cells were sensitive to endo-H, most E2 carbohydrate residues and one of E1 in the released HCV particles had become endo-H resistant (FIG. 11B), indicating they had transited via a compartment containing Golgi-resident enzymes.

Example 12

ER-Golgi Trafficking Factors and HCV Proteins Co-Localize within a Cytoplasmic Sub-Compartment Using bioinformatic analysis (IPA software, Ingenuity Systems, CA), small GTPase Rab1 was identified as a possible connecting partner of those previously identified (not shown). Rab1 regulates the transport of proteins newly synthesized in ER to Golgi apparatus. Upon GTP-binding, Rab1 recruits tethering p115/USO1 onto COPII-coated vesicles budding from ER (Allan, B. et al., 2000. *Science* 289, 444-448). In BHK-21 cells, Rab1 was scattered into several spots in the cytoplasm and co-localized with HCV proteins (FIG. 12A, left panels); WNV SG-rep greatly enhanced its expression (FIG. 12A, right panels) that, then, coalesced into one or two larger spots together with HCV proteins, predominantly in their periphery (FIG. 12A, lower right panel). HCV protein expression was greatly reduced by Rab1 siRNA (FIG. 12B, left panels), and scattered like in parental BHK-21 cells (FIG. 12B, right panels); concomitantly, release of HCV particles also decreased (FIG. 12B, left panels). Interestingly, in BHK-WNV1 cells, the expression of GDP dissociation inhibitor (GDI) that recycles Rab1-GDP in complex with heat-shock protein 90 (Chen, C. Y., & Balch, W. E. 2006. *Mol. Biol. Cell.* 2006 17, 3494-3507), was enhanced and co-localized with HCV proteins in a pattern reminding that of Rab1 (FIG. 12C), perhaps to prevent its recycling. Two additional factors were also recruited to this compartment, from which mitochondria were excluded (FIG. 12D): atlastin-GTPase-1, implicated in maintaining ER compartment and ER-to-Golgi trafficking (Orso, G. et al., 2009. *Nature doi:*10.1038/nature08280; Hu, J. et al., 2009. *Cell* 138, 549-561), and p115/USO1 (Allan, B. et al., 2000. *Science* 289, 444-448), also required for membrane fusion of ER-to-Golgi secretory vesicles.

Collectively, our results provide the first evidence that cellular rearrangements previously induced by a member of the Flaviviridae family (WNV) in selected cells render them permissive for the formation and release of infectious viral particles of a distant family member (HCV), and this without requiring viral replication. This concept supports the development of new tools for exploring the biology of viruses and identifying new means of countering their evolving strategy.

Figure 13A:
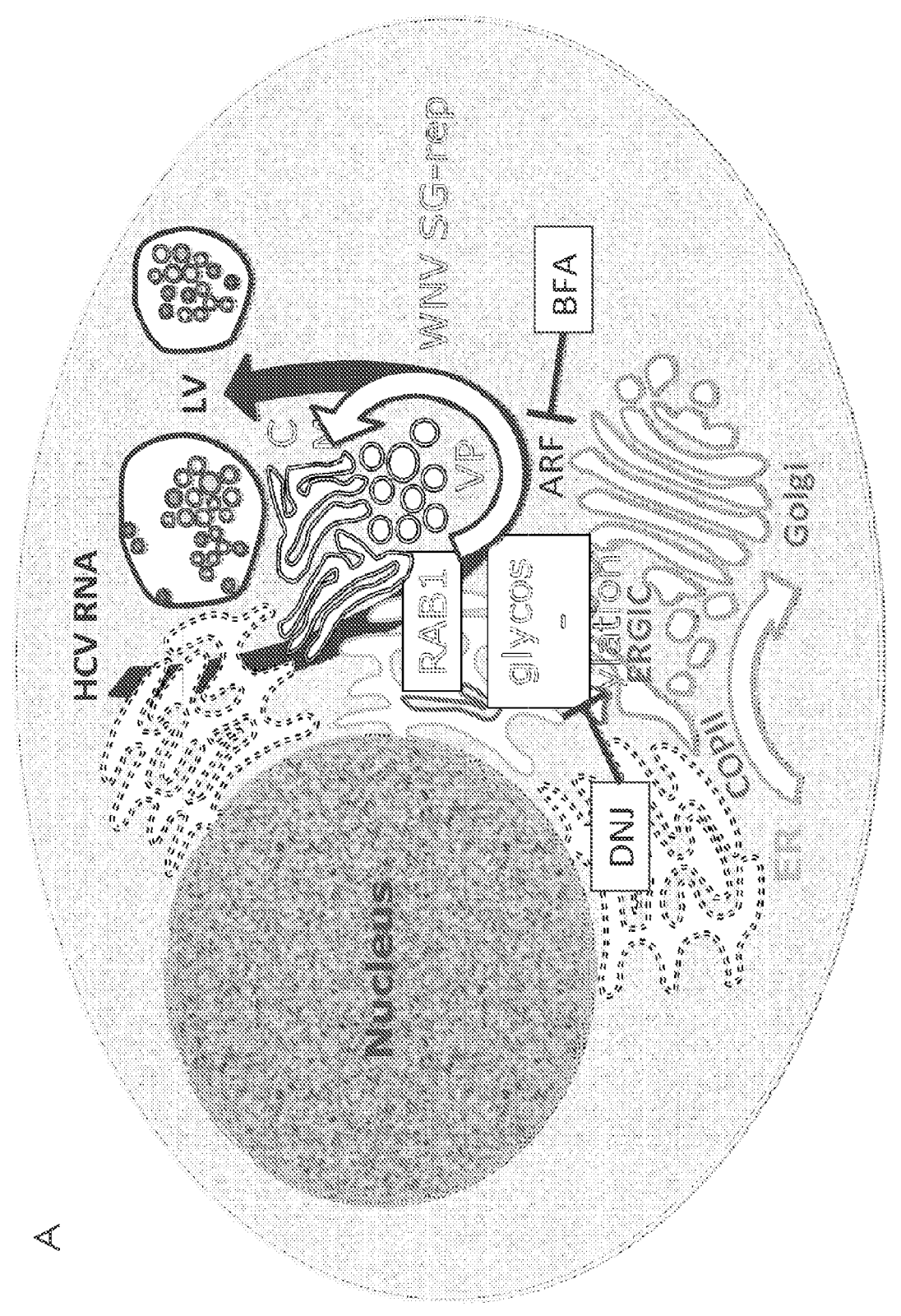
Figure 13B:
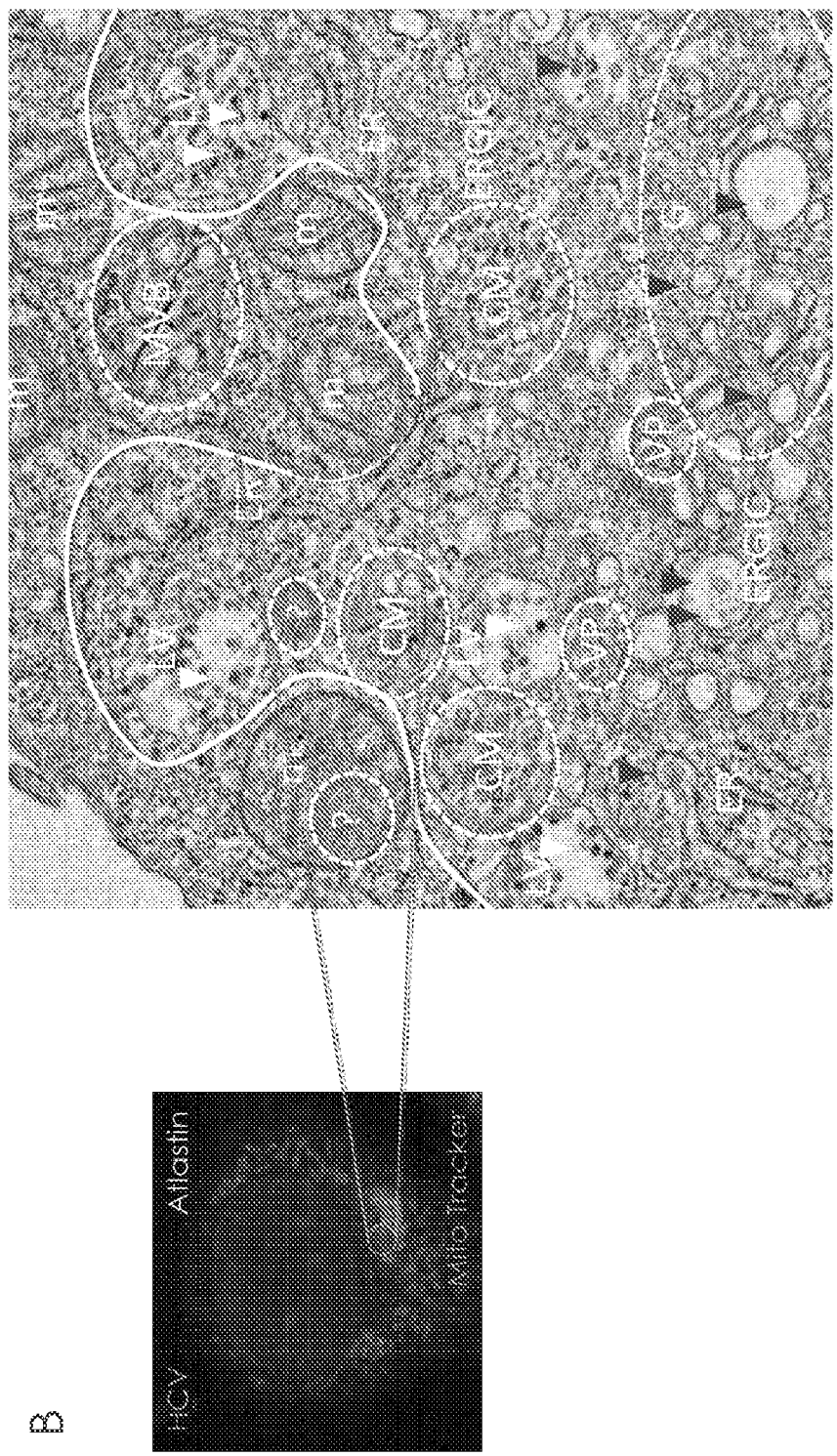
FIG. 13 illustrates a proposed model of HCV assembly by BHK-WNV1 cells. A) WNV-SG rep induced membrane rearrangements characterized by the presence of vesicle packets (VP, site of WNV RNA replication) and convoluted membranes (CM, site of RNA translation and polyprotein processing) (Mackenzie J. 2005. Traffic 6, 967-977). Upon expression of HCV polyprotein, large vesicles (LV) that displayed clusters of enveloped virus particles (~50-60 nm in diameter) budding into their lumens, were observed in the close proximity of dilated, rough ER (endoplasmic reticulum). Translation of HCV RNA likely took advantage of ER membrane rearrangement induced by WNV SG-rep as well as up regulated cellular factors, such as Rab1. To exit ER-related membranes, viral envelope glycoproteins likely required COPII-coated vesicles that are regulated by Rab1. HCV Envs translocated to a Golgi-derived compartment, as their glycosylation pattern suggests, possibly via ERGIC (ER-to-Golgi intermediary complex). Thereafter, LV transited to the cell surface where they fused with the plasma membranes and released virus particles into the culture medium. HCV production and/or secretion were blocked by several compounds: i) DNJ, by inhibiting the initiation of the maturation of carbohydrate residues on HCV envelope proteins in the ER lumen; ii) Brefeldin A (BFA), by inhibiting the activation of ADP-ribosylation factors (ARFs) that is required to maintain the Golgi stack and trans-Golgi network, and iii) rab1 siRNA that inhibited HCV production and release. B) (left) IF analysis showing the co-exclusion of HCV and atlastin from mitochondria, the latter surrounding the HCV-enriched compartment. (right) a similar aspect observed by TEM: m=mitochondria; LV=large vesicles; CM=convoluted membranes; VP=vesicle packets; ER=membranes from endoplasmic reticulum; G=Golgi stacks; ERGIC=vesicles from ER-to-Golgi intermediary compartment; MVB=multi-vesicular body; white arrowhead=electron-dense viral particles; black arrowhead=nascent viral particles. C) Immuno-EM analyses of BHK-WNV1 cells transfected with HCVbp-construct: Three days after transfection, cells were fixed and thawed cryosections were labeled with antibodies specific for HCV core and E1. (upper, left panel) Immunogold-labeled anti-core antibody (black arrowhead) specifically stained dilated ER cisternae that extend into a large vesicle (LV). (middle and right upper panels) Immunogold particles also detected core proteins on the membrane periphery of this LV and in the LV lumen. (lower panels) Immunogold-labeled-anti-E1 antibody detected virus-like structures within the LV and also inside ER cisternae.

While HCV envelope proteins would otherwise be retained in the ER of BHK-21 cells (Dubuisson, J. et al., 1994. *J. Virol.* 68, 6147-6160; Blanchard, E. et al., 2002. *J. Virol.* 76, 4073-4079), cellular changes triggered by WNV replication rendered BHK-21 cells permissive for assembly and release of infectious HCV without involvement of its own replication. ER, ERGIC and Golgi membranes together with a diversity of membrane-associated proteins were 'hijacked' by WNV replication to create a heterogeneous cytoplasmic sub-compartment (FIG. 13B), to which calnexin was co-targeted with HCV proteins. After HCV core and E1 immuno-gold labeling, nascent HCV particles were observed within dilated ER cisternae (FIG. 13C) and also budding into LV filled with viral particles (FIGS. 13B-C), suggesting that the cytoplasmic sub-compartment is the viral assembly site. It also contains membranes deriving from Golgi apparatus required for viral maturation, as indicated by: i) involvement of ARF in HCV secretion; ii) HCV co-localization with p115/USO1 (FIG. 12D) and GM130 (not shown), iii) the presence of nascent particles with ERGIC vesicles and Golgi, and iv) the resistance of HCV envelope proteins to endo-H in released particles.

What is claimed:

1. A recombinant mammalian cell transformed to contain:
   a plasmid encoding a T7 or SP6 promoter operably linked to one or more HCV genes;
   a subgenomic replicon from a flavivirus; and
   a cytoplasmic T7 and SP6 RNA amplification system, wherein the HCV genes encode the structural proteins or replication-competent HCV particles, and wherein the flavivirus is West Nile virus or dengue 2 virus.

2. The recombinant mammalian cell according to claim 1, wherein said one or more HCV genes comprise an HCV full-length bi-cistronic genome.

3. The recombinant mammalian cell according to claim 1, wherein said one or more HCV genes comprise an HCV full-length wild type genome.

4. The recombinant mammalian cell according to claim 1, wherein said one or more HCV genes comprise one or more HCV structural proteins or one or more non-structural proteins.

5. The recombinant mammalian cell according to claim 4, wherein the one or more HCV structural proteins are selected from C (core), E1 or E2.

6. The recombinant mammalian cell according to claim 4, wherein the one or more HCV non-structural proteins are selected from p7 or NS5B.

7. The recombinant mammalian cell according to claim 1 wherein the first host cell line is from a BHK-21 stable cell line.

8. The recombinant mammalian cell according to claim 1 wherein the flavivirus is West Nile virus.

9. The recombinant mammalian cell according to claim 8 wherein said subgenomic replicon also expresses an antibiotic selection gene and a reporter gene.

10. The recombinant mammalian cell according to claim 9 wherein said reporter gene is *Renilla* luciferase (RNL) and the antibiotic selection gene is blasticidin.

11. The recombinant mammalian cell of claim 2 wherein the HCV full-length bi-cistronic genome is genotype 1a.

12. The recombinant mammalian cell of claim 2 wherein the HCV full-length bi-cistronic genome is operably linked to a hepatitis delta ribozyme terminator.

13. The recombinant mammalian cell of claim 1 wherein said one or more HCV genes comprise an HCV full-length bi-cistronic genome or wild type genome that has been tagged with a tetracysteine (TC)-tag.

14. The recombinant mammalian cell of claim 13 wherein a non-structural HCV gene has been tagged with said tetracysteine (TC) tag.

15. The recombinant mammalian cell according to claim 1 wherein the one or more HCV genes are isolated from a HCV recovered from a patient.

16. The recombinant mammalian cell according to claim 1 wherein the HCV genotype is 1a.

17. The recombinant mammalian cell according to any one of the preceding claims wherein the cytoplasmic T7 polymerase and SP6 polymerase RNA amplification system comprises:
   a plasmid encoding a T7 polymerase promoter operably linked to an EMCV IRES in frame with the SP6 polymerase open reading frame; and
   a plasmid encoding an SP6 polymerase promoter operably linked to an EMCV IRES in frame with the T7 polymerase open reading frame.

18. A method for producing an HCV structural protein or replication-competent HCV particles comprising the steps of:
   providing a recombinant mammalian cell according to claim 1;
   culturing said cells; and
   recovering the HCV structural protein or replication-competent HCV particles from said cell culture.

19. The method according to claim 18 wherein said recovered HCV structural protein or replication-competent HCV particles are produced without HCV virus replication.

20. The method according to claim 18 further comprising purifying HCV particles or structural proteins by passing them through a sucrose cushion or gradient.

21. The method according to claim 18 further comprising purifying HCV particles or structural proteins by passing them through a filter for purifying and concentrating.

22. The recombinant mammalian cell according to claim 1 wherein the cell is from a HuH-7.5 stable cell line.

* * * * *